(12) United States Patent
Wityak et al.

(10) Patent No.: US 6,455,560 B1
(45) Date of Patent: Sep. 24, 2002

(54) ISOXAZOLINE FIBRINOGEN RECEPTOR ANTAGONISTS

(76) Inventors: John Wityak, 25 Jared Dr., Robbinsville, NJ (US) 08691; Prabhakar K. Jadhav, 10 Brendle La., Wilmington, DE (US) 19807

( * ) Notice: Subject to any disclaimer, the term of this patent is extended or adjusted under 35 U.S.C. 154(b) by 0 days.

(21) Appl. No.: 09/905,417

(22) Filed: Jul. 13, 2001

Related U.S. Application Data

(62) Division of application No. 09/442,024, filed on Nov. 17, 1999, now Pat. No. 6,319,937.
(60) Provisional application No. 60/108,940, filed on Nov. 18, 1998.

(51) Int. Cl.[7] ............ A61K 31/42; A61K 81/44; C07D 211/00; C07D 261/02; C07D 413/02
(52) U.S. Cl. ............ 514/378; 514/236.8; 514/326; 514/340; 546/229; 546/239; 548/240
(58) Field of Search .................. 514/378, 236.8, 514/326, 340; 546/229, 237; 548/240

(56) References Cited

U.S. PATENT DOCUMENTS

| | | |
|---|---|---|
| 5,281,585 A | 1/1994 | Duggan et al. ............ 514/79 |
| 5,446,056 A | 8/1995 | Wityak et al. ............ 514/340 |
| 5,455,243 A | 10/1995 | Duggan et al. ............ 514/218 |
| 5,489,693 A | 2/1996 | Linz et al. ............ 548/550 |
| 5,532,255 A | 7/1996 | Raddatz et al. ............ 514/326 |
| 5,607,952 A | 3/1997 | Badorc et al. ............ 514/326 |
| 5,710,159 A | 1/1998 | Voss et al. ............ 514/275 |
| 5,760,028 A | 6/1998 | Jadhav et al. ............ 514/211 |
| 5,760,029 A | 6/1998 | Jadhav et al. ............ 514/211 |

FOREIGN PATENT DOCUMENTS

| | | |
|---|---|---|
| WO | 9514682 | 6/1995 |
| WO | 9514683 | 6/1995 |
| WO | 9638426 | 12/1996 |
| WO | 9823608 | 6/1998 |
| WO | 9843962 | 10/1998 |

OTHER PUBLICATIONS

Wityak et al., "Discovery of potent isoxazoline glycoprotein IIb/IIIa receptor antagonists". (1997) *J. Med. Chem.*, 40(1):50–60.

Alig et al., "Low molecular weight, non–peptide fibrinogen receptor antagonists". (1992) *J. Med. Chem.*, 35(23):4393–4407.

CA abstract: 1997:161925 Meeting abstract: 213th ACS National Meeting, San Francisco, Apr. 13–17 (1997).

*Primary Examiner*—Mukund Shah
*Assistant Examiner*—Sudhaker B. Patel
(74) *Attorney, Agent, or Firm*—Scott K. Larsan; Jing S. Belfield

(57) ABSTRACT

This invention relates to novel isoxazolines of formula (I):

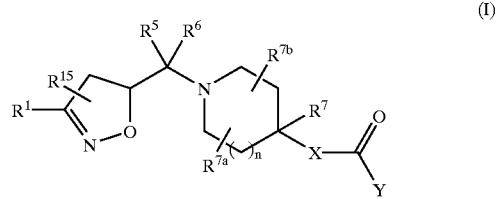

or a pharmaceutically acceptable salt form thereof. This invention also relates to novel isoxazolines of formula (I) which are useful as antagonists of the platelet glycoprotein IIb/IIIa fibrinogen receptor complex, to pharmaceutical compositions containing such compounds, processes for preparing such compounds, and to methods of using these compounds, alone or in combination with other therapeutic agents, for the inhibition of platelet aggregation, as thrombolytics, and/or for the treatment of thromboembolic disorders.

12 Claims, No Drawings

ISOXAZOLINE FIBRINOGEN RECEPTOR ANTAGONISTS

This application is a divisional of U.S. application Ser. No. 09/442,024, filed Nov. 17, 1999 and issued as U.S. Pat. No. 6,319,937 on Feb. 20, 2001, which claims the benefit of U.S. Provisional Application No. 60/108,940, filed Nov. 18, 1998, the contents of which are hereby incorporated bby reference.

FIELD OF THE INVENTION

This invention relates to novel isoxazolines which are useful as antagonists of the platelet glycoprotein IIb/IIIa fibrinogen receptor complex, to pharmaceutical compositions containing such compounds, processes for preparing such compounds, and to methods of using these compounds, alone or in combination with other therapeutic agents, for the inhibition of platelet aggregation, as thrombolytics, and/or for the treatment of thromboembolic disorders.

BACKGROUND OF THE INVENTION

Hemostasis is the normal physiological process in which bleeding from an injured blood vessel is arrested. It is a dynamic and complex process in which platelets play a key role. Within seconds of vessel injury, resting platelets become activated and are bound to the exposed matrix of the injured area by a phenomenon called platelet adhesion. Activated platelets also bind to each other in a process called platelet aggregation to form a platelet plug. The platelet plug can stop bleeding quickly, but it must be reinforced by fibrin for long-term effectiveness, until the vessel injury can be permanently repaired.

Thrombosis may be regarded as the pathological condition wherein improper activity of the hemostatic mechanism results in intravascular thrombus formation. Activation of platelets and the resulting platelet aggregation and platelet factor secretion has been associated with a variety of pathophysiological conditions including cardiovascular and cerebrovascular thromboembolic disorders, for example, the thromboembolic disorders associated with unstable angina, myocardial infarction, transient ischemic attack, stroke, atherosclerosis and diabetes. The contribution of platelets to these disease processes stems from their ability to form aggregates, or platelet thrombi, especially in the arterial wall following injury.

Platelets are activated by a wide variety of agonists resulting in platelet shape change, secretion of granular contents and aggregation. Aggregation of platelets serves to further focus clot formation by concentrating activated clotting factors at the site of injury. Several endogenous agonists including adenosine diphosphate (ADP), serotonin, arachidonic acid, thrombin, and collagen, have been identified. Because of the involvement of several endogenous agonists in activating platelet function and aggregation, an inhibitor which acts against all agonists would represent a more efficacious antiplatelet agent than currently available antiplatelet drugs, which are agonist-specific.

Current antiplatelet drugs are effective against only one type of agonist; these include aspirin, which acts against arachidonic acid; ticlopidine, which acts against ADP; thromboxane $A_2$ synthetase inhibitors or receptor antagonists, which act against thromboxane $A_2$; and hirudin, which acts against thrombin. Additionally, current antiplatelet drugs effective against platelet glycoprotein IIb/IIIa complex include Reopro™, Integrilin™, and Aggrastat™.

A common pathway for all known agonists has been identified, namely platelet glycoprotein IIb/IIIa complex (GPIIb/IIIa), which is the membrane protein mediating platelet aggregation. A recent review of GPIIb/IIIa is provided by Phillips et al. *Cell* (1991) 65: 359–362. The development of a GPIIb/IIIa antagonist represents a promising new approach for antiplatelet therapy.

GPIIb/IIIa does not bind soluble proteins on unstimulated platelets, but GPIIb/IIIa in activated platelets is known to bind four soluble adhesive proteins, namely fibrinogen, von Willebrand factor, fibronectin, and vitronectin. The binding of fibrinogen and von Willebrand factor to GPIIb/IIIa causes platelets to aggregate. The binding of fibrinogen is mediated in part by the Arg-Gly-Asp (RGD) recognition sequence which is common to the adhesive proteins that bind GPIIb/IIIa.

In addition to GPIIb/IIIa, increasing numbers of other cell surface receptors have been identified which bind to extracellular matrix ligands or other cell adhesion ligands thereby mediating cell-cell and cell-matrix adhesion processes. These receptors belong to a gene superfamily called integrins and are composed of heterodimeric transmembrane glycoproteins containing α- and β-subunits. Integrin subfamilies contain a common β-subunit combined with different α-subunits to form adhesion receptors with unique specificity. The genes for eight distinct β-subunits have been cloned and sequenced to date.

Two members of the β1 subfamily, α4/β1 and α5/β1 have been implicated in various inflammatory processes. Antibodies to α4 prevent adhesion of lymphocytes to synovial endothelial cells in vitro, a process which may be of importance in rheumatoid arthritis (VanDinther-Janssen et al., J. Immunol., 1991, 147:4207). Additional studies with monoclonal anti-α4 antibodies provide evidence that α4/β1 may additionally have a role in allergy, asthma, and autoimmune disorders (Walsh et al., J. Immunol., 1991, 146:3419; Bochner et al., J. Exp. Med., 1991 173:1553; Yednock et al., Nature, 1992, 356:63). Anti-α4 antibodies also block the migration of leukocytes to the site of inflammation (Issedutz et al., J. Immunol., 1991, 147:4178).

The $\alpha_v/\beta_3$ heterodimer, commonly referred to as the vitronectin receptor, is another member of the $\beta_3$ integrin subfamily and has been described in platelets, endothelial cells, melanoma, smooth muscle cells and on the surface of osteoclasts (Horton and Davies, J. Bone Min. Res. 1989, 4:803–808; Davies et al., J. Cell. Biol. 1989, 109:1817–1826; Horton, Int. J. Exp. Pathol., 1990, 71:741–759). Like GPIIb/IIIa, the vitronectin receptor binds a variety of RGD-containing adhesive proteins such as vitronectin, fibronectin, VWF, fibrinogen, osteopontin, bone sialo protein II and thrombospondin in a manner mediated by the RGD sequence. Possible roles for $\alpha_v/\beta_3$ in angiogenesis, tumor progression, and neovascularization have been proposed (Brooks et al., Science, 1994, 264:569–571). A key event in bone resorption is the adhesion of osteoclasts to the matrix of bone. Studies with monoclonal antibodies have implicated the $\alpha_v/\beta_3$ receptor in this process and suggest that a selective $\alpha_v/\beta_3$ antagonist would have utility in blocking bone resorption (Horton et al., J. Bone Miner. Res., 1993, 8:239–247; Helfrich et al., J. Bone Miner. Res., 1992, 7:335–343).

Several RGD-peptidomimetic compounds have been reported which block fibrinogen binding and prevent the formation of platelet thrombi. See European Patent Application Publication Number 478363, European Patent Application Publication Number 478328, and PCT Patent Application 9307867, and European Patent Application Publication Number 4512831.

U.S. Pat. No. 5,607,952, published Mar. 4, 1997, discloses fibrinogen receptor antagonists, wherein the substituted 4-phenylthiazole containing compounds of general formula:

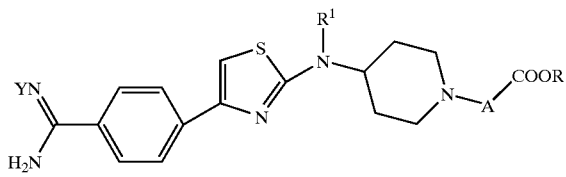

are disclosed.

Canadian Patent Application 2,122,571, published Nov. 11, 1994, discloses fibrinogen receptor antagonists, wherein compounds of general formula:

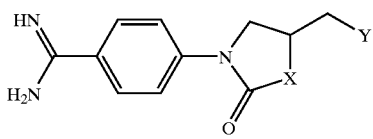

are disclosed.

Copending commonly assigned U.S. patent application U.S. Ser. No. 08/337,920, filed Nov. 10, 1994, Wityak et al.(PCT WO95/14683, published Jun. 1, 1995) discloses compounds having the general formula:

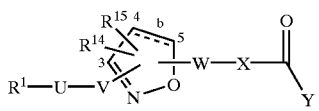

which are useful as IIB/IIIA antagonists. See also related PCT WO96/38426, published Dec. 5, 1996.

Commonly assigned U.S. Pat. No. 5,446,056, issued Aug. 29, 1995, discloses compounds having the general formula:

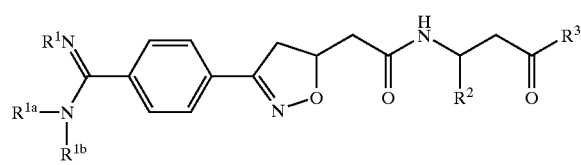

which are useful as IIB/IIIA antagonists. See also PCT WO96/38426, published Dec. 5, 1996.

Commonly assigned U.S. Pat. No. 5,710,159, issued Jan. 20, 1998, discloses compounds having the general formula:

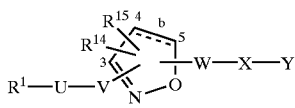

which are useful as $a_vb_3$ antagonists.

None of the above references teach or suggest the compounds of the present invention which are described in detail below.

SUMMARY OF THE INVENTION

The present invention provides novel nonpeptide compounds which bind to integrin receptors thereby altering cell-matrix and cell-cell adhesion processes. The compounds of the present invention are useful for the treatment of thrombosis, inflammation, bone degradation, tumors, metastases, and cell aggregation-related conditions in a mammal.

One aspect of this invention provides novel compounds of Formula (I) (described below) which are useful as antagonists of the platelet glycoprotein IIb/IIIa complex. The compounds of the present invention inhibit the binding of fibrinogen to platelet glycoprotein IIb/IIIa complex and inhibit the aggregation of platelets. The present invention also includes pharmaceutical compositions containing such compounds of Formula (I), and methods of using such compounds for the inhibition of platelet aggregation, as thrombolytics, and/or for the treatment of thromboembolic disorders.

The present invention also includes methods of treating cardiovascular disease, thrombosis or harmful platelet aggregation, reocclusion following thrombolysis, reperfusion injury, or restenosis by administering a compound of Formula (I) alone or in combination with one or more additional therapeutic agents selected from: anti-coagulants such as warfarin or heparin; anti-platelet agents such as aspirin, piroxicam or ticlopidine; thrombin inhibitors such as hirudin or argatroban; or thrombolytic agents such as tissue plasminogen activator, anistreplase, urokinase, streptokinase, or reteplase; or combinations thereof.

The present invention also provides novel compounds, pharmaceutical compositions and methods which may be used in the treatment or prevention of diseases which involve cell adhesion processes, including, but not limited to, rheumatoid arthritis, asthma, allergies, adult respiratory distress syndrome, graft versus host disease, organ transplantation, septic shock, psoriasis, eczema, contact dermatitis, osteoporosis, osteoarthritis, atherosclerosis, metastasis, wound healing, diabetic retinopathy, inflammatory bowel disease and other autoimmune diseases.

Also included in the present invention are pharmaceutical kits comprising one or more containers containing pharmaceutical dosage units comprising a compound of Formula (I), for the treatment of cell adhesion related disorders, including but not limited to thromboembolic disorders.

DETAILED DESCRIPTION OF THE INVENTION

The present invention provides novel nonpeptide compounds of Formula (I) (described below) which bind to integrin receptors thereby altering cell-matrix and cell-cell adhesion processes. The compounds of the present invention are useful for the treatment of thrombosis, inflammation, bone degradation, tumors, metastases, and cell aggregation-related conditions in a mammal.

One aspect of this invention provides compounds of Formula (I) (described below) which are useful as antagonists of the platelet glycoprotein IIb/IIIa complex. The compounds of the present invention inhibit the binding of fibrinogen to the platelet glycoprotein IIb/IIIa complex and inhibit the aggregation of platelets. The present invention also includes pharmaceutical compositions containing such compounds of Formula (I), and methods of using such compounds for the inhibition of platelet aggregation, as thrombolytics, and/or for the treatment of thromboembolic disorders.

[1] This invention relates to novel compounds of the Formula (I):

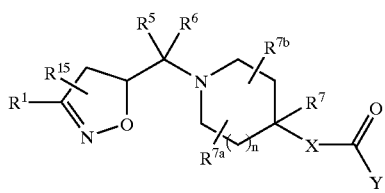

or a pharmaceutically acceptable salt or prodrug form thereof, wherein:

$R^1$ is selected from
$R^{2a}(R^3)N$—V—,
$R^{2a}(R^3)N(CH_2)q$—,
$R^2(R^{2b})N(R^3N=)C$—V—,
$R^2(R^{2b})N(R^3N=)C(CH_2)q$—,
$R^2(R^{2b})N(R^3N=)CNH$—V—,
$R^2(R^{11}O)N(R^3N=)C$—V—,
$R^2(R^{2b})N(R^{11}ON=)C$—V—,

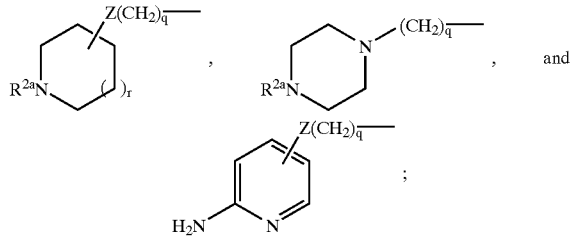

V is selected from:
—($C_1$–$C_4$ alkyl)-,
—($C_2$–$C_4$ alkenyl)-,
—($C_2$–$C_4$ alkynyl)-,
—(phenyl)-, said phenyl substituted with 0–2 groups independently selected from $R^9$,
—(pyridyl)—, said pyridyl substituted with 0–2 groups independently selected from $R^9$, or
—(pyridazinyl)—, said pyridazinyl substituted with 0–2 groups independently selected from $R^9$;

Z is selected from: a bond, O, S, S(=O), and S(=O)$_2$;
$R^{2a}$ is $R^2$ or $R^2(R^{2b})N(R^3N=)C$—;
$R^2$, $R^{2b}$, and $R^3$ are independently selected from:
H,
$C_1$–$C_{10}$ alkyl,
$C_3$–$C_6$ alkenyl,
$C_3$–$C_6$ alkynyl,
$C_3$–$C_{10}$ cycloalkyl,
$C_3$–$C_{10}$ cycloalkyl($C_1$–$C_4$ alkyl)-,
$C_2$–$C_7$ alkylcarbonyl,
$C_1$–$C_4$ haloalkyl,
aryl,
arylcarbonyl,
aryl($C_1$–$C_4$ alkyl)-,
benzhydryl,
benzhydryl ($C_1$–$C_4$ alkyl)-,
heteroaryl,
heteroaryl($C_1$–$C_5$ alkyl)-, and
a cleavable protecting group selected from:
$C_1$–$C_6$ alkoxycarbonyl,
$C_3$–$C_{11}$ cycloalkoxycarbonyl,
$C_7$–$C_{11}$ bicycloalkoxycarbonyl,
aryloxycarbonyl,
aryl ($C_1$–$C_{10}$ alkoxy)carbonyl,
($C_1$–$C_6$ alkyl)carbonyloxy($C_1$–$C_4$ alkoxy)carbonyl,
arylcarbonyloxy($C_1$–$C_4$ alkoxy)carbonyl, and
($C_3$–$C_{11}$ cycloalkyl)carbonyloxy($C_1$–$C_4$ alkoxy)carbonyl, wherein at least one of $R^2$, $R^{2b}$, and $R^3$ is H or a cleavable protecting group;

wherein said aryl groups of $R^2$, $R^{2b}$, and $R^3$ may be substituted with 0–3 groups selected from hydroxy, halogen, $C_1$–$C_6$ alkoxy, $C_1$–$C_6$ alkyl, $CF_3$, —CN, —SO$_2$($C_1$–$C_4$ alkyl), —S($C_1$–$C_4$ alkyl), —NR$^{21}$R$^{22}$, $C_1$–$C_4$ haloalkyl, methylenedioxydiyl, and ethylenedioxydiyl; and said heteroaryl groups of $R^2$, $R^{2b}$, and $R^3$ may be substituted with 0–2 groups selected from hydroxy, halogen, $C_1$–$C_6$ alkoxy, $C_1$–$C_6$ alkyl, $CF_3$, SO$_2$CH$_3$, and —NR$^{21}$R$^{22}$;

alternatively, $R^2$ and $R^{2b}$ can be taken together with the nitrogen atom to which they are attached to form a 5–10 membered heterocyclic ring optionally containing one additional heteroatom selected from: N, O, or S; said heterocyclic ring being monocyclic or bicyclic; said heterocyclic ring being substituted with 0–2 $R^4$;

$R^4$, when a substituent on carbon, is independently selected from:
H, $C_1$–$C_4$ alkyl, aryl, and aryl($C_1$–$C_6$ alkyl)-, wherein said aryl groups may be optionally substituted with 0–3 groups selected from hydroxy, halogen, $C_1$–$C_6$ alkoxy, $C_1$–$C_6$ alkyl, $CF_3$, SCH$_3$, S(O)CH$_3$, SO$_2$CH$_3$, —NR$^{21}$R$^{22}$, $C_1$–$C_4$ haloalkyl, methylenedioxydiyl, and ethylenedioxydiyl;

alternatively, when two $R^4$ groups are attached to adjacent carbon atoms, they may be taken together with the atoms to which they are attached to form a fused 5–7 membered saturated, unsaturated or aromatic carbocyclic ring;

alternatively, when $R^4$ is attached to a saturated carbon atom, it may also be =O or =S;

$R^4$ when a substituent on nitrogen, is independently selected from:
H,
$C_1$–$C_6$ alkyl,
$C_3$–$C_6$ alkenyl,
$C_1$–$C_{10}$ alkoxycarbonyl,
$C_1$–$C_{10}$ alkylcarbonyl,
$C_1$–$C_{10}$ alkylsulfonyl,
$C_3$–$C_{10}$ cycloalkyl,
$C_3$–$C_{10}$ cycloalkyl($C_1$–$C_4$ alkyl)-,
$C_3$–$C_{11}$ cycloalkoxycarbonyl,
$C_7$–$C_{11}$ bicycloalkoxycarbonyl,
aryl,
aryl ($C_1$–$C_{10}$ alkyl)-,
benzhydryl,
benzhydryl ($C_1$–$C_4$ alkyl)-,
arylcarbonyl,
aryloxycarbonyl,
arylsulfonyl,
aryl($C_1$–$C_{10}$ alkyl) sulfonyl,
aryl($C_2$–$C_{10}$ alkenyl)sulfonyl,
aryl($C_1$–$C_{10}$ alkoxy) carbonyl,
heteroaryl,
heteroarylsulfonyl,
heteroarylcarbonyl,
heteroaryl($C_1$–$C_{10}$ alkyl)-, and
heteroaryl($C_1$–$C_{10}$ alkyl)carbonyl, wherein said aryl or heteroaryl groups may be additionally substitututed with 0–2 groups selected from hydroxy, halogen, $C_1$–$C_6$ alkoxy, $C_1$–$C_6$ alkyl, $CF_3$, $SCH_3$, $SOCH_3$, $SO_2CH_3$, or —$NR^{21}R^{22}$;

$R^4$ when a substituent on sulfur, may be =O;

X is —$CH_2CH(W^a)$—, —$CH(W^a)CH_2$—, —$CH(W^a)$—, —$OCH(W^b)$—, —$SCH(W^b)$—, —$NHCH(W^b)$—, —$OCH(W^b)CH_2$—, —$SCH(W^b)CH_2$—, —$NHCH(W^b)CH_2$—, —$OCH_2CH(W^a)$—, —$SCH_2CH(W^a)$—, or —$NHCH_2CH(W^a)$-;

Y is selected from hydroxy,
$C_1$–$C_{10}$ alkyloxy,
$C_3$–$C_{11}$ cycloalkyloxy,
$C_6$–$C_{10}$ aryloxy,
$C_7$–$C_{11}$ arylalkyloxy,
$C_2$–$C_{10}$ alkylcarbonyloxyalkyloxy,
$C_2$–$C_{10}$ alkoxycarbonyloxyalkyloxy,
$C_2$–$C_{10}$ alkoxycarbonylalkyloxy,
$C_4$–$C_{10}$ cycloalkylcarbonyloxyalkyloxy,
$C_4$–$C_{10}$ cycloalkoxycarbonyloxyalkyloxy,
$C_4$–$C_{10}$ cycloalkoxycarbonylalkyloxy,
$C_7$–$C_{11}$ aryloxycarbonylalkyloxy,
$C_7$–$C_{12}$ aryloxycarbonyloxyalkyloxy,
$C_7$–$C_{12}$ arylcarbonyloxyalkyloxy,
$C_4$–$C_{10}$ alkoxyalkylcarbonyloxyalkyloxy,
(5-($C_1$–$C_4$ alkyl)-1,3-dioxa-cyclopenten-2-one-yl) methyloxy, (5-aryl-1,3-dioxa-cyclopenten-2-one-yl) methyloxy, and $(R^{28})(R^{29})N$—($C_1$–$C_{10}$ alkoxy)-;

$W^a$ is selected from:
H,
hydroxy,
—$NR^{16}R^{20}$,
—$NR^{25}R^{26}$,
$C_1$–$C_{10}$ alkoxy,
$C_1$–$C_{10}$ alkyl substituted with 0–3 $R^8$, and
aryl substituted with 0–3 $R^8$, $W^b$ is selected from:
H,
$CH_2OH$,
$CH_2OR^{12}$,
$CH_2CO_2R^{12}$,
$CH_2C(=O)NHR^{18}$,
$CH_2NR^{16}R^{20}$,
$CH_2NR^{25}R^{26}$,
$C_1$–$C_8$ alkyl substituted with 0–2 $R^8$,
$C_3$–$C_6$ alkenyl,
$C_3$–$C_{10}$ cycloalkyl,
$C_4$–$C_{11}$ cycloalkylmethyl,
heteroaryl,
heteroaryl($C_1$–$C_6$ alkyl),
aryl substituted with 0–3 $R^8$, and
aryl($C_1$–$C_6$ alkyl), said aryl substituted with 0–3 $R^8$;

$R^5$ is selected from:
H,
fluoro,
$C_1$–$C_8$ alkyl substituted with 0–2 $R^8$,
$C_3$–$C_6$ alkenyl,
$C_4$–$C_{11}$ cycloalkylmethyl, and
aryl($C_1$–$C_6$ alkyl)-;

$R^6$ is H, methyl, or fluoro;

$R^7$ is selected from:
H,
hydroxy,
$C_1$–$C_4$ alkoxy,
—$C(=O)NHR^{18}$, and
—$NR^{16}R^{20}$;

$R^{7a}$ and $R^{7b}$ are independently selected from H, hydroxy, cyano, fluoro, methyl, and ethyl;

alternatively, when $R^7$ and $R^{7a}$ occur on adjacent carbons $R^7$ and $R^{7a}$ may be taken together to form a carbon-carbon double bond;

alternatively, when $R^{7a}$ and $R^{7b}$ occur on adjacent carbons $R^{7a}$ and $R^{7b}$ may be taken together to form a six carbon aromatic ring;

$R^8$ is selected from:
H,
hydroxy,
cyano,
—$CO_2R^{12}$,
—$C(=O)R^{13}$,
—$OC(=O)R^{13}$,
—$OC(=O)OR^{14}$,
—$OR^{12}$,
—$OCH_2CO_2R^{12}$,
—$CO_2CH_2CO_2R^{12}$,
—$OC(=O)NR^{23}R^{24}$,
—$C(=O)NR^{23}R^{24}$,
—$NR^{25}R^{26}$,
—$NR^{27}C(=O)R^{13}$,
—$NR^{27}C(=O)OR^{14}$,
—$NR^{27}SO_2R^{14}$,
—$SR^{14}$,
—$SOR^{14}$,
—$SO_2R^{14}$,
—$SO_2NR^{23}R^{24}$,
$C_1$–$C_{10}$ alkoxy,
$C_1$–$C_{10}$ alkylcarbonyl,
$C_2$–$C_6$ alkenyl,
$C_3$–$C_{10}$ cycloalkyl,
$C_4$–$C_{11}$ cycloalkylmethyl,
aryl, wherein said aryl is substituted with 0–3 groups selected from halogen, $C_1$–$C_6$ alkoxy, $C_1$–$C_6$ alkyl, halo, $CF_3$, $CO_2R^{12}$, $SO_2Me$, $SOMe$, $SMe$ or —$NMe_2$,
aryl($C_1$–$C_4$ alkyl)-, wherein said aryl is substituted with 0–3 groups selected from halogen, $C_1$–$C_6$ alkoxy, $C_1$–$C_6$ alkyl, $CF_3$, $CO_2R^{12}$, $SO_2Me$, $SOMe$, $SMe$, or —$NMe_2$, and
a 5–10 membered heterocyclic ring containing 1–3 N, O, or S heteroatoms, wherein said heterocyclic ring may be saturated, partially saturated, or fully unsaturated, said heterocyclic ring being substituted with 0–2 groups selected from halogen, $C_1$–$C_6$ alkoxy, $C_1$–$C_6$ alkyl, halo, $CF_3$, $CO_2R^{12}$, $SO_2Me$, $SOMe$, $SMe$ or —$NMe_2$;

$R^9$ is selected from H, halogen, $CF_3$, CN, $C_1$–$C_4$ alkyl, or $C_1$–$C_4$ alkoxy;

$R^{10}$ is selected from:
H,
hydroxy,
CN,
carboxy,
—$NR^{25}R^{26}$;
$C_1$–$C_6$ alkyl,
$C_2$–$C_6$ alkenyl,
$C_2$–$C_6$ alkynyl,
$C_3$–$C_7$ cycloalkyl,
$C_7$–$C_{14}$ bicycloalkyl,
$C_1$–$C_6$ alkoxy,
$C_1$–$C_6$ alkylthio,
$C_1$–$C_6$ alkylsulfinyl,
$C_1$–$C_6$ alkylsulfonyl,
$C_1$–$C_6$ alkylcarbonyl,
$C_1$–$C_6$ alkoxycarbonyl,
aryl, piperidinyl,
morpholinyl, and
pyridinyl;

$R^{11}$ is selected from:
H,
$C_1-C_8$ alkyl,
$C_3-C_6$ alkenyl,
$C_3-C_{11}$ cycloalkyl,
$C_4-C_{11}$ cycloalkylmethyl,
aryl,
aryl($C_1-C_4$ alkyl)-, and
$C_1-C_{10}$ alkyl substituted with 1–2 $R^{10}$;

$R^{12}$ is selected from:
H,
$C_1-C_8$ alkyl,
$C_3-C_6$ alkenyl,
$C_3-C_{11}$ cycloalkyl, $C_4-C_{11}$ cycloalkylmethyl,
aryl,
aryl($C_1-C_4$ alkyl)-, and
$C_1-C_{10}$ alkyl substituted with 1–2 $R^{10}$;

$R^{13}$ is selected from:
hydrogen,
$C_1-C_8$ alkyl,
$C_3-C_6$ alkenyl,
$C_3-C_{11}$ cycloalkyl,
$C_4-C_{11}$ cycloalkylmethyl,
aryl,
aryl($C_1-C_4$ alkyl)-,
heteroaryl,
heteroaryl($C_1-C_4$ alkyl)-, and
$C_1-C_{10}$ alkyl substituted with 1–2 $R^{10}$;

$R^{14}$ is selected from:
$C_1-C_8$ alkyl,
$C_2-C_6$ alkenyl,
$C_3-C_{11}$ cycloalkyl,
$C_4-C_{11}$ cycloalkylmethyl,
aryl,
aryl($C_1-C_4$ alkyl)-, and
$C_1-C_{10}$ alkyl substituted with 1–2 $R^{10}$;

$R^{15}$ is selected from:
H,
OH,
—$OR^{12}$,
—$CO_2R^{12}$,
—$C(=O)NR^{23}R^{24}$,
—$OC(=O) NR^{23}R^{24}$,
$C_1-C_{10}$ alkoxycarbonyl substituted with 0–2 $R^8$;
$C_1-C_{10}$ alkyl substituted with 0–3 $R^8$;
$C_2-C_{10}$ alkenyl substituted with 0–3 $R^8$; and
$C_1-C_{10}$ alkoxy substituted with 0–3 $R^8$;

$R^{16}$ is selected from:
—$C(=O)OR^{17}$,
—$C(=O) R^{18}$,
—$C(=O)NR^{17}R^{18}$,
—$C(=O)NHSO_2R^{17}$,
—$C(=O)NHC(=O)R^{17}$,
—$C(=O)NHC(=O)OR^{17}$,
—$C(=O)NHSO_2NHR^{17}$,
—$SO_2R^{17}$,
—$SO_2NR^{17}R^{18}$, and
—$SO_2NHC(=O) OR^{17}$;

$R^{17}$ is selected from:
$C_1-C_8$ alkyl substituted with 0–2 $R^{19}$,
$C_3-C_8$ alkenyl substituted with 0–2 $R^{19}$,
$C_3-C_8$ alkynyl substituted with 0–2 $R^{19}$,
$C_3-C_8$ cycloalkyl substituted with 0–2 $R^{19}$,
aryl substituted with 0–4 $R^{19}$, aryl($C_1-C_6$ alkyl)-substituted with 0–4 $R^{19}$,
a 5–10 membered heterocyclic ring system having 1–3 heteroatoms selected independently from O, S, and N, said heterocyclic ring being substituted with 0–4 $R^{19}$, and
$C_1-C_6$ alkyl substituted with a 5–10 membered heterocyclic ring system having 1–3 heteroatoms selected independently from O, S, and N, said heterocyclic ring being substituted with 0–4 $R^{19}$;

$R^{18}$ is selected from H or $R^{17}$;

$R^{19}$ is selected from:
H,
halogen,
$CF_3$,
CN,
$NO_2$,
$NR^{25}R^{26}$,
$C_1-C_8$ alkyl,
$C_2-C_6$ alkenyl,
$C_2-C_6$ alkynyl,
$C_3-C_{11}$ cycloalkyl,
$C_3-C_{11}$ cycloalkyl($C_1-C_4$ alkyl)-,
aryl,
aryl($C_1-C_6$ alkyl)-,
$C_1-C_6$ alkoxy, and
$C_1-C_4$ alkoxycarbonyl;

$R^{20}$ is selected from:
H,
$C_1-C_{10}$ alkyl,
$C_2-C_6$ alkenyl,
$C_3-C_{11}$ cycloalkyl,
$C_3-C_{11}$ cycloalkyl ($C_1-C_4$ alkyl)-,
aryl, and
aryl($C_1-C_{10}$ alkyl)—;

$R^{21}$ and $R^{22}$ are each independently H, methyl, ethyl, propyl, or butyl;

$R^{23}$ is selected from:
hydrogen,
$C_1-C_8$ alkyl,
$C_3-C_6$ alkenyl,
$C_3-C_{11}$ cycloalkyl,
$C_4-C_{11}$ cycloalkylmethyl,
hydroxy,
$C_1-C_6$ alkoxy,
benzyloxy,
aryl,
aryl($C_1-C_4$ alkyl)-,
heteroaryl,
heteroaryl($C_1-C_4$ alkyl)-,
adamantylmethyl, and
$C_1-C_{10}$ alkyl substituted with 1–2 $R^{10}$;

$R^{24}$ is selected from:
$C_1-C_8$ alkyl,
$C_2-C_6$ alkenyl,
$C_3-C_{11}$ cycloalkyl,
$C_4-C_{11}$ cycloalkylmethyl,
aryl,
aryl($C_1-C_4$ alkyl)-, and
$C_1-C_{10}$ alkyl substituted with 1–2 $R^{10}$;

$R^{25}$ and $R^{26}$ are, independently, selected from:
H,
$C_1-C_{10}$ alkyl,
$C_1-C_{10}$ alkoxycarbonyl,
$C_1-C_{10}$ alkylcarbonyl,
$C_1-C_{10}$ alkylsulfonyl,
aryl,
aryl($C_1-C_4$ alkyl)-,
arylcarbonyl, aryloxycarbonyl,
arylsulfonyl,
aryl($C_1$–$C_{10}$ alkoxy)carbonyl,
aryl($C_1$–$C_{10}$ alkyl)sulfonyl,
aryl($C_2$–$C_{10}$ alkenyl)sulfonyl,
$C_2$–$C_6$ alkenyl,
$C_3$–$C_{10}$ cycloalkyl,
$C_3$–$C_{10}$ cycloalkyl($C_1$–$C_4$ alkyl)-,
$C_3$–$C_{10}$ cycloalkoxycarbonyl,
$C_7$–$C_{11}$ bicycloalkoxycarbonyl,
heteroaryl,
heteroarylcarbonyl,
heteroarylsulfonyl, and
heteroaryl($C_1$–$C_4$ alkyl)carbonyl,
wherein said aryl groups are optionally substituted with 1–3 substituents selected from the group consisting of: $C_1$–$C_4$ alkyl, $C_1$–$C_4$ alkoxy, halo, $CF_3$, and $NO_2$;

$R^{27}$ is selected from H, methyl, ethyl, propyl, butyl, benzyl, phenethyl, cyclopropyl, and cyclopropylmethyl;

$R^{28}$ and $R^{29}$ are independently selected from:
H, $C_1$–$C_8$ alkyl, $C_3$–$C_6$ alkenyl, $C_3$–$C_{10}$ cycloalkyl ($C_0$–$C_4$ alkyl), aryl, ($C_0$–$C_4$ alkyl), and heteroaryl ($C_0$–$C_4$ alkyl), wherein said aryl or heteroaryl groups are substituted with 0–2 substituents independently selected from $C_1$–$C_4$ alkyl, $C_1$–$C_4$ alkoxy, F, Cl, Br , $CF_3$, and $NO_2$;

n is 0 or 1;
q is 1, 2, 3, or 4;
r is 0, 1, or 2; and
s is 1, 2, 3, or 4.

[2] Preferred compounds of this first embodiment are those of Formula (Ia) wherein:

$R^1$ is selected from
$R^{2a}(R^3)N$—V—, $R^2(R^{2b})N(R^3N=)C$—V—, $R^2(R^{2b})N(R^3N=)CNH$—V—, $R^2(R^{11}O)N(R^3N=)C$—V—, $R^2(R^{2b})N(R^{11}ON=)C$—V—,

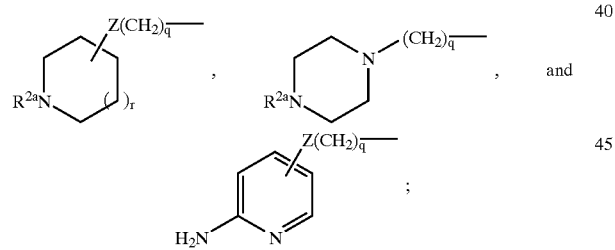
, and

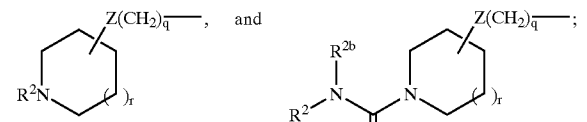
;

V is selected from:
—($C_1$–$C_4$ alkyl)-,
—(phenyl)-, said phenyl substituted with 0–2 groups independently selected from $R^9$,
—(pyridyl)-, said pyridyl substituted with 0–2 groups independently selected from $R^9$, or
—(pyridazinyl)-, said pyridazinyl substituted with 0–2 groups independently selected from $R^9$;

Z is selected from: a bond, O, and $S(=O)_2$;
X is —$CH_2CH(W^a)$—, —$CH(W^a)CH_2$—, —$CH(W^a)$—, —$OCH(W^b)$—, —$SCH(W^b)$—, —$NHCH(W^b)$—, or —$OCH(W^b)CH_2$—;

$W^a$ is selected from:
H, hydroxy, —$NHR^{16}$, —$NR^{25}R^{26}$, $C_1$–$C_{10}$ alkoxy, $C_1$–$C_{10}$ alkyl substituted with 0–3 $R^8$, and aryl substituted with 0–3 $R^8$, $R^6$ is H;

$R^7$ is selected from:
H, hydroxy, methoxy, ethoxy, propoxy, butoxy, —$C(=O)NHR^{18}$, and —$NR^{16}R^{20}$;

$R^{12}$ is selected from H, aryl($C_1$–$C_4$ alkyl)-, and $C_1$–$C_{10}$ alkyl substituted with 1–2 $R^{10}$;

$R^{15}$ is selected from H, OH, —$OR^{12}$, —$CO_2R^{12}$, —$C(=O)NR^{23}R^{24}$, and —$OC(=O) NR^{23}R^{24}$;

$R^{16}$ is selected from —$C(=O)OR^{17}$, —$C(=O)R^{18}$, —$SO_2R^{17}$, and —$SO_2NR^{17}R^{18}$;

$R^{17}$ is selected from:
$C_1$–$C_8$ alkyl substituted with 0–2 $R^{19}$,
$C_3$–$C_8$ alkenyl substituted with 0–2 $R^{19}$,
$C_3$–$C_8$ alkynyl substituted with 0–2 $R^{19}$,
$C_3$–$C_8$ cycloalkyl substituted with 0–2 $R^{19}$,
aryl substituted with 0–4 $R^{19}$,
aryl($C_1$–$C_6$ alkyl)-substituted with 0–4 $R^{19}$,
a 5–10 membered heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzyimdazolyl, piperidinyl, tetrahydrofuranyl, pyranyl, pyrimidinyl, 3H-indolyl, pyrrolidinyl, morpholinyl, and piperazinyl, said heterocyclic ring being substituted with 0–4 $R^{19}$, said heterocyclic ring being substituted with 0–4 $R^{19}$, and
$C_1$–$C_6$ alkyl substituted with a 5–10 membered heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzyimdazolyl, piperidinyl, tetrahydrofuranyl, pyranyl, pyrimidinyl, 3H-indolyl, pyrrolidinyl, morpholinyl, or piperazinyl, said heterocyclic ring being substituted with 0–4 $R^{19}$;

$R^{18}$ is selected from H or $C_1$–$C_5$ alkyl;
n is 0 or 1;
q is 1, 2, 3, or 4;
r is 0, 1, or 2; and
s is 1, 2, 3, or 4.

[3] More preferred compounds of this first embodiment are those of Formula (Ia)

(Ia)

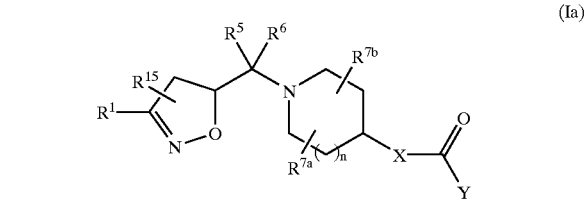

wherein:
$R^1$ is selected from $R^2(R^{2b})N(R^3N=)C$—V—, $R^2(R^{2b})N(R^3N=)CNH$—V—,

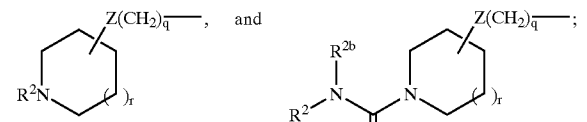

V is selected from:
—($C_1$–$C_4$ alkyl)-,
—(pyridyl)-, and

—(phenyl)-, said phenyl substituted with 0–2 groups independently selected from F, Br, methyl, and methoxy;

Z is a bond or O;

$R^2$, $R^{2b}$, and $R^3$ are independently selected from:
H, $C_1$–$C_8$ alkyl, $C_3$–$C_6$ alkenyl, $C_3$–$C_6$ alkynyl, $C_3$–$C_8$ cycloalkyl, $C_3$–$C_8$ cycloalkyl($C_1$–$C_4$ alkyl)-, $C_2$–$C_7$ alkylcarbonyl, $C_1$–$C_4$ haloalkyl, aryl, arylcarbonyl, aryl($C_1$–$C_4$ alkyl)-, benzhydryl, benzhydryl($C_1$–$C_4$ alkyl)-, heteroaryl, heteroaryl($C_1$–$C_4$ alkyl)-, and
a cleavable protecting group selected from:
$C_1$–$C_6$ alkoxycarbonyl,
$C_3$–$C$ cycloalkoxycarbonyl,
$C_7$–$C_{11}$ bicycloalkoxycarbonyl,
aryloxycarbonyl,
aryl($C_1$–$C_8$ alkoxy) carbonyl,
($C_1$–$C_6$ alkyl)carbonyloxy($C_1$–$C_4$ alkoxy) carbonyl,
arylcarbonyloxy($C_1$–$C_4$ alkoxy)carbonyl, and
($C_3$–$C_8$ cycloalkyl)carbonyloxy($C_1$–$C_4$ alkoxy) carbonyl,
wherein at least one of $R^2$, $R^{2b}$, and $R^3$ is H or a cleavable protecting group;
wherein said aryl groups of $R^2$, $R^{2b}$, and $R^3$ may be substituted with 0–3 groups selected from hydroxy, halogen, $C_1$–$C_6$ alkoxy, $C_1$–$C_6$ alkyl, $CF_3$, —CN, —$SO_2$($C_1$–$C_4$ alkyl), —S($C_1$–$C_4$ alkyl), —$NR^{21}R^{22}$, $C_1$–$C_4$ haloalkyl, methylenedioxydiyl, and ethylenedioxydiyl; and
said heteroaryl groups of $R^2$, $R^{2b}$, and $R^3$ may be substituted with 0–2 groups selected from hydroxy, halogen, $C_1$–$C_6$ alkoxy, $C_1$–$C_6$ alkyl, $CF_3$, $SO_2CH_3$, and —$NR^{21}R^{22}$;
alternatively, $R^2$ and $R^{2b}$ can be taken together with the nitrogen atom to which they are attached to form a 5–10 membered heterocyclic ring system selected from morpholine, piperidine, piperazine, pyrrolidine, tetrahydroisoquinoline, thiazolidine, thiomorpholine, 1,4-benzoxazine, 8-oxo-3-azabicyclo[3.2.1]octane, 1,4-dioxa-8-azaspiro[4.5]decane, or azepine, said heterocyclic ring being substituted with 0–2 $R^4$;

X is —$CH_2CH(W^a)$—, —$CH(W^a)CH_2$—, —$CH(W^a)$—, or —$OCH(W^b)$—;

Y is selected from hydroxy,
$C_1$–$C_6$ alkoxy;
methylcarbonyloxymethoxy-;
ethylcarbonyloxymethoxy-;
t-butylcarbonyloxymethoxy-;
cyclohexylcarbonyloxymethoxy-;
1-(methylcarbonyloxy)ethoxy-;
1-(ethylcarbonyloxy)ethoxy-;
1-(t-butylcarbonyloxy)ethoxy-;
1-(cyclohexylcarbonyloxy)ethoxy-;
i-propyloxycarbonyloxymethoxy-;
t-butyloxycarbonyloxymethoxy-;
1-(i-propyloxycarbonyloxy)ethoxy-;
1-(cyclohexyloxycarbonyloxy)ethoxy-;
1-(t-butyloxycarbonyloxy)ethoxy-;
dimethylaminoethoxy-;
diethylaminoethoxy-;
(5-methyl-1,3-dioxacyclopenten-2-on-4-yl)methoxy-;
(5-(t-butyl)-1,3-dioxacyclopenten-2-on-4-yl)methoxy-;
(1,3-dioxa-5-phenyl-cyclopenten-2-on-4-yl)methoxy-;
1-(2-(2-methoxypropyl)carbonyloxy)ethoxy-;

$W^a$ is H or —$NHR^{16}$;

$W^b$ is H, methyl, ethyl, benzyl, phenethyl, pyridyl, pyridylmethyl, pyridylethyl, (indol-3-yl)ethyl, $CH_2C(=O)NHR^{18}$, and $CH_2NHR^{16}$;

$R^8$ is selected from:
H, hydroxy, cyano, —$Co_2R^{12}$, —$C(=O)R^{13}$, —$C(=O)NR^{23}R^{24}$, —$NR^{25}R^{26}$, —$SR^{14}$, —$SOR^{14}$, —$SO_2R^{14}$, $C_1$–$C_{10}$ alkoxy, $C_1$–$C_{10}$ alkylcarbonyl,
aryl, wherein said aryl is substituted with 0–3 groups selected from halogen, $C_1$–$C_6$ alkoxy, $C_1$–$C_6$ alkyl, halo, $CF_3$, $CO_2R^{12}$, $SO_2Me$, SOMe, SMe or —$NMe_2$,
a 5–10 membered heterocyclic ring system selected from pyridinyl, furanyl, thiazolyl, thienyl, pyrrolyl, pyrazolyl, triazolyl, imidazolyl, benzofuranyl, indolyl, inolinyl, quinolinyl, isoquinolinyl, benzimidazolyl, piperidinyl, tetrahydrofuranyl, pyranyl, 3H-indolyl, pyrrolidinyl, piperidinyl, isoxazolinyl, isoxazolyl or morpholinyl;

$R^{15}$ is selected from H, OH, —$OR^{12}$, and —$OC(=O)NR^{23}R^{24}$;

$R^{16}$ is —$C(=O)OR^{17}$ or —$SO_2R^{17}$;

$R^{17}$ is selected from:
$C_1$–$C_8$ alkyl,
$C_2$–$C_8$ alkenyl,
aryl substituted with 0–4 $R^{19}$,
aryl($C_1$–$C_6$ alkyl)-substituted with 0–4 $R^{19}$,
a 5–10 membered heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzyimdazolyl, piperidinyl, tetrahydrofuranyl, pyranyl, pyrimidinyl, 3H-indolyl, pyrrolidinyl, morpholinyl, and piperazinyl, said heterocyclic ring being substituted with 0–4 $R^{19}$, said heterocyclic ring being substituted with 0–4 $R^{19}$, and
$C_1$–$C_6$ alkyl substituted with a 5–10 membered heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzyimdazolyl, piperidinyl, tetrahydrofuranyl, pyranyl, pyrimidinyl, 3H-indolyl, pyrrolidinyl, morpholinyl, or piperazinyl, said heterocyclic ring being substituted with 0–4 $R^{19}$;

$R^{19}$ is selected from H, halogen, $CF_3$, CN, $NO_2$, $NR^{25}R^{26}$, $C_1$–$C_8$ alkyl, $C_2$–$C_6$ alkenyl, $C_2$–$C_6$ alkynyl, $C_3$–$C_{11}$ cycloalkyl, $C_3$–$C_{11}$ cycloalkyl ($C_1$–$C_4$ alkyl)-, aryl, aryl($C_1$–$C_6$ alkyl)-, $C_1$–$C_6$ alkoxy, and $C_1$–$C_4$ alkoxycarbonyl;

n is 0 or 1;
q is 1, 2, 3, or 4;
r is 0, 1, or 2; and
s is 1, 2, 3, or 4.

[4] Even more preferred compounds of this first embodiment are compounds of Formula (Ia) wherein:
$R^1$ is $R^2(R^{2b})N(R^3N=)C$—V— or $R^2(R^{2b})N(R^3N=)CNH$—V—;
V is -(pyridyl)- or -(phenyl)-, said phenyl substituted with 0–2 groups independently selected from F, Br, methyl, and methoxy;
Z is a bond or O;
$R^2$, $R^{2b}$, and $R^3$ are independently selected from:

H, $C_1$–$C_6$ alkyl, $C_3$–$C_6$ alkenyl, $C_3$–$C_6$ alkynyl, $C_3$–$C_8$ cycloalkyl, $C_3$–$C_8$ cycloalkyl($C_1$–$C_4$ alkyl)-, $C_2$–$C_7$ alkylcarbonyl, $C_1$–$C_4$ haloalkyl, arylcarbonyl, aryl($C_1$–$C_4$ alkyl)-, benzhydryl, heteroaryl, heteroaryl($C_1$–$C_4$ alkyl)-, and a cleavable protecting group selected from:
- $C_1$–$C_4$ alkoxycarbonyl,
- $C_3$–$C_6$ cycloalkoxycarbonyl,
- $C_7$–$C_{11}$ bicycloalkoxycarbonyl,
- aryl($C_1$–$C_8$ alkoxy)carbonyl,
- ($C_1$–$C_6$ alkyl)carbonyloxy($C_1$–$C_4$ alkoxy)carbonyl,
- arylcarbonyloxy($C_1$–$C_4$ alkoxy)carbonyl, and
- ($C_3$–$C_8$ cycloalkyl)carbonyloxy($C_1$–$C_4$ alkoxy)carbonyl, wherein at least one of $R^2$, $R^{2b}$, and $R^3$ is H or a cleavable protecting group;

wherein said aryl groups of $R^2$, $R^{2b}$, and $R^3$ may be substituted with 0–3 groups selected from hydroxy, halogen, methoxy, ethoxy, propoxy, butoxy, methyl, ethyl, propyl, butyl, $CF_3$, —CN, —$SO_2(CH_3)$, —$SO_2(C_2H_5)$, —$SO_2$ ($C_3H_7$), —$SO_2$ ($C_4H_9$), —$NR^{21}R^{22}$, $C_1$–$C_4$ haloalkyl, methylenedioxydiyl, and ethylenedioxydiyl; and said heteroaryl groups of $R^2$, $R^{2b}$, and $R^3$ may be substituted with 0–2 groups selected from hydroxy, halogen, methoxy, ethoxy, propoxy, butoxy, methyl, ethyl, propyl, butyl, $CF_3$, $SO_2CH_3$, and —$NR^{21}R^{22}$;

alternatively, $R^2$ and $R^{2b}$ can be taken together with the nitrogen atom to which they are attached to form a 5–10 membered heterocyclic ring system selected from morpholine, piperidine, piperazine, pyrrolidine, tetrahydroisoquinoline, thiazolidine, thiomorpholine, 1,4-benzoxazine, 8-oxo-3-azabicyclo[3.2.1]octane, 1,4-dioxa-8-azaspiro[4.5]decane, or azepine, said heterocyclic ring being substituted with 0–2 $R^4$;

$R^4$, when a substituent on carbon, is independently selected from H, methyl, ethyl, propyl, butyl, and phenyl; wherein said phenyl groups may be optionally substituted with 0–3 groups selected from hydroxy, halogen, methoxy, methyl, ethyl, CF3, $SCH_3$, —$NH_2$, —$NH(CH_3)$, —$N(CH_3)_2$, methylenedioxydiyl, and ethylenedioxydiyl;

alternatively, when two $R^4$ groups are attached to adjacent carbon atoms, they may be taken together with the atoms to which they are attached to form a fused 5–7 membered saturated, unsaturated or aromatic carbocyclic ring;

alternatively, when $R^4$ is attached to a saturated carbon atom, it may also be =O or =S;

$R^4$ when a substituent on nitrogen, is independently selected from H, methyl, ethyl, propyl, butyl, cyclopropyl, cyclopropylmethyl, phenyl, phenylmethyl, phenylethyl, pyridyl, pyridylmethyl wherein said phenyl or pyridyl groups may be additionally substitututed with 0–2 groups selected from hydroxy, halogen, methoxy, methyl, ethyl, $CF_3$, $SCH_3$, —$NH_2$, —$NH(CH_3)$, and —$N(CH_3)_2$;

$R^4$ when a substituent on sulfur, may be =O;

X is —$CH_2CH(W^a)$—, —$CH(W^a)$—, or —$OCH(W^b)$—;

Y is selected from hydroxy; methoxy; ethoxy; isopropoxy; n-butyloxy; isobutyloxy; t-butoxy; benzyloxy; methylcarbonyloxymethoxy-; ethylcarbonyloxymethoxy-; t-butylcarbonyloxymethoxy-; cyclohexylcarbonyloxymethoxy-;
1-(methylcarbonyloxy)ethoxy-;
1-(ethylcarbonyloxy)ethoxy-;
1-(t-butylcarbonyloxy)ethoxy-;
1-(cyclohexylcarbonyloxy)ethoxy-;
i-propyloxycarbonyloxymethoxy-;
t-butyloxycarbonyloxymethoxy-;
1-(i-propyloxycarbonyloxy)ethoxy-;
1-(cyclohexyloxycarbonyloxy)ethoxy-;
1-(t-butyloxycarbonyloxy)ethoxy-;
dimethylaminoethoxy-;
diethylaminoethoxy-;
(5-methyl-1,3-dioxacyclopenten-2-on-4-yl)methoxy;
(5-(t-butyl)-1,3-dioxacyclopenten-2-on-4-yl) methoxy-;
(1,3-dioxa-5-phenyl-cyclopenten-2-on-4-yl)methoxy-;
1-(2-(2-methoxypropyl)carbonyloxy)ethoxy-;

$W^a$ is H or —$NHR^{16}$;

$W^b$ is H, methyl, ethyl, benzyl, phenethyl, pyridyl, pyridylmethyl, pyridylethyl, (indol-3-yl)ethyl, $CH_2C(=O)NHR^{18}$, and $CH_2NHR^{16}$;

$R^8$ is selected from:
H, hydroxy, cyano, —$CO_2R^{12}$, —$C(=O)R^{13}$, —$C(=O)NR^{23}R^{24}$, —$NR^{25}R^{26}$, —$SR^{14}$, —$SOR^{14}$, —$SO_2R^{14}$, $C_1$–$C_4$ alkoxy, $C_1$–$C_4$ alkylcarbonyl,
aryl, wherein said aryl is substituted with 0–3 groups selected from halogen, methoxy, ethoxy, propoxy, butoxy, methyl, ethyl, propyl, butyl, $CF_3$, $CO_2R^{12}$, $SO_2Me$, $SOMe$, $SMe$ or —$NMe_2$,
a 5–10 membered heterocyclic ring system selected from pyridinyl, furanyl, thiazolyl, thienyl, pyrrolyl, pyrazolyl, triazolyl, imidazolyl, benzofuranyl, indolyl, inolinyl, quinolinyl, isoquinolinyl, benzimidazolyl, piperidinyl, tetrahydrofuranyl, pyranyl, 3H-indolyl, pyrrolidinyl, piperidinyl, isoxazolinyl, isoxazolyl or morpholinyl;

$R^{15}$ is H;

$R^{16}$ is —$SO_2R^{17}$, —$C(=O)OCH_2CH_2CH_2CH_3$, —$C(=O)OCH_2CH(CH_3)_2$ or —$C(=O)OCH_2(C_6H_5)$;

$R^{17}$ is selected from:
$C_1$–$C_8$ alkyl,
aryl substituted with 0–2 $R^{19}$,
aryl($C_1$–$C_6$ alkyl)-substituted with 0–2 $R^{19}$,
a 5–10 membered heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzyimdazolyl, piperidinyl, tetrahydrofuranyl, pyranyl, pyrimidinyl, 3H-indolyl, pyrrolidinyl, morpholinyl, and piperazinyl, said heterocyclic ring being substituted with 0–2 $R^{19}$ said heterocyclic ring being substituted with 0–2 $R^{19}$, and
$C_1$–$C_6$ alkyl substituted with a 5–10 membered heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzyimdazolyl, piperidinyl, tetrahydrofuranyl, pyranyl, pyrimidinyl, 3H-indolyl, pyrrolidinyl, morpholinyl, or piperazinyl, said heterocyclic ring being substituted with 0–2 $R^{19}$;

$R^{19}$ is selected from:
  H, halogen, $CF_3$, CN, $NO_2$, $NR^{25}R^{26}$, $C_1$–$C_4$ alkyl, $C_2$–$C_4$ alkenyl, $C_2$–$C_4$ alkynyl, $C_3$–$C_6$ cycloalkyl, $C_3$–$C_6$ cycloalkyl($C_1$–$C_4$ alkyl)-, aryl, aryl($C_1$–$C_4$ alkyl)-, $C_1$–$C_4$ alkoxy, and $C_1$–$C_4$ alkoxycarbonyl;
n is 1; and
s is 1 or 2.

[5] Specifically preferred compounds of this first embodiment are compounds, or pharmaceutically acceptable salt or prodrug forms thereof, selected from:

[[1-[3-[4-(aminoiminomethyl)phenyl]isoxazolin-5-ylmethyl]-4-piperidinyl]oxy]acetic acid;

[[1-[3-[4-[(n-butylamino)iminomethyl]phenyl]isoxazolin-5-ylmethyl]-4-piperidinyl]oxy]acetic acid;

[[1-[3-[4-[(2-phenylethylamino)iminomethyl]phenyl]-isoxazolin-5-ylmethyl]-4-piperidinyl]oxy]acetic acid;

[[1-[3-[4-[(phenylmethylamino)iminomethyl]phenyl]-isoxazolin-5-ylmethyl]-4-piperidinyl]oxy]acetic acid;

[[1-[3-[4-[(n-propylamino)iminomethyl]phenyl]isoxazolin-5-ylmethyl]-4-piperidinyl]oxy]acetic acid;

[[1-[3-[4-[(ethylamino)iminomethyl]phenyl]isoxazolin-5-ylmethyl]-4-piperidinyl]oxy]acetic acid;

[[1-[3-[4-[(morpholino)iminomethyl]phenyl]isoxazolin-5-ylmethyl]-4-piperidinyl]oxy]acetic acid;

[[1-[3-[4-[(piperidino)iminomethyl]phenyl]isoxazolin-5-ylmethyl]-4-piperidinyl]oxy]acetic acid;

[[1-[3-[4-[(thiazolidino)iminomethyl]phenyl]isoxazolin-5-ylmethyl]-4-piperidinyl]oxy]acetic acid;

[[1-[3-[4-[(2,6-dimethylmorpholino)iminomethyl]phenyl]-isoxazolin-5-ylmethyl]-4-piperidinyl]oxy]acetic acid;

[[1-[3-[4-[(4-methylpiperazino)iminomethyl]phenyl]-isoxazolin-5-ylmethyl]-4-piperidinyl]oxy]acetic acid;

[[1-[3-[4-[(4-phenylpiperazino)iminomethyl]phenyl]-isoxazolin-5-ylmethyl]-4-piperidinyl]oxy]acetic acid;

[[1-[3-[4-[(pyrrolidino)iminomethyl]phenyl]isoxazolin-5-ylmethyl]-4-piperidinyl]oxy]acetic acid;

[[1-[3-[4-[(2,6-dimethylpiperazino)iminomethyl]phenyl]-isoxazolin-5-ylmethyl]-4-piperidinyl]oxy]acetic acid;

[[1-[3-[4-[(2-fluorophenyl)piperazino)iminomethyl]phenyl]-isoxazolin-5-ylmethyl]-4-piperidinyl]oxy]acetic acid;

[[1-[3-[4-[(2-methylphenyl)piperazino)iminomethyl]phenyl]-isoxazolin-5-ylmethyl]-4-piperidinyl]oxy]acetic acid;

[[1-[3-[4-[(thiomorpholino)iminomethyl]phenyl]isoxazolin-5-ylmethyl]-4-piperidinyl]oxy]acetic acid;

[[1-[3-[4-[(4-pyridylethylamino)iminomethyl]phenyl]-isoxazolin-5-ylmethyl]-4-piperidinyl]oxy]acetic acid;

[[1-[3-[4-[(4-propylpiperazino)iminomethyl]phenyl]-isoxazolin-5-ylmethyl]-4-piperidinyl]oxy]acetic acid;

[[1-[3-[4-[(1,2,3,4-tetrahydroisoquinolino)iminomethyl]-phenyl]isoxazolin-5-ylmethyl]-4-piperidinyl]oxy]acetic acid;

[[1-[3-[4-[(1,2,3,4-tetrahydro-2,7-naphthyridino)iminomethyl]phenyl]isoxazolin-5-ylmethyl]-4-piperidinyl]oxy]-acetic acid;

[1-[3-[4-(aminoiminomethyl)phenyl]isoxazolin-5-ylmethyl]-4-piperidinyl]acetic acid;

[1-[3-[4-[(n-butylamino)iminomethyl]phenyl]isoxazolin-5-ylmethyl]-4-piperidinyl]acetic acid;

[1-[3-[4-[(2-phenylethylamino)iminomethyl]phenyl]-isoxazolin-5-ylmethyl]-4-piperidinyl]acetic acid;

[1-[3-[4-[(phenylmethylamino)iminomethyl]phenyl]-isoxazolin-5-ylmethyl]-4-piperidinyl]acetic acid;

[1-[3-[4-[(n-propylamino)iminomethyl]phenyl]isoxazolin-5-ylmethyl]-4-piperidinyl]acetic acid;

[1-[3-[4-[(ethylamino)iminomethyl]phenyl]isoxazolin-5-ylmethyl]-4-piperidinyl]acetic acid;

[1-[3-[4-[(morpholino)iminomethyl]phenyl]isoxazolin-5-ylmethyl]-4-piperidinyl]acetic acid;

[1-[3-[4-[(piperidino)iminomethyl]phenyl]isoxazolin-5-ylmethyl]-4-piperidinyl]acetic acid;

[1-[3-[4-[(thiazolidino)iminomethyl]phenyl]isoxazolin-5-ylmethyl]-4-piperidinyl]acetic acid;

[1-[3-[4-[(2,6-dimethylmorpholino)iminomethyl]phenyl]isoxazolin-5-ylmethyl]-4-piperidinyl]acetic acid;

[1-[3-[4-[(4-methylpiperazino)iminomethyl]phenyl]isoxazolin-5-ylmethyl]-4-piperidinyl]acetic acid;

[1-[3-[4-[(4-phenylpiperazino)iminomethyl]phenyl]isoxazolin-5-ylmethyl]-4-piperidinyl]acetic acid;

[1-[3-[4-[(pyrrolidino)iminomethyl]phenyl]isoxazolin-5-ylmethyl]-4-piperidinyl]acetic acid;

[1-[3-[4-[(2,6-dimethylpiperazino)iminomethyl]phenyl]isoxazolin-5-ylmethyl]-4-piperidinyl]acetic acid;

[1-[3-[4-[(2-fluorophenyl)piperazino)iminomethyl]phenyl]isoxazolin-5-ylmethyl]-4-piperidinyl]acetic acid;

[1-[3-[4-[(2-methylphenyl)piperazino)iminomethyl]phenyl]isoxazolin-5-ylmethyl]-4-piperidinyl]acetic acid;

[1-[3-[4-[(thiomorpholino)iminomethyl]phenyl]isoxazolin-5-ylmethyl]-4-piperidinyl]acetic acid;

[1-[3-[4-[(4-pyridylethylamino)iminomethyl]phenyl]-isoxazolin-5-ylmethyl]-4-piperidinyl]acetic acid;

[1-[3-[4-[(4-propylpiperazino)iminomethyl]phenyl]-isoxazolin-5-ylmethyl]-4-piperidinyl]acetic acid;

[1-[3-[4-[(1,2,3,4-tetrahydroisoquinolino)iminomethyl]-phenyl]isoxazolin-5-ylmethyl]-4-piperidinyl]acetic acid; and

[1-[3-[4-[(1,2,3,4-tetrahydro-2,7-naphthyridino)iminomethyl]phenyl]isoxazolin-5-ylmethyl]-4-piperidinyl]-acetic acid.

[8] A second embodiment of this invention provides a compound of Formula (I):

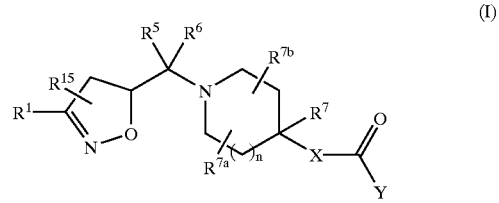

or a pharmaceutically acceptable salt or prodrug form thereof wherein:

$R^1$ is selected from
  $R^{2a}(R^3)N$—V—,
  $R^{2a}(R^3)N(CH_2)_q$—,
  $R^2(R^{2b})N(R^3N{=})C$—V—,
  $R^2(R^{2b})N(R^3N{=})C(CH_2)_q$—,
  $R^2(R^{2b})N(R^3N{=})CNH$—V—,
  $R^2(R^{11}O)N(R^3N{=})C$—V—, $R^2(R^{2b})N(R^{11}ON=)C-V-$,

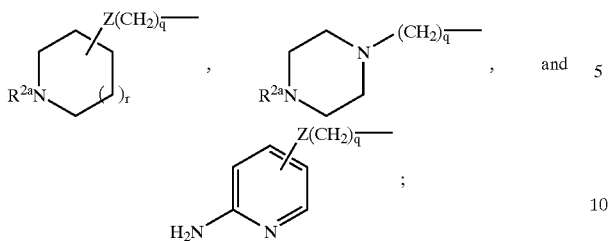, and

V is selected from:
—($C_1$–$C_4$ alkyl)-,
—($C_2$–$C_4$ alkenyl)-,
—($C_2$–$C_4$ alkynyl)-,
—(phenyl)-, said phenyl substituted with 0–2 groups independently selected from $R^9$,
—(pyridyl)-, said pyridyl substituted with 0–2 groups independently selected from $R^9$, or
—(pyridazinyl)-, said pyridazinyl substituted with 0–2 groups independently selected from $R^9$;

Z is selected from: a bond, O, S, S(=O), and S(=O)$_2$;
$R^{2a}$ is $R^2$ or $R^2(R^{2b})N(R^3N=)C-$;
$R^2$, $R^{2b}$, and $R^3$ are independently selected from:
H, $C_1$–$C_{10}$ alkyl, $C_3$–$C_6$ alkenyl, $C_3$–$C_6$ alkynyl, $C_3$–$C_{10}$ cycloalkyl, $C_3$–$C_{10}$ cycloalkyl($C_1$–$C_4$ alkyl)-, $C_2$–$C_7$ alkylcarbonyl, $C_1$–$C_4$ haloalkyl, aryl, arylcarbonyl, aryl($C_1$–$C_4$ alkyl)-, benzhydryl, benzhydryl ($C_1$–$C_4$ alkyl)-, heteroaryl, heteroaryl($C_1$–$C_5$ alkyl)-, and
a cleavable protecting group selected from:
$C_1$–$C_6$ alkoxycarbonyl,
$C_3$–$C_{11}$ cycloalkoxycarbonyl,
$C_7$–$C_{11}$ bicycloalkoxycarbonyl, aryloxycarbonyl, aryl($C_1$–$C_{10}$ alkoxy) carbonyl,
($C_1$–$C_6$ alkyl)carbonyloxy($C_1$–$C_4$ alkoxy) carbonyl,
arylcarbonyloxy($C_1$–$C_4$ alkoxy)carbonyl, and
($C_3$–$C_{11}$ cycloalkyl)carbonyloxy($C_1$–$C_4$ alkoxy) carbonyl,
wherein at least one of $R^2$, $R^{2b}$, and $R^3$ is H or a cleavable protecting group;
wherein said aryl groups of $R^2$, $R^{2b}$, and $R^3$ may be substituted with 0–3 groups selected from hydroxy, halogen, $C_1$–$C_6$ alkoxy, $C_1$–$C_6$ alkyl, $CF_3$, —CN, —SO$_2$($C_1$–$C_4$ alkyl), —S($C_1$–$C_4$ alkyl), —NR$^{21}$R$^{22}$, $C_1$–$C_4$ haloalkyl, methylenedioxydiyl, and ethylenedioxydiyl; and
said heteroaryl groups of $R^2$, $R^{2b}$, and $R^3$ may be substituted with 0–2 groups selected from hydroxy, halogen, $C_1$–$C_6$ alkoxy, $C_1$–$C_6$ alkyl, $CF_3$, $SO_2CH_3$, and —NR$^{21}$R$^{22}$;
alternatively, $R^2$ and $R^{2b}$ can be taken together with the nitrogen atom to which they are attached to form a 5–10 membered heterocyclic ring optionally containing one additional heteroatom selected from: N, O, or S; said heterocyclic ring being monocyclic or bicyclic; said heterocyclic ring being substituted with 0–2 $R^4$;
$R^4$, when a substituent on carbon, is independently selected from:
H, $C_1$–$C_4$ alkyl, aryl, and aryl($C_1$–$C_6$ alkyl)-, wherein said aryl groups may be optionally substituted with 0–3 groups selected from hydroxy, halogen, $C_1$–$C_6$ alkoxy, $C_1$–$C_6$ alkyl, $CF_3$, $SCH_3$, $S(O)CH_3$, $SO_2CH_3$, —NR$^{21}$R$^{22}$, $C_1$–$C_4$ haloalkyl, methylenedioxydiyl, and ethylenedioxydiyl;

alternatively, when two $R^4$ groups are attached to adjacent carbon atoms, they may be taken together with the atoms to which they are attached to form a fused 5–7 membered saturated, unsaturated or aromatic carbocyclic ring;
alternatively, when $R^4$ is attached to a saturated carbon atom, it may also be =O or =S;
$R^4$ when a substituent on nitrogen, is independently selected from:
H, $C_1$–$C_6$ alkyl, $C_3$–$C_6$ alkenyl, $C_1$–$C_{10}$ alkoxycarbonyl, $C_1$–$C_{10}$ alkylcarbonyl, $C_1$–$C_{10}$ alkylsulfonyl, $C_3$–$C_{10}$ cycloalkyl, $C_3$–$C_{10}$ cycloalkyl ($C_1$–$C_4$ alkyl)-, $C_3$–$C_{11}$ cycloalkoxycarbonyl, $C_7$–$C_{11}$ bicycloalkoxycarbonyl, aryl, aryl($C_1$–$C_{10}$ alkyl)-, benzhydryl, benzhydryl ($C_1$–$C_4$ alkyl)-, arylcarbonyl, aryloxycarbonyl, arylsulfonyl, aryl ($C_1$–$C_{10}$ alkyl)sulfonyl, aryl($C_2$–$C_{10}$ alkenyl) sulfonyl, aryl($C_1$–$C_{10}$ alkoxy)carbonyl, heteroaryl, heteroarylsulfonyl, heteroarylcarbonyl, heteroaryl($C_1$–$C_{10}$ alkyl)-, and heteroaryl($C_1$–$C_{10}$ alkyl)carbonyl,
wherein said aryl or heteroaryl groups may be additionally substitututed with 0–2 groups selected from hydroxy, halogen, $C_1$–$C_6$ alkoxy, $C_1$–$C_6$ alkyl, $CF_3$, $SCH_3$, $SOCH_3$, $SO_2CH_3$, or —NR$^{21}$R$^{22}$;
$R^4$ when a substituent on sulfur, may be =O;
X is —OCH$_2$CH(W$^a$)—, —SCH$_2$CH(W$^a$)—, —NHCH$_2$CH(W$^a$)—, —OCH(W$^b$)—, —SCH(W$^b$)—, —NHCH(W$^b$)—, —OCH(W$^b$)CH$_2$—, —SCH(W$^b$) CH$_2$—, or —NHCH(W$^b$)CH$_2$—;
Y is selected from hydroxy,
$C_1$–$C_{10}$ alkyloxy,
$C_3$–$C_{11}$ cycloalkyloxy,
$C_6$–$C_{10}$ aryloxy,
$C_7$–$C_{11}$ arylalkyloxy,
$C_2$–$C_{10}$ alkylcarbonyloxyalkyloxy,
$C_2$–$C_{10}$ alkoxycarbonyloxyalkyloxy,
$C_2$–$C_{10}$ alkoxycarbonylalkyloxy,
$C_4$–$C_{10}$ cycloalkylcarbonyloxyalkyloxy,
$C_4$–$C_{10}$ cycloalkoxycarbonyloxyalkyloxy,
$C_4$–$C_{10}$ cycloalkoxycarbonylalkyloxy,
$C_7$–$C_{11}$ aryloxycarbonylalkyloxy,
$C_7$–$C_{12}$ aryloxycarbonyloxyalkyloxy,
$C_7$–$C_{12}$ arylcarbonyloxyalkyloxy,
$C_4$–$C_{10}$ alkoxyalkylcarbonyloxyalkyloxy,
(5-($C_1$–$C_4$ alkyl)-1,3-dioxa-cyclopenten-2-one-yl) methyloxy,
(5-aryl-1,3-dioxa-cyclopenten-2-one-yl)methyloxy, and
(R$^{28}$) (R$^{29}$) N—($C_1$–$C_{10}$ alkoxy)-; p2 W$^a$ is selected from:
H,
hydroxy,
—NR$^{16}$R$^{20}$,
—NR$^{25}$R$^{26}$,
$C_1$–$C_{10}$ alkoxy,
$C_1$–$C_{10}$ alkyl substituted with 0–3 $R^8$, and
aryl substituted with 0–3 $R^8$,
W$^b$ is selected from:
H,
CH$_2$OH,
CH$_2$OR$^{12}$,
CH$_2$CO$_2$R$^{12}$,
CH$_2$C(=O)NHR$^{18}$,
CH$_2$NR$^{16}$R$^{20}$,
CH$_2$NR$^{25}$R$^{26}$, C$_1$–C$_8$ alkyl substituted with 0–2 R$^8$,
C$_3$–C$_6$ alkenyl,
C$_3$–C$_{10}$ cycloalkyl,
C$_4$–C$_{11}$ cycloalkylmethyl,
heteroaryl,
heteroaryl(C$_1$–C$_6$ alkyl),
aryl substituted with 0–3 R$^8$, and
aryl(C$_1$–C$_6$ alkyl), said aryl substituted with 0–3 R$^8$;

R$^5$ and R$^6$ are taken together to be C=O;

R$^7$ is H or C$_1$–C$_4$ alkyl substituted with 0–3 R$^8$;

R$^{7a}$ and R$^{7b}$ are independently selected from H, methyl, and ethyl;

alternatively, when R$^7$ and R$^{7a}$ occur on adjacent carbons R$^7$ and R$^{7a}$ may be taken together to form a carbon-carbon double bond;

alternatively, when R$^{7a}$ and R$^{7b}$ occur on adjacent carbons R$^{7a}$ and R$^{7b}$ may be taken together to form a six carbon aromatic ring;

R$^8$ is selected from:
H, hydroxy, cyano, —CO$_2$R$^{12}$, —C(=O)R$^{13}$, —OC(=O)R$^{13}$, —OC(=O)OR$^{14}$, —OR$^{12}$, —OCH$_2$CO$_2$R$^{12}$, —CO$_2$CH$_2$CO$_2$R$^{12}$, —OC(=O)NR$^{23}$R$^{24}$, —C(=O)NR$^{23}$R$^{24}$, —NR$^{25}$R$^{26}$, —NR$^{27}$C(=O)R$^{13}$, —NR$^{27}$C(=O)OR$^{14}$, —NR$^{27}$SO$_2$R$^{14}$, —SR$^{14}$, —SOR$^{14}$, —SO$_2$R$^{14}$, —SO$_2$NR$^{23}$R$^{24}$, C$_1$–C$_{10}$ alkoxy, C$_1$–C$_{10}$ alkylcarbonyl, C$_2$–C$_6$ alkenyl, C$_3$–C$_{10}$ cycloalkyl, C$_4$–C$_{11}$ cycloalkylmethyl,
aryl, wherein said aryl is substituted with 0–3 groups selected from halogen, C$_1$–C$_6$ alkoxy, C$_1$–C$_6$ alkyl, halo, CF$_3$, CO$_2$R$^{12}$, SO$_2$Me, SOMe, SMe or —NMe$_2$,
aryl(C$_1$–C$_4$ alkyl)-, wherein said aryl is substituted with 0–3 groups selected from halogen, C$_1$–C$_6$ alkoxy, C$_1$–C$_6$ alkyl, CF$_3$, CO$_2$R$^{12}$, SO$_2$Me, SOMe, SMe, or —NMe$_2$, and
a 5–10 membered heterocyclic ring containing 1–3 N, O, or S heteroatoms, wherein said heterocyclic ring may be saturated, partially saturated, or fully unsaturated, said heterocyclic ring being substituted with 0–2 groups selected from halogen, C$_1$–C$_6$ alkoxy, C$_1$–C$_6$ alkyl, halo, CF$_3$, CO$_2$R$^{12}$, SO$_2$Me, SOMe, SMe or —NMe$_2$;

R$^9$ is selected from H, halogen, CF$_3$, CN, C$_1$–C$_4$ alkyl, or C$_1$–C$_4$ alkoxy;

R$^{10}$ is selected from:
H, hydroxy, CN, carboxy, —NR$^{25}$R$^{26}$; C$_1$–C$_6$ alkyl, C$_2$–C$_6$ alkenyl, C$_2$–C$_6$ alkynyl, C$_3$–C$_7$ cycloalkyl, C$_7$–C$_{14}$ bicycloalkyl, C$_1$–C$_6$ alkoxy, C$_1$–C$_6$ alkylthio, C$_1$–C$_6$ alkylsulfinyl, C$_1$–C$_6$ alkylsulfonyl, C$_1$–C$_6$ alkylcarbonyl, C$_1$–C$_6$ alkoxycarbonyl, aryl, piperidinyl, morpholinyl, and pyridinyl;

R$^{11}$ is selected from:
H, C$_1$–C$_8$ alkyl, C$_3$–C$_6$ alkenyl, C$_3$–C$_{11}$ cycloalkyl, C$_4$–C$_{11}$ cycloalkylmethyl, aryl, aryl(C$_1$–C$_4$ alkyl)-, and C$_1$–C$_{10}$ alkyl substituted with 1–2 R$^{10}$;

R$^{12}$ is selected from:
H, C$_1$–C$_8$ alkyl, C$_3$–C$_6$ alkenyl, C$_3$–C$_{11}$ cycloalkyl, C$_4$–C$_{11}$ cycloalkylmethyl, aryl, aryl(C$_1$–C$_4$ alkyl)-, and C$_1$–C$_{10}$ alkyl substituted with 1–2 R$^{10}$;

R$^{13}$ is selected from:
hydrogen, C$_1$–C$_8$ alkyl, C$_3$–C$_6$ alkenyl, C$_3$–C$_{11}$ cycloalkyl, C$_4$–C$_{11}$ cycloalkylmethyl, aryl, aryl(C$_1$–C$_4$ alkyl)-, heteroaryl, heteroaryl(C$_1$–C$_4$ alkyl)-, and C$_1$–C$_{10}$ alkyl substituted with 1–2 R$^{10}$;

R$^{14}$ is selected from:
C$_1$–C$_8$ alkyl, C$_2$–C$_6$ alkenyl, C$_3$–C$_{11}$ cycloalkyl, C$_4$–C$_{11}$ cycloalkylmethyl, aryl, aryl(C$_1$–C$_4$ alkyl)-, and C$_1$–C$_{10}$ alkyl substituted with 1–2 R$^{10}$;

R$^{15}$ is selected from:
H, OH, —OR$^{12}$, —CO$_2$R$^{12}$, —C(=O)NR$^{23}$R$^{24}$, —OC(=O)NR$^{23}$R$^{24}$, C$_1$–C$_{10}$ alkoxycarbonyl substituted with 0–2 R$^8$;
C$_1$–C$_{10}$ alkyl substituted with 0–3 R$^8$;
C$_2$–C$_{10}$ alkenyl substituted with 0–3 R$^8$; and
C$_1$–C$_{10}$ alkoxy substituted with 0–3 R$^8$;

R$^{16}$ is selected from:
—C(=O)OR$^{17}$, —C(=O)R$^{18}$, —C(=O)NR$^{17}$R$^{18}$, —C(=O)NHSO$_2$R$^{17}$, —C(=O)NHC(=O)R$^{17}$, —C(=O)NHC(=O)OR$^{17}$, —C(=O)NHSO$_2$NHR$^{17}$, —SO$_2$R$^{17}$, —SO$_2$NR$^{17}$R$^{18}$, and —SO$_2$NHC(=O)OR$^{17}$;

R$^{17}$ is selected from:
C$_1$–C$_8$ alkyl substituted with 0–2 R$^{19}$,
C$_3$–C$_8$ alkenyl substituted with 0–2 R$^{19}$,
C$_3$–C$_8$ alkynyl substituted with 0–2 R$^{19}$,
C$_3$–C$_8$ cycloalkyl substituted with 0–2 R$^{19}$,
aryl substituted with 0–4 R$^{19}$,
aryl(C$_1$–C$_6$ alkyl)-substituted with 0–4 R$^{19}$,
a 5–10 membered heterocyclic ring system having 1–3 heteroatoms selected independently from O, S, and N, said heterocyclic ring being substituted with 0–4 R$^{19}$, and
C$_1$–C$_6$ alkyl substituted with a 5–10 membered heterocyclic ring system having 1–3 heteroatoms selected independently from O, S, and N, said heterocyclic ring being substituted with 0–4 R$^{19}$;

R$^{18}$ is selected from H or R$^{17}$;

R$^{19}$ is selected from:
H, halogen, CF$_3$, CN, NO$_2$, NR$^{25}$R$^{26}$, C$_1$–C$_8$ alkyl, C$_2$–C$_6$ alkenyl, C$_2$–C$_6$ alkynyl, C$_3$–C$_{11}$ cycloalkyl, C$_3$–C$_{11}$ cycloalkyl(C$_1$–C$_4$ alkyl)-, aryl, aryl(C$_1$–C$_6$ alkyl)-, C$_1$–C$_6$ alkoxy, and C$_1$–C$_4$ alkoxycarbonyl;

R$^{20}$ is selected from:
H, C$_1$–C$_{10}$ alkyl, C$_2$–C$_6$ alkenyl, C$_3$–C$_{11}$ cycloalkyl, C$_3$–C$_{11}$ cycloalkyl(C$_1$–C$_4$ alkyl)-, aryl, and aryl(C$_1$–C$_{10}$ alkyl)-;

R$^{21}$ and R$^{22}$ are each independently H, methyl, ethyl, propyl, or butyl;

R$^{23}$ is selected from:
hydrogen, C$_1$–C$_8$ alkyl, C$_3$–C$_6$ alkenyl, C$_3$–C$_{11}$ cycloalkyl, C$_4$–C$_{11}$ cycloalkylmethyl, hydroxy, C$_1$–C$_6$ alkoxy, benzyloxy, aryl, aryl(C$_1$–C$_4$ alkyl)-, heteroaryl, heteroaryl(C$_1$–C$_4$ alkyl)-, adamantylmethyl, and C$_1$–C$_{10}$ alkyl substituted with 1–2 R$^{10}$;

R$^{24}$ is selected from:
C$_1$–C$_8$ alkyl, C$_2$–C$_6$ alkenyl, C$_3$–C$_{11}$ cycloalkyl, C$_4$–C$_{11}$ cycloalkylmethyl, aryl, aryl(C$_1$–C$_4$ alkyl)-, and C$_1$–C$_{10}$ alkyl substituted with 1–2 R$^{10}$;

R$^{25}$ and R$^{26}$ are, independently, selected from:
H, C$_1$–C$_{10}$ alkyl, C$_1$–C$_{10}$ alkoxycarbonyl, C$_1$–C$_{10}$ alkylcarbonyl, C$_1$–C$_{10}$ alkylsulfonyl, aryl, aryl(C$_1$–C$_4$ alkyl)-, arylcarbonyl, aryloxycarbonyl, arylsulfonyl, aryl(C$_1$–C$_{10}$ alkoxy)carbonyl, aryl(C$_1$–C$_{10}$ alkyl)sulfonyl, aryl(C$_2$–C$_{10}$ alkenyl)

sulfonyl, $C_2$–$C_6$ alkenyl, $C_3$–$C_{10}$ cycloalkyl, $C_3$–$C_{10}$ cycloalkyl($C_1$–$C_4$ alkyl)-, $C_3$–$C_{10}$ cycloalkoxycarbonyl, $C_7$–$C_{11}$ bicycloalkoxycarbonyl, heteroaryl, heteroarylcarbonyl, heteroarylsulfonyl, and heteroaryl($C_1$–$C_4$ alkyl)carbonyl, wherein said aryl groups are optionally substituted with 1–3 substituents selected from the group consisting of: $C_1$–$C_4$ alkyl, $C_1$–$C_4$ alkoxy, halo, $CF_3$, and $NO_2$;

$R^{27}$ is selected from H, methyl, ethyl, propyl, butyl, benzyl, phenethyl, cyclopropyl, and cyclopropylmethyl;

$R^{28}$ and $R^{29}$ are independently selected from:

H, $C_1$–$C_8$ alkyl, $C_3$–$C_6$ alkenyl, $C_3$–$C_{10}$ cycloalkyl ($C_0$–$C_4$ alkyl), aryl($C_0$–$C_4$ alkyl), and heteroaryl ($C_0$–$C_4$ alkyl), wherein said aryl or heteroaryl groups are substituted with 0–2 substituents independently selected from $C_1$–$C_4$ alkyl, $C_1$–$C_4$ alkoxy, F, Cl, Br, $CF_3$, and $NO_2$;

n is 0 or 1;
q is 1, 2, 3, or 4;
r is 0, 1, or 2; and
s is 1, 2, 3, or 4.

[9] Preferred compounds of this second embodiment are those compounds of Formula (I) wherein:

$R^1$ is selected from
$R^{2a}(R^3)N$—V—, $R^2(R^{2b})N(R^3N\!=\!)C$—V—, $R^2(R^{2b})N(R^3N\!=\!)CNH$—V—, $R^2(R^{11}O)N(R^3N\!=\!)C$—V—, $R^2(R^{2b})N(R^{11}ON\!=\!)C$—V—,

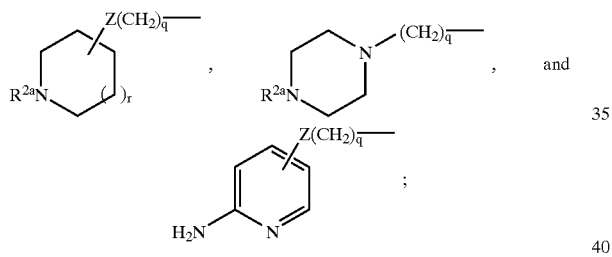

V is selected from:
—($C_1$–$C_4$ alkyl)-,
—(phenyl)-, said phenyl substituted with 0–2 groups independently selected from $R^9$,
—(pyridyl)-, said pyridyl substituted with 0–2 groups independently selected from $R^9$, or
—(pyridazinyl)-, said pyridazinyl substituted with 0–2 groups independently selected from $R^9$;

Z is selected from: a bond, O, and $S(\!=\!O)_2$;

X is —$OCH_2CH(W^a)$—, —$SCH_2CH(W^a)$—, —$NHCH_2CH(W^a)$—, —$OCH(W^b)$—, —$SCH(W^b)$—, or —$NHCH(W^b)$—;

$W^a$ is selected from:
H, hydroxy, —$NHR^{16}$, —$NR^{25}R^{26}$, $C_1$–$C_{10}$ alkoxy, $C_1$–$C_{10}$ alkyl substituted with 0–3 $R^8$, and aryl substituted with 0–3 $R^8$, $R^7$ is selected from:
H, $CH_2OH$, $CH_2OR^{12}$, $CH_2CO_2R^{12}$, $CH_2C(\!=\!O)NHR^{24}$, $CH_2NR^{25}R^{26}$, and $C_1$–$C_4$ alkyl substituted with 0–1 $R^8$;

$R^{12}$ is selected from H, aryl($C_1$–$C_4$ alkyl)-, and $C_1$–$C_{10}$ alkyl substituted with 1–2 $R^{10}$;

$R^{15}$ is selected from: H, OH, —$OR^{12}$, —$CO_2R^{12}$, —$C(\!=\!O)NR^{23}R^{24}$, and —$OC(\!=\!O)NR^{23}R^{24}$;

$R^{16}$ is selected from: —$C(\!=\!O)OR^{17}$, —$C(\!=\!O)R^{18}$, —$SO_2R^{17}$, and —$SO_2NR^{17}R^{18}$;

$R^{17}$ is selected from:
$C_1$–$C_8$ alkyl substituted with 0–2 $R^{19}$,
$C_3$–$C_8$ alkenyl substituted with 0–2 $R^{19}$,
$C_3$–$C_8$ alkynyl substituted with 0–2 $R^{19}$,
$C_3$–$C_8$ cycloalkyl substituted with 0–2 $R^{19}$,
aryl substituted with 0–4 $R^{19}$,
aryl($C_1$–$C_6$ alkyl)-substituted with 0–4 $R^{19}$,
a 5–10 membered heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzyimdazolyl, piperidinyl, tetrahydrofuranyl, pyranyl, pyrimidinyl, 3H-indolyl, pyrrolidinyl, morpholinyl, and piperazinyl, said heterocyclic ring being substituted with 0–4 $R^{19}$, said heterocyclic ring being substituted with 0–4 $R^{19}$, and
$C_1$–$C_6$ alkyl substituted with a 5–10 membered heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzyimdazolyl, piperidinyl, tetrahydrofuranyl, pyranyl, pyrimidinyl, 3H-indolyl, pyrrolidinyl, morpholinyl, or piperazinyl, said heterocyclic ring being substituted with 0–4 $R^{19}$;

$R^{18}$ is selected from H or $C_1$–$C_5$ alkyl;
n is 0 or 1;
q is 1, 2, 3, or 4;
r is 0, 1, or 2; and
s is 1, 2, 3, or 4.

[10] More preferred compounds of this second embodiment are those compounds of Formula (Ia)

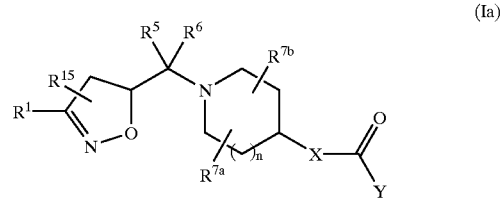

(Ia)

wherein:

$R^1$ is selected from
$R^2(R^{2b})N(R^3N\!=\!)C$—V—, $R^2(R^{2b})N(R^3N\!=\!)CNH$—V—,

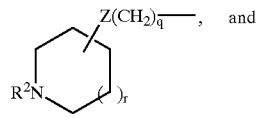

V is selected from:
—($C_1$–$C_4$ alkyl)-,
—(pyridyl)-, and
—(phenyl)-, said phenyl substituted with 0–2 groups independently selected from F, Br, methyl, and methoxy;

Z is a bond or O;

$R^2$, $R^{2b}$, and $R^3$ are independently selected from:
H, $C_1$–$C_8$ alkyl, $C_3$–$C_6$ alkenyl, $C_3$–$C_6$ alkynyl, $C_3$–$C_8$ cycloalkyl, $C_3$–$C_8$ cycloalkyl($C_1$–$C_4$ alkyl)-, $C_2$–$C_7$ alkylcarbonyl, $C_1$–$C_4$ haloalkyl, aryl, arylcarbonyl, aryl($C_1$–$C_4$ alkyl)-,
benzhydryl, benzhydryl ($C_1$–$C_4$ alkyl)-,
heteroaryl, heteroaryl($C_1$–$C_4$ alkyl)-, and
a cleavable protecting group selected from:
  $C_1$–$C_6$ alkoxycarbonyl,
  $C_3$–$C_8$ cycloalkoxycarbonyl,
  $C_7$–$C_{11}$ bicycloalkoxycarbonyl,
  aryloxycarbonyl,
  aryl($C_1$–$C_8$ alkoxy)carbonyl,
  ($C_1$–$C_6$ alkyl)carbonyloxy($C_1$–$C_4$ alkoxy) carbonyl,
  arylcarbonyloxy($C_1$–$C_4$ alkoxy)carbonyl, and
  ($C_3$–$C_8$ cycloalkyl)carbonyloxy($C_1$–$C_4$ alkoxy) carbonyl,
wherein at least one of $R^2$, $R^{2b}$, and $R^3$ is H or a cleavable protecting group;
wherein said aryl groups of $R^2$, $R^{2b}$, and $R^3$ may be substituted with 0–3 groups selected from hydroxy, halogen, $C_1$–$C_6$ alkoxy, $C_1$–$C_6$ alkyl, $CF_3$, —CN, —$SO_2$($C_1$–$C_4$ alkyl), —S($C_1$–$C_4$ alkyl), —$NR^{21}R^{22}$, $C_1$–$C_4$ haloalkyl, methylenedioxydiyl, and ethylenedioxydiyl; and
  said heteroaryl groups of $R^2$, $R^{2b}$, and $R^3$ may be substituted with 0–2 groups selected from hydroxy, halogen, $C_1$–$C_6$ alkoxy, $C_1$–$C_6$ alkyl, $CF_3$, $SO_2CH_3$, and —$NR^{21}R^{22}$;
alternatively, $R^2$ and $R^{2b}$ can be taken together with the nitrogen atom to which they are attached to form a 5–10 membered heterocyclic ring system selected from morpholine, piperidine, piperazine, pyrrolidine, tetrahydroisoquinoline, thiazolidine, thiomorpholine, 1,4-benzoxazine, 8-oxo-3-azabicyclo[3.2.1]octane, 1,4-dioxa-8-azaspiro[4.5] decane, or azepine, said heterocyclic ring being substituted with 0–2 $R^4$;
X is —$OCH_2CH(W^a)$—, —$NHCH_2CH(W^a)$—, —$OCH(W^b)$—, or —$NHCH(W^b)$—;
Y is selected from hydroxy,
  $C_1$–$C_6$ alkoxy;
  methylcarbonyloxymethoxy-;
  ethylcarbonyloxymethoxy-;
  t-butylcarbonyloxymethoxy-;
  cyclohexylcarbonyloxymethoxy-;
  1-(methylcarbonyloxy)ethoxy-;
  1-(ethylcarbonyloxy)ethoxy-;
  1-(t-butylcarbonyloxy)ethoxy-;
  1-(cyclohexylcarbonyloxy)ethoxy-;
  i-propyloxycarbonyloxymethoxy-;
  t-butyloxycarbonyloxymethoxy-;
  1-(i-propyloxycarbonyloxy)ethoxy-;
  1-(cyclohexyloxycarbonyloxy)ethoxy-;
  1-(t-butyloxycarbonyloxy)ethoxy-;
  dimethylaminoethoxy-;
  diethylaminoethoxy-;
  (5-methyl-1,3-dioxacyclopenten-2-on-4-yl)methoxy-;
  (5-(t-butyl)-1,3-dioxacyclopenten-2-on-4-yl) methoxy-;
  (1,3-dioxa-5-phenyl-cyclopenten-2-on-4-yl)methoxy-;
  1-(2-(2-methoxypropyl)carbonyloxy)ethoxy-;
$W^a$ is H or —$NHR^{16}$;
$W^b$ is H, methyl, ethyl, benzyl, phenethyl, pyridyl, pyridylmethyl, pyridylethyl, (indol-3-yl)ethyl, $CH_2C(=O)NHR^{18}$, and $CH_2NHR^{16}$;
$R^8$ is selected from:
  H, hydroxy, cyano, —$CO_2R^{12}$, —$C(=O)R^{13}$, —$C(=O)NR^{23}R^{24}$, —$NR^{25}R^{26}$, —$SR^{14}$, —$SOR^{14}$, —$SO_2R^{14}$, $C_1$–$C_{10}$ alkoxy, $C_1$–$C_{10}$ alkylcarbonyl, aryl, wherein said aryl is substituted with 0–3 groups selected from halogen, $C_1$–$C_6$ alkoxy, $C_1$–$C_6$ alkyl, halo, $CF_3$, $CO_2R^{12}$, $SO_2Me$, SOMe, SMe or —$NMe_2$,
a 5–10 membered heterocyclic ring system selected from pyridinyl, furanyl, thiazolyl, thienyl, pyrrolyl, pyrazolyl, triazolyl, imidazolyl, benzofuranyl, indolyl, inolinyl, quinolinyl, isoquinolinyl, benzimidazolyl, piperidinyl, tetrahydrofuranyl, pyranyl, 3H-indolyl, pyrrolidinyl, piperidinyl, isoxazolinyl, isoxazolyl or morpholinyl;
$R^{15}$ is selected from: H, OH, —$OR^{12}$, and —$OC(=O)NR^{23}R^{24}$;
$R^{16}$ is —$C(=O)OR^{17}$ or —$SO_2R^{17}$;
$R^{17}$ is selected from:
  $C_1$–$C_8$ alkyl,
  $C_2$–$C_8$ alkenyl,
  aryl substituted with 0–4 $R^{19}$,
  aryl($C_1$–$C_6$ alkyl)-substituted with 0–4 $R^{19}$,
  a 5–10 membered heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzyimdazolyl, piperidinyl, tetrahydrofuranyl, pyranyl, pyrimidinyl, 3H-indolyl, pyrrolidinyl, morpholinyl, and piperazinyl, said heterocyclic ring being substituted with 0–4 $R^{19}$, said heterocyclic ring being substituted with 0–4 $R^{19}$, and
  $C_1$–$C_6$ alkyl substituted with a 5–10 membered heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzyimdazolyl, piperidinyl, tetrahydrofuranyl, pyranyl, pyrimidinyl, 3H-indolyl, pyrrolidinyl, morpholinyl, or piperazinyl, said heterocyclic ring being substituted with 0–4 $R^{19}$;
$R^{19}$ is selected from:
  H, halogen, $CF_3$, CN, $NO_2$, $NR^{25}R^{26}$, $C_1$–$C_8$ alkyl, $C_2$–$C_6$ alkenyl, $C_2$–$C_6$ alkynyl, $C_3$–$C_{11}$ cycloalkyl, $C_3$–$C_{11}$ cycloalkyl ($C_1$–$C_4$ alkyl)-, aryl, aryl($C_1$–$C_6$ alkyl)-, $C_1$–$C_6$ alkoxy, and $C_1$–$C_4$ alkoxycarbonyl;
n is 0 or 1;
q is 1, 2, 3, or 4;
r is 0, 1, or 2; and
s is 1, 2, 3, or 4.
[11] Even more preferred compounds of this second embodiment are compounds of Formula (Ib), wherein:
$R^1$ is $R^2(R^{2b})N(R^3N=)C$—V— or $R^2(R^{2b})N(R^3N=)$ CNH—V—;
V is —(pyridyl)- or —(phenyl)-, said phenyl substituted with 0–2 groups independently selected from F, Br, methyl, and methoxy;
Z is a bond or O;
$R^2$, $R^{2b}$, and $R^3$ are independently selected from:
  H, $C_1$–$C_6$ alkyl, $C_3$–$C_6$ alkenyl, $C_3$–$C_6$ alkynyl, $C_3$–$C_8$ cycloalkyl, $C_3$–$C_8$ cycloalkyl($C_1$–$C_4$ alkyl)-, $C_2$–$C_7$ alkylcarbonyl, $C_1$–$C_4$ haloalkyl, arylcarbonyl, aryl($C_1$–$C_4$ alkyl)-, benzhydryl, heteroaryl, heteroaryl($C_1$–$C_4$ alkyl)-, and
  a cleavable protecting group selected from:
    $C_1$–$C_4$ alkoxycarbonyl,
    $C_3$–$C_6$ cycloalkoxycarbonyl, $C_7$–$C_{11}$ bicycloalkoxycarbonyl,
aryl($C_1$–$C_8$ alkoxy)carbonyl,
($C_1$–$C_6$ alkyl)carbonyloxy($C_1$–$C_4$ alkoxy) carbonyl,
arylcarbonyloxy($C_1$–$C_4$ alkoxy)carbonyl, and
($C_3$–$C_8$ cycloalkyl)carbonyloxy($C_1$–$C_4$ alkoxy) carbonyl, wherein at least one of $R^2$, $R^{2b}$, and $R^3$ is H or a cleavable protecting group;

wherein said aryl groups of $R^2$, $R^{2b}$, and $R^3$ may be substituted with 0–3 groups selected from hydroxy, halogen, methoxy, ethoxy, propoxy, butoxy, methyl, ethyl, propyl, butyl, $CF_3$, —CN, —$SO_2(CH_3)$, —$SO_2(C_2H_5)$, —$SO_2(C_3H_7)$, —$SO_2(C_4H_9)$, —$NR^{21}R^{22}$, $C_1$–$C_4$ haloalkyl, methylenedioxydiyl, and ethylenedioxydiyl; and said heteroaryl groups of $R^2$, $R^{2b}$, and $R^3$ may be substituted with 0–2 groups selected from hydroxy, halogen, methoxy, ethoxy, propoxy, butoxy, methyl, ethyl, propyl, butyl, $CF_3$, $SO_2CH_3$, and —$NR^{21}R^{22}$;

alternatively, $R^2$ and $R^{2b}$ can be taken together with the nitrogen atom to which they are attached to form a 5–10 membered heterocyclic ring system selected from morpholine, piperidine, piperazine, pyrrolidine, tetrahydroisoquinoline, thiazolidine, thiomorpholine, 1,4-benzoxazine, 8-oxo-3-azabicyclo[3.2.1]octane, 1,4-dioxa-8-azaspiro[4.5]decane, or azepine, said heterocyclic ring being substituted with 0–2 $R^4$;

$R^4$, when a substituent on carbon, is independently selected from H, methyl, ethyl, propyl, butyl, and phenyl; wherein said phenyl groups may be optionally substituted with 0–3 groups selected from hydroxy, halogen, methoxy, methyl, ethyl, $CF_3$, $SCH_3$, —$NH_2$, —$NH(CH_3)$, —$N(CH_3)_2$, methylenedioxydiyl, and ethylenedioxydiyl;

alternatively, when two $R^4$ groups are attached to adjacent carbon atoms, they may be taken together with the atoms to which they are attached to form a fused 5–7 membered saturated, unsaturated or aromatic carbocyclic ring;

alternatively, when $R^4$ is attached to a saturated carbon atom, it may also be =O or =S;

$R^4$ when a substituent on nitrogen, is independently selected from H, methyl, ethyl, propyl, butyl, cyclopropyl, cyclopropylmethyl, phenyl, phenylmethyl, phenylethyl, pyridyl, pyridylmethyl wherein said phenyl or pyridyl groups may be additionally substitututed with 0–2 groups selected from hydroxy, halogen, methoxy, methyl, ethyl, $CF_3$, $SCH_3$, —$NH_2$, —$NH(CH_3)$, and —$N(CH_3)_2$;

$R^4$ when a substituent on sulfur, may be =O;

X is —$OCH_2CH(W^a)$— or —$OCH(W^b)$—;

Y is selected from hydroxy; methoxy; ethoxy; isopropoxy; n-butyloxy; isobutyloxy; t-butoxy; benzyloxy;
methylcarbonyloxymethoxy-;
ethylcarbonyloxymethoxy-;
t-butylcarbonyloxymethoxy-;
cyclohexylcarbonyloxymethoxy-;
1-(methylcarbonyloxy)ethoxy-;
1-(ethylcarbonyloxy)ethoxy-;
1-(t-butylcarbonyloxy)ethoxy-;
1-(cyclohexylcarbonyloxy)ethoxy-;
i-propyloxycarbonyloxymethoxy-;
t-butyloxycarbonyloxymethoxy-;
1-(i-propyloxycarbonyloxy)ethoxy-;
1-(cyclohexyloxycarbonyloxy)ethoxy-;
1-(t-butyloxycarbonyloxy)ethoxy-;
dimethylaminoethoxy-;
diethylaminoethoxy-;
(5-methyl-1,3-dioxacyclopenten-2-on-4-yl)methoxy-;
(5-(t-butyl)-1,3-dioxacyclopenten-2-on-4-yl)methoxy-;
(1,3-dioxa-5-phenyl-cyclopenten-2-on-4-yl)methoxy-;
1-(2-(2-methoxypropyl)carbonyloxy)ethoxy-;

$W^a$ is H or —$NHR^{16}$;

$W^b$ is H, methyl, ethyl, benzyl, phenethyl, pyridyl, pyridylmethyl, pyridylethyl, (indol-3-yl)ethyl, $CH_2C(=O)NHR^{18}$, and $CH_2NHR^{16}$;

$R^8$ is selected from:
H, hydroxy, cyano, —$CO_2R^{12}$, —$C(=O)R^{13}$, —$C(=O)NR^{23}R^{24}$, —$NR^{25}R^{26}$, —$SR^{14}$, —$SOR^{14}$, —$SO_2R^{14}$, $C_1$–$C_4$ alkoxy, $C_1$–$C_4$ alkylcarbonyl, aryl, wherein said aryl is substituted with 0–3 groups selected from halogen, methoxy, ethoxy, propoxy, butoxy, methyl, ethyl, propyl, butyl, $CF_3$, $CO_2R^{12}$, $SO_2Me$, $SOMe$, $SMe$ or —$NMe_2$, a 5–10 membered heterocyclic ring system selected from pyridinyl, furanyl, thiazolyl, thienyl, pyrrolyl, pyrazolyl, triazolyl, imidazolyl, benzofuranyl, indolyl, inolinyl, quinolinyl, isoquinolinyl, benzimidazolyl, piperidinyl, tetrahydrofuranyl, pyranyl, 3H-indolyl, pyrrolidinyl, piperidinyl, isoxazolinyl, isoxazolyl or morpholinyl;

$R^{15}$ is H;

$R^{16}$ is —$SO_2R^{17}$, —$C(=O)OCH_2CH_2CH_2CH_3$, —$C(=O)OCH_2CH(CH_3)_2$ or —$C(=O)OCH_2(C_6H_5)$;

$R^{17}$ is selected from:
$C_1$–$C_8$ alkyl,
aryl substituted with 0–2 $R^{19}$,
aryl($C_1$–$C_6$ alkyl)-substituted with 0–2 $R^{19}$,
a 5–10 membered heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzyimdazolyl, piperidinyl, tetrahydrofuranyl, pyranyl, pyrimidinyl, 3H-indolyl, pyrrolidinyl, morpholinyl, and piperazinyl, said heterocyclic ring being substituted with 0–2 $R^{19}$, said heterocyclic ring being substituted with 0–2 $R^{19}$, and $C_1$–$C_6$ alkyl substituted with a 5–10 membered heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzyimdazolyl, piperidinyl, tetrahydrofuranyl, pyranyl, pyrimidinyl, 3H-indolyl, pyrrolidinyl, morpholinyl, or piperazinyl, said heterocyclic ring being substituted with 0–2 $R^{19}$;

$R^{19}$ is selected from:
H, halogen, $CF_3$, CN, $NO_2$, $NR^{25}R^{26}$, $C_1$–$C_4$ alkyl, $C_2$–$C_4$ alkenyl, $C_2$–$C_4$ alkynyl, $C_3$–$C_6$ cycloalkyl, $C_3$–$C_6$ cycloalkyl($C_1$–$C_4$ alkyl)-, aryl, aryl($C_1$–$C_4$ alkyl)-, $C_1$–$C_4$ alkoxy, and $C_1$–$C_4$ alkoxycarbonyl;

n is 1; and s is 1 or 2.

[12] Specifically preferred compounds of this second embodiment are compounds, or pharmaceutically acceptable salt or prodrug forms thereof, selected from:

[1-[[3-[4-(aminoiminomethyl)phenyl]isoxazolin-5-yl]carbonyl]piperidin-4-yl]oxyacetic acid;

[1-[[3-[4-[(n-butylamino)iminomethyl]phenyl]isoxazolin-5-yl]carbonyl]piperidin-4-yl]oxyacetic acid;

[1-[[3-[4-[(2-phenylethylamino)iminomethyl]phenyl]-isoxazolin-5-yl]carbonyl]piperidin-4-yl]oxyacetic acid;

[1-[[3-[4-[(phenylmethylamino)iminomethyl]phenyl]-isoxazolin-5-yl]carbonyl]piperidin-4-yl]oxyacetic acid;

[1-[[3-[4-[(n-propylamino)iminomethyl]phenyl]isoxazolin-5-yl]carbonyl]piperidin-4-yl]oxyacetic acid;

[1-[[3-[4-[(ethylamino)iminomethyl]phenyl]isoxazolin-5-yl]carbonyl]piperidin-4-yl]oxyacetic acid;

[1-[[3-[4-[(morpholino)iminomethyl]phenyl]isoxazolin-5-yl]carbonyl]piperidin-4-yl]oxyacetic acid;

[1-[[3-[4-[(piperidino)iminomethyl]phenyl]isoxazolin-5-yl]carbonyl]piperidin-4-yl]oxyacetic acid;

[1-[[3-[4-[(thiazolidino)iminomethyl]phenyl]isoxazolin-5-yl]carbonyl]piperidin-4-yl]oxyacetic acid;

[1-[[3-[4-[(2,6-dimethylmorpholino)iminomethyl]phenyl]-isoxazolin-5-yl]carbonyl]piperidin-4-yl]oxyacetic acid;

[1-[[3-[4-[(4-methylpiperazino)iminomethyl]phenyl]-isoxazolin-5-yl]carbonyl]piperidin-4-yl]oxyacetic acid;

[1-[[3-[4-[(4-phenylpiperazino)iminomethyl]phenyl]-isoxazolin-5-yl]carbonyl]piperidin-4-yl]oxyacetic acid;

[1-[[3-[4-[(pyrrolidino)iminomethyl]phenyl]isoxazolin-5-yl]carbonyl]piperidin-4-yl]oxyacetic acid;

[1-[[3-[4-[(2,6-dimethylpiperazino)iminomethyl]phenyl]-isoxazolin-5-yl]carbonyl]piperidin-4-yl]oxyacetic acid;

[1-[[3-[4-[(2-fluorophenyl)piperazino)iminomethyl]phenyl]-isoxazolin-5-yl]carbonyl]piperidin-4-yl]oxyacetic acid;

[1-[[3-[4-[(2-methylphenyl)piperazino)iminomethyl]phenyl]-isoxazolin-5-yl]carbonyl]piperidin-4-yl]oxyacetic acid;

[1-[[3-[4-[(thiomorpholino)iminomethyl]phenyl]isoxazolin-5-yl]carbonyl]piperidin-4-yl]oxyacetic acid;

[1-[[3-[4-[(4-pyridylethylamino)iminomethyl]phenyl]-isoxazolin-5-yl]carbonyl]piperidin-4-yl]oxyacetic acid; and

[1-[[3-[4-[(4-propylpiperazino)iminomethyl]phenyl]-isoxazolin-5-yl]carbonyl]piperidin-4-yl]oxyacetic acid;

[1-[[3-[4-[(1,2,3,4-tetrahydroisoquinolino)iminomethyl]-phenyl]isoxazolin-5-yl]carbonyl]-4-piperidinyl]acetic acid; and

[1-[[3-[4-[(1,2,3,4-tetrahydro-2,7-naphthyridino)iminomethyl]phenyl]isoxazolin-5-yl]carbonyl]-4-piperidinyl]-acetic acid.

In another preferred embodiment, the present invention provides a compound of Formula (I) or (Ia) wherein the stereochemistry of the isozazolin-5-yl-$CR^5R^6$-moiety is either isozazolin-5(S)-yl-$CR^5R^6$— or isozazolin-5(R)-yl-$CR^5R^6$—. Depending on the substitution pattern of the isoxazoline, a compound of Formula (I) or (Ia) with a isozazolin-5(S)-yl-$CR^5R^6$— or isozazolin-5(R)-yl-$CR^5R^6$-moiety is depicted by one of the following formulas:

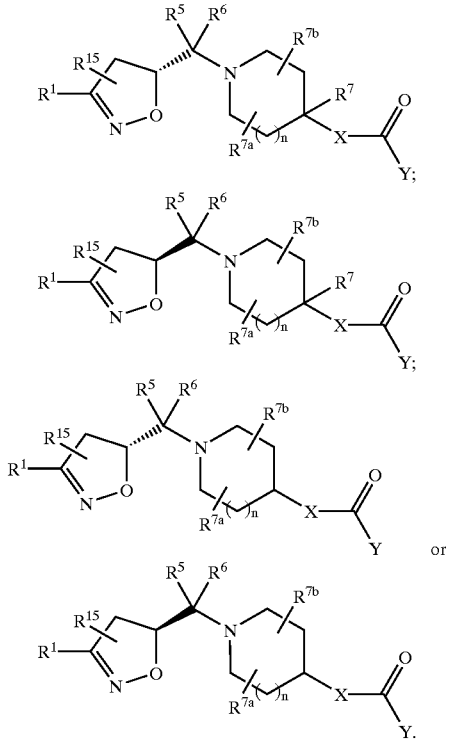

In the present invention it has been discovered that the compounds of Formula (I) above are useful as inhibitors of cell-matrix and cell-cell adhesion processes. The present invention includes novel compounds of Formula (I) and methods for using such compounds for the prevention or treatment of diseases resulting from abnormal cell adhesion to the extracellular matrix which comprises administering to a host in need of such treatment a therapeutically effective amount of such compound of Formula I.

In the present invention it has also been discovered that the compounds of Formula (I) above are useful as inhibitors of glycoprotein IIb/IIIa (GPIIb/IIIa) The compounds of the present invention inhibit the activation and aggregation of platelets induced by all known endogenous platelet agonists.

The present invention also provides pharmaceutical compositions comprising a compound of Formula (I) and a pharmaceutically acceptable carrier.

The compounds of Formula (I) of the present invention are useful for the treatment (including prevention) of thromboembolic disorders. The term "thromboembolic disorders" as used herein includes conditions involving platelet activation and aggregation, such as arterial or venous cardiovascular or cerebrovascular thromboembolic disorders, including, for example, thrombosis, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, myocardial infarction, cerebral embolism, kidney embolisms, pulmonary embolisms, or such disorders associated with diabetes, comprising administering to a mammal in need of such treatment a therapeutically effective amount of a compound of Formula (I) described above.

The compounds of Formula (I) of the present invention may be useful for the treatment or prevention of other diseases which involve cell adhesion processes, including, but not limited to, infammation, bone degradation, rheumatoid arthritis, asthma, allergies, adult respiratory distress syndrome, graft versus host disease, organ transplantation rejection, septic shock, psoriasis, eczema, contact dermatitis, osteoporosis, osteoarthritis, atherosclerosis, tumors, metastasis, diabetic retinopathy, inflammatory bowel disease and other autoimmune diseases. The compounds of Formula (I) of the present invention may also be useful for wound healing.

The compounds of the present invention are useful for inhibiting the binding of fibrinogen to blood platelets, inhibiting aggregation of blood platelets, treating thrombus formation or embolus formation, or preventing thrombus or embolus formation in a mammal. The compounds of the invention may be used as a medicament for blocking fibrinogen from acting at its receptor site in a mammal.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption, and where the aggregated platelets may form thrombi and thromboemboli. The compounds of the present invention may be administered to these surgical patients to prevent the formation of thrombi and thromboemboli.

Extracorporeal circulation is routinely used during cardiovascular surgery in order to oxygenate blood. Platelets adhere to surfaces of the extracorporeal circuit. Adhesion is dependent on the interaction between GPIIb/IIIa on the platelet membranes and fibrinogen adsorbed to the surface of the extracorporeal circuit. Platelets released from artificial surfaces show impaired homeostatic function. The compounds of the invention may be administered to prevent such ex vivo adhesion.

The compounds of the present invention may be used for other ex vivo applications to prevent cellular adhesion in biological samples.

Other applications of these compounds include prevention of platelet thrombosis, thromboembolism, and reocclusion during and after thrombolytic therapy and prevention of platelet thrombosis, thromboembolism and reocclusion after angioplasty of coronary and other arteries and after coronary artery bypass procedures. The compounds of the present invention may also be used to prevent myocardial infarction. The compounds of the present invention are useful as thrombolytics for the treatment of thromboembolic disorders.

The compounds of the present invention can also be administered in combination with one or more additional therapeutic agents select from: anti-coagulant or coagulation inhibitory agents, such as heparin or warfarin; anti-platelet or platelet inhibitory agents, such as aspirin, piroxicam, or ticlopidine; thrombin inhibitors such as boropeptides, hirudin or argatroban; or thrombolytic or fibrinolytic agents, such as plasminogen activators, anistreplase, urokinase, streptokinase, or reteplase.

The compounds of Formula (I) of the present invention can be administered in combination with one or more of the foregoing additional therapeutic agents, thereby to reduce the doses of each drug required to achieve the desired therapeutic effect. Thus, the combination treatment of the present invention permits the use of lower doses of each component, with reduced adverse, toxic effects of each component. A lower dosage minimizes the potential of side effects of the compounds, thereby providing an increased margin of safety relative to the margin of safety for each component when used as a single agent. Such combination therapies may be employed to achieve synergistic or additive therapeutic effects for the treatment of thromboembolic disorders.

The term "integrin" as used herein refers to any of the many cell surface receptor proteins, also referred to as adhesion protein receptors, which have been identified which bind to extracellular matrix ligands or other cell adhesion protein ligands thereby mediating cell-cell and cell-matrix adhesion processes. The integrins are encoded by genes belonging to a gene superfamily and are typically composed of heterodimeric transmembrane glycoproteins containing $\alpha$- and $\beta$-subunits. Integrin subfamilies contain a common $\beta$-subunit combined with different $\alpha$-subunits to form adhesion protein receptors with different specificities.

The integrin glycoprotein IIb/IIIa (referred to herein as GPIIb/IIIa or IIb/IIIa or the fibrinogen receptor) is the membrane protein mediating platelet aggregation. GPIIb/IIIa in activated platelets is known to bind four soluble RGD-containing adhesive proteins, namely fibrinogen, von Willebrand factor, fibronectin, and vitronectin. In addition to GPIIb/IIIa, a number of other integrin cell surface receptors have been identified, for example, $\alpha v \beta 3$ and $\alpha 5 \beta 1$.

The term "integrin antagonists" as referred to herein (also referred to herein as integrin inhibitors) includes compounds (including peptidomimetic compounds and other small molecule compounds) which act as inhibitors of the binding of the integrin protein to endogenous protein ligands of such integrin. Preferred integrin inhibitors used in the present invention are RGD-peptidomimetic compounds. As used herein, the term "RGD-peptidomimetic compounds" refers to chemical compounds which bind to the RGD-binding region of the integrin and which block RGD-mediated binding of one or more adhesive proteins to such integrin. Preferred in the present invention are antagonists of the $\alpha v \beta 3$ and GPIIb/IIIa integrin.

By "therapeutically effective amount" it is meant an amount of a compound of Formula (I) that when administered alone or in combination with an additional therapeutic agent to a cell or mammal is effective to prevent or ameliorate the thromboembolic disease condition or the progression of the disease. Such disease conditions or diseases include thromboembolic disorders and cell adhesion prosesses as disclosed herein.

By "administered in combination" or "combination therapy" it is meant that the compound of Formula (I) and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term "anti-coagulant agents" (or coagulation inhibitory agents), as used herein, denotes agents that inhibit blood coagulation. Such agents include warfarin (available as Coumadin™), heparin, and low molecular weight heparin.

The term "anti-platelet agents" (or platelet inhibitory agents), as used herein, denotes agents that inhibit platelet function such as by inhibiting the aggregation, adhesion or granular secretion of platelets. Such agents include the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Piroxicam is commercially available from Pfizer Inc. (New York, N.Y.), as Feldane™. Other suitable anti-platelet agents include ticlopidine, including pharmaceutically acceptable salts or prodrugs thereof. Ticlopidine is also a preferred compound since it is known to be gentle on the gastrointestinal tract in use. Still other suitable platelet inhibitory agents include other IIb/IIIa antagonists, such as ReoPro™ (abciximab, available from Centocor), Integrilin™ (eptifibatide, available from COR Therapeutics), and Aggrastat™ (tirofiban, available from Merck and Co.).

Still other suitable platelet inhibitory agents include thromboxane-A2-receptor antagonists and thromboxane-A2-synthetase inhibitors, as well as pharmaceutically acceptable salts or prodrugs thereof.

The phrase "thrombin inhibitors" (or "anti-thrombin agents"), as used herein, denotes inhibitors of the serine protease thrombin and other inhibitors of thrombin synthesis such as factor Xa inhibitors. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. Such inhibitors include hirudin and argatroban, including pharmaceutically acceptable salts and prodrugs thereof. The term hirudin, as used herein, includes suitable derivatives or analogs of hirudin, referred to herein as hirulogs, such as disulfatohirudin.

The term "factor Xa inhibitor", as used herein, denotes inhibitors of factor Xa, whose major practical role is the generation of thrombin by the limited proteolysis of prothrombin. The generation of thrombin from its precursor prothrombin is amplified by formation of prothrombinase complex (factor Xa, factor V, $Ca^{2+}$ and phospholipid). Therefore, it is envisioned that adminstration of an inhibitor of thrombin synthesis, such as a factor Xa inhibitor, in combination therapy with a IIbIIIa inhibitor of the instant invention may be an additional method in treating cardiovascular disease, thrombosis, reocclusion following thrombolysis, reperfusion injury, or restenosisother than administering a compound of Formula (I) alone. Such factor Xa inhibitors include, but are not limited to, DX-9065a (Daiichi), ORG31540 (Organon), SANORG 32701 (Sanofi/Organon), and BX-807834 (Berlex). Such factor Xa inhibitors also include, but are not limited to, compounds disclosed in WO97/23212, published Jul. 3, 1997; WO97/38984, published Oct. 23, 1997; WO97/30971, published Aug. 28, 1997; WO98/01428, published Jan. 15, 1998; WO98/06694, published Feb. 19, 1998; WO98/28269, published Jul. 2, 1998; and WO98/28282, published Jul. 2, 1998; each reference herein incorporated by reference in its entirety.

The phrase "thrombolytic agents" or "fibrinolytic agents" (or "thrombolytics" or "fibrinolytics"), as used herein, denotes agents that lyse blood clots (thrombi). Such agents include tissue plasminogen activator, anistreplase, urokinase, streptokinase, or reteplase, including pharmaceutically acceptable salts or prodrugs thereof. Tissue plasminogen activator (tPA) is commercially available from Genentech Inc., South San Francisco, Calif. The term anistreplase, as used herein, refers to anisoylated plasminogen streptokinase activator complex, as described, for example, in European Patent Application No. 028,489, the disclosures of which are hereby incorporated herein by reference herein, in their entirety. Anistreplase is commercially available as Eminase™. The term urokinase, as used herein, is intended to denote both dual and single chain urokinase, the latter also being referred to herein as prourokinase. Reteplase is manufactured by Boehringer Mannheim Corp. and commercially available as Retavase™.

Administration of the compounds of Formula (I) of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the binding of fibrinogen to platelet GPIIb/IIIa. Such compounds may be provided in a commercial kit, for example, for use in pharmaceutical research involving GPIIb/IIIa. The compounds of the present invention may also be used in diagnostic assays involving platelet GPIIb/IIIa.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention that contain asymmetrically substituted carbon atoms may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable (for example but not limited to, $R^2$, $R^{2b}$, $R^8$, $R^9$, $R^{10}$, $R^{11}$, $R^{12}$, $R^{13}$, $R^{14}$, $R^{19}$, $R^{21}$, $R^{22}$, $R^{23}$, $R^{24}$, $R^{25}$, $R^{26}$, and s, etc.) occurs more than one time in any constituent or in any formula, its definition on each occurrence is independent of its definition at every other occurrence. Thus, for example, if a group is shown to be substituted with 0–2 $R^8$, then said group may optionally be substituted with up to two $R^8$ and $R^8$ at each occurrence is selected independently from the defined list of possible $R^8$.

When a bond to a substituent is shown to cross the bond connecting two atoms in a ring, then such substituent may be bonded to any atom on the ring. When a bond joining a substituent to another group is not specifically shown or the atom in such other group to which the bond joins is not specifically shown, then such substituent may form a bond with any atom on such other group.

When a substituent is listed without indicating the atom via which such substituent is bonded to the rest of the compound of Formula I, then such substituent may be bonded via any atom in such substituent. For example, when the substituent is piperidinyl, morpholinyl, or pyridinyl, unless specified otherwise, said piperidinyl, morpholinyl, or pyridinyl group may be bonded to the rest of the compound of Formula (I) via any atom in such piperidinyl, morpholinyl, or pyridinyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, "alkyl" or "alkylene" is intended to include both branched and straight-chain saturated aliphatic hydrocarbon groups having the specified number of carbon atoms; for example, "$C_1$–$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, pentyl, and hexyl.

"Alkenyl" or "alkenylene" is intended to include hydrocarbon chains of either a straight or branched configuration, having the specified number of carbon atoms, and one or more unsaturated carbon-carbon bonds which may occur in any stable point along the chain, such as ethenyl, propenyl, 1-butenyl, 2-butenyl and the like. "Alkynyl" or "alkynylene" is intended to include hydrocarbon chains of either a straight or branched configuration, having the specified number of carbon atoms, and one or more carbon-carbon triple bonds which may occur in any stable point along the chain, such as ethynyl, propynyl, 1-butynyl, 2-butynyl and the like.

The term "haloalkyl" is intended to include both branched and straight-chain saturated aliphatic hydrocarbon groups having the specified number of carbon atoms, substituted independently with 1 or more halogens (for example —$C_vF_w$ where v=1 to 3 and w=1 to (2v+1)), such as, but not limited to, —$CH_2F$, —$CHF_2$, —$CF_3$, —$CF_2Br$, —$CH_2CF_3$, —$CF_2CF_3$, —$CH(CF_3)_2$ and the like.

As used herein, "alkyloxy" or "alkoxy" represents an alkyl group of indicated number of carbon atoms attached through an oxygen bridge, for example methoxy, ethoxy, propoxy, i-propoxy, butoxy, i-butoxy, s-butoxy and t-butoxy. The term "aryloxy" is intended to mean phenyl or naphthyl attached through an oxygen bridge;

The term "cycloalkyl" is intended to include saturated ring groups having the specified number of carbon atoms, including mono-, bi-, or poly-cyclic ring systems, such as cyclopropyl (c-Pr), cyclobutyl (c-Bu), cyclopentyl, cyclohexyl, cycloheptyl, cyclooctyl, [3.3.0]bicyclooctyl, [2.2.2]bicyclooctyl, adamantyl and so forth. More specifically, "bicycloalkyl" is intended to include saturated bicyclic ring groups having the specified number of carbon atoms, such as [3.3.0]bicyclooctyl, [4.3.0]bicyclononyl, [4.4.0]bicyclodecyl (decalin), [2.2.2]bicyclooctyl, and so forth.

Additionally, the terms "alkylene", "alkenylene", "phenylene", and the like, refer to alkyl, alkenyl, and phenyl groups, respectively, which are connected by two bonds to the rest of the structure of Formula I. Such "alkylene", "alkenylene", "phenylene", and the like, may alternatively and equivalently be denoted herein as "—(alkyl)—", "—(alkenyl)—" and "—(phenyl)—", and the like.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean 6 to 10 membered monocyclic or bicyclic unsaturated carbon ring, for example phenyl or naphthyl. As used herein "aryl" is optionally substituted with 0–3 groups independently selected from methyl, methoxy, amino, hydroxy, halogen, $C_1$–$C_6$ alkoxy, $C_1$–$C_6$ alkyl, $CF_3$, $SCH_3$, $S(O)CH_3$, $SO_2CH_3$, —$N(CH_3)_2$, $C_1$–$C_4$ haloalkyl, methylenedioxydiyl, or ethylenedioxydiyl.

The term "arylalkyl" represents an aryl group attached through an alkyl bridge having the specified number of carbon atoms.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic" is intended to mean a stable 5- to 7-membered monocyclic or bicyclic or 7- to 10-membered bicyclic heterocyclic ring which may be saturated, partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, isoxazolinyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl octahydroisoquinolinyl, azocinyl, triazinyl, 6H-1,2,5-thiadiazinyl, 2H, 6H-1,5,2-dithiazinyl, thianthrenyl, pyranyl, isobenzofuranyl, chromenyl, xanthenyl, phenoxathiinyl, 2H-pyrrolyl, isothiazolyl, isoxazolyl, oxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, 1,4-benzoxazine, and 8-oxa-3-azabicyclo[3.2.1]octane. Preferred heterocyclic rings are pyridinyl, furanyl, thiazolyl, thienyl, pyrrolyl, pyrazolyl, triazolyl, imidazolyl, benzofuranyl, indolyl, indolinyl, quinolinyl, isoquinolinyl, tetrahydroisoquinolinyl, isoxazolyl, isoxazolinyl, benzyimdazolyl, piperidinyl, tetrahydrofuranyl, pyranyl, pyrimidinyl, 3H-indolyl, pyrrolidinyl, morpholinyl, and piperazinyl. Also included are fused ring and spiro compounds containing, for example, the above heterocycles.

As used herein, the term "heteroaryl" refers to aromatic heterocyclic groups. Such heteroaryl groups are preferably 5–6 membered monocylic groups or 8–10 membered fused bicyclic groups. Examples of such heteroaryl groups include, but are not limited to pyridyl (pyridinyl), pyrimidinyl, furanyl (furyl), thiazolyl, thienyl, pyrrolyl, pyrazolyl, imidazolyl, indolyl, isoxazolyl, oxazolyl, pyrazinyl, pyridazinyl, benzofuranyl, benzothienyl, benzimidazolyl, quinolinyl, or isoquinolinyl.

As used herein, the term "chiral amine" refers to any amine containing compound that also contains a chiral center. Such compounds include, by way of example and without limitation, either enantiomer of cinchonidine, ephedrine, 2-phenylglycinol, 2-amino-3-methoxy-1-propanol, quinidine and pseudoephedrine.

As used herein, "carbonyl" means a carbon double bonded to oxygen and additionally substituted with two groups through single bonds; "carbonyloxy" means a carbon double bonded to oxygen and additionally bonded through a single bonds to two groups, one of which is an oxygen. As used herein, "sulfonyl" is intended to mean a sulfur bonded through double bonds to two oxygens and bonded to two additional groups through single bonds.

As used herein, any carbon range such as "$C_x$–$C_y$" is intended to mean a minimum of "x" carbons and a maximum of "y" carbons representing the total number of carbons in the substituent to which it modifies, for example $C_1$–$C_6$ alkyl or $C_3$–$C_{10}$ cycloalkyl($C_1$–$C_6$ alkyl)- or aryl($C_1$–$C_6$ alkyl) or aryl($C_1$–$C_6$ alkyl)carbonyl means an alkyl substituent of one to six carbons independent of the cycloalkyl, aryl or carbonyl respectively. However, if not specified, for example in "$C_2$–$C_{10}$ alkylcarbonyloxyalkyloxy" or "$C_4$–$C_{10}$ cycloalkylcarbonyloxyalkyloxy" or "$C_7$–$C_{11}$ aryloxycarbonylalkyloxy", the carbon range "$C_x$–$C_y$" is intended to mean the range of total number of carbons in the substituent not including the "carbonyl".

As used herein, "pharmaceutically acceptable salts" refer to derivatives of the disclosed compounds wherein the parent compound of Formula (I) is modified by making acid or base salts of the compound of Formula I. Examples of pharmaceutically acceptable salts include, but are not limited to, mineral or organic acid salts of basic residues such as amines; alkali or organic salts of acidic residues such as carboxylic acids; and the like.

Since prodrugs are known to enhance numerous desirable qualities of pharmaceuticals (e.g., solubility, bioavailability, manufacturing, etc . . . ) the compounds of the present invention may be manufactured or therapeutically delivered in prodrug form. Thus, the present invention is intended to cover prodrugs of the presently claimed compounds, methods of delivering the same, and compositions containing the same. "Prodrugs" are considered to be any covalently bonded carriers which release the active parent drug according to Formula (I) in vivo when such prodrug is administered to a mammalian subject. Prodrugs of the compounds of Formula (I) are prepared by modifying functional groups present in the compounds in such a way that the modifications are cleaved, either in routine manipulation or in vivo, to the parent compounds. Prodrugs include compounds of Formula (I) wherein hydroxyl, amino, sulfhydryl, or carboxyl groups are bonded to any group that, when administered to a mammalian subject, cleaves to form a free hydroxyl, amino, sulfhydryl, or carboxyl group, respectively. An example any group that, when administered to a mammalian subject, cleaves to form a free amino, is disclosed in the definition of $R^2$, $R^{2b}$, or $R^3$, as "a cleavable protecting group." Examples of prodrugs include, but are not limited to, acetate, formate and benzoate derivatives of alcohol and amine functional groups in the compounds of Formula I, and the like. Examples of representative amino and carboxyl prodrugs are included under the definitions of $R^2$, $R^{2b}$, $R^3$, and Y.

The pharmaceutically acceptable salts of the compounds of Formula (I) include the conventional non-toxic salts or the quaternary ammonium salts of the compounds of Formula (I) formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula (I) which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula (I) with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammoinum hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The disclosures of all of the references cited herein are hereby incorporated herein by reference in their entirety.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

Compounds of Formula (I) can be conveniently prepared by dipolar cycloaddition of nitrile oxides with appropriate dipolarophiles (for reviews of 1,3-dipolar cycloaddtiion chemistry, see 1,3-Dipolar Cycloaddition Chemistry (Padwa, ed.), Wiley, N.Y., 1984; Kanemasa and Tsuge, *Heterocycles* 1990, 30, 719). The requisite nitrile oxides are in turn prepared from commercially available precursors or appropriately substituted aldehydes via the intermediate oxime.

Scheme 1 illustrates one synthetic sequence which will provide compounds of Formula (I) of this invention.

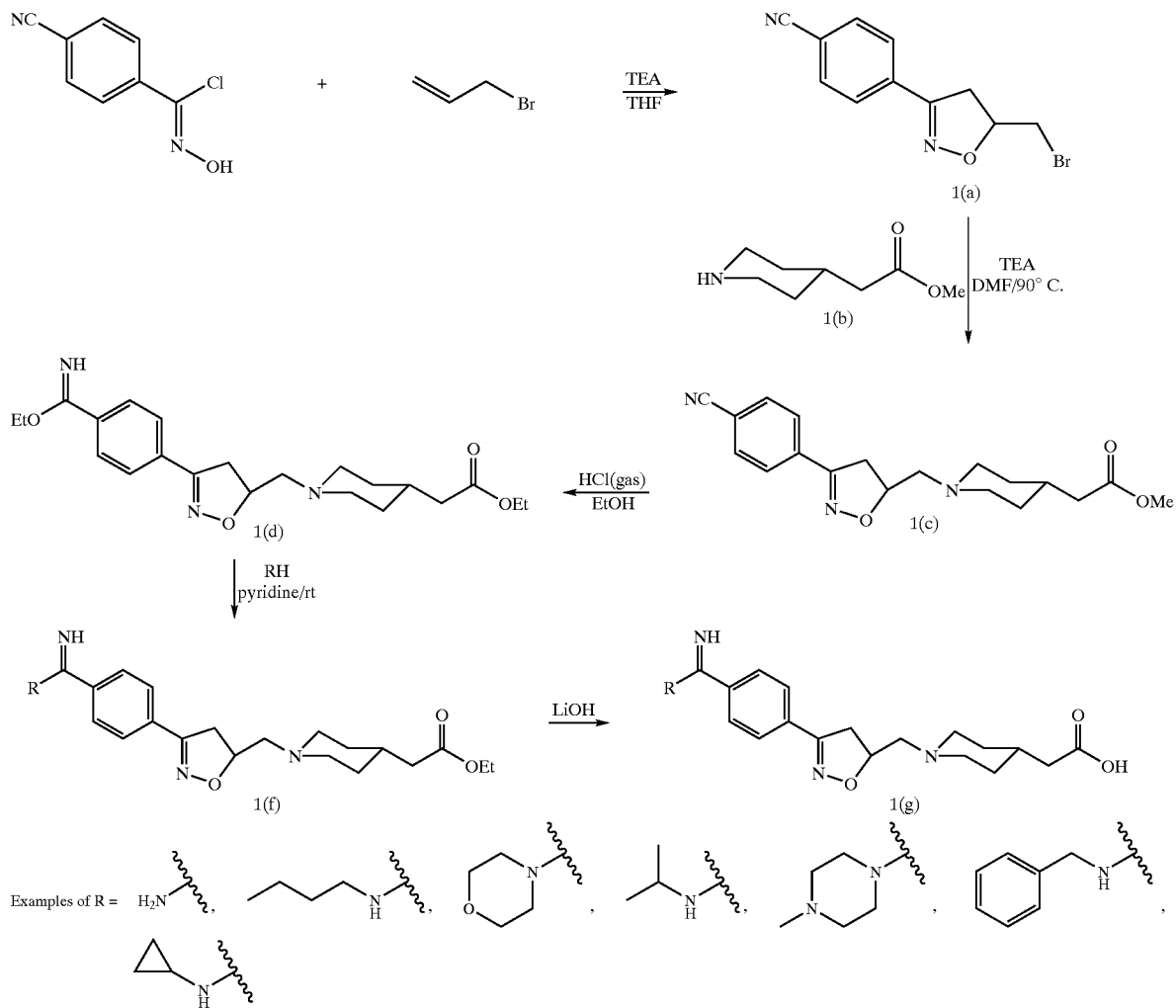

Treatment of commercially available allyl bromide with 4-cyanobenzaldehyde chlorooxime in a suitable solvent, such as tetrahydrofuran or dichloromethane in the presence of a mild base, such as sodium bicarbonate or triethylamine, affords the isoxazoline intermediate, 1(a). Coupling of 1(a) with precursor 1(b) was carried out with triethylamine or sodium hydride and dimethyl formamide as a solvent to give compound 1(c) (for review of this type of reaction, see The Chemistry of the Amino Group (Patai, ed.), Wiley, N.Y., 1968; The Acyclic Aliphatic Tertially Amines (Spialter and Pappalardo), Macmillan, N.Y., 1965). A Pinner synthesis was performed on intermediate 1(c) to yield 1(d). Further treatment of 1(d) with different appropriate amines provides 1(f). Finally, deprotection of compound 1(f) was carried out using standard methods of removal of carboxy protecting group to provide target compounds of formula 1(g).

Scheme 2

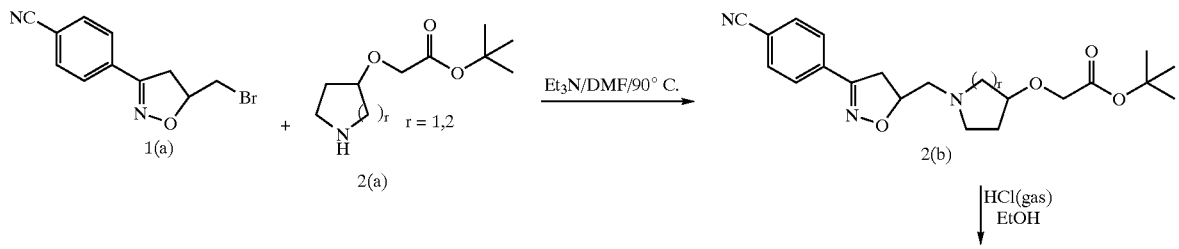

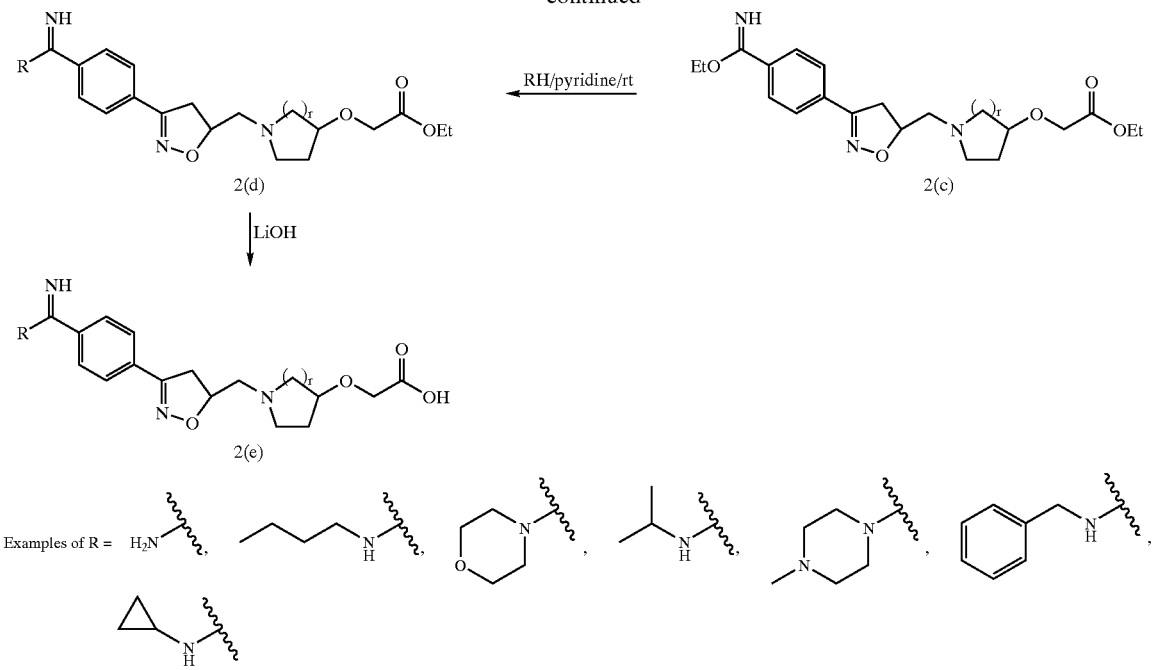

Compounds of Formula (I), wherein X is 2(a) can also be prepared from cycloaddition product 1(a) as depicted in Scheme 2. In a similar manner as described earlier, coupling of 1(a) and 2(a) can be achieved upon heating with a suitable base such as cesium carbonate or triethylamine in dimethyl formamide. Treatment of compound 2(b) with gaseous hydrogen chloride, followed by the addition of several different amines affords 2(d). Subsequent removal of carboxy protecting group using standard methods gives compounds of formula 2(e).

The preparations of compounds 1(b) and 2(a) are shown in Scheme 3 and 4. For intermediate 1(b) (Scheme 3), reduction of 4-pyridylacetic acid hydrochloride with 5% rhodium catalyst gives the corresponding piperidyl derivative. Further treatment of 4-piperidylacetic acid hydrochloride with thionyl chloride in the presence of methanol yields the desired compound 1(b). Intermediate 2(a) (Scheme 4) can be obtained following a three-step procedure. Either 3-pyrrolidinol or 4-piperidinol can be treated with benzyl chlorofomate to give the corresponding amine protected derivatives. Subsequent treatment with tert-butyl bromoacetate and hydrogenation provides compounds of formula 2(a).

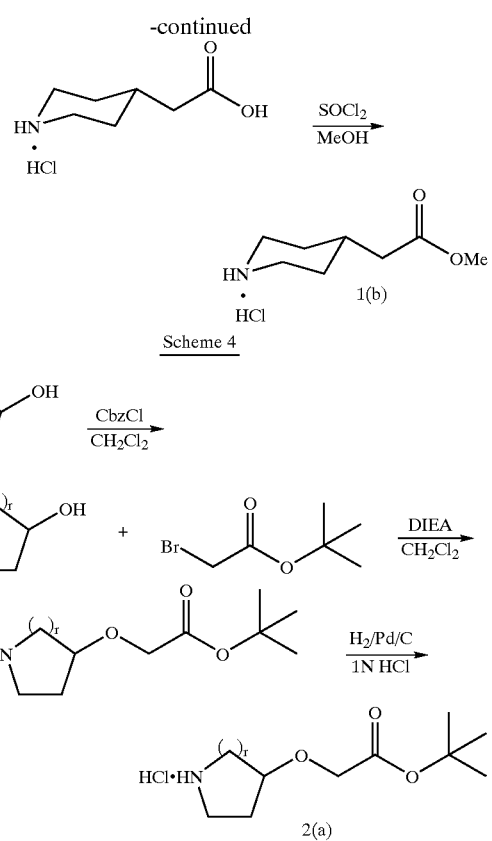

Additional isoxazoline compounds useful in the present invention can be prepared as outlined in Scheme 5 wherein 1,3-dipolar cycloaddition is carried out using commercially available methyl acrylate as a dipolarophile. Treatment of methyl acrylate with 4-cyanobenzaldehyde chlorooxime in a suitable solvent such as tetrahydrofuran or dichloromethane, in the presence of a mild base, such as sodium bicarbonate or triethylamine, provides isoxazoline intermediate 10(a). Subsequent hydrolysis of the methyl ester using conventional methods known to one skilled in the art of organic synthesis gives the corresponding acid 10(b). Coupling of compound 10(b) to either intermediate 1(b) or 2(a) (see Scheme 3) affords 10(c).

The coupling is carried out using any of the many methods for the formation of amide bonds known to one skilled in the art of organic synthesis. These methods include but are not limited to conversion of the acid to the corresponding procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic amido ester) method, carbonyldiimidazole method, or coupling with phosphorus reagents such as BOP reagent. Some of these methods (especially the carbodiimide) can be enhanced by addition of 1-hydroxybenzotriazole. Compound 10(c) was treated with gaseous hydrogen chloride in an appropriate solvent such as ethanol to yield 10(d). Further treatment of compound 10(d) with an appropriate amine in a suitable solvent such as pyridine or methanol provides 10(e). Deprotection of compound 10(e) is carried out using standard methods of removal of carboxy protecting group to give target compounds of formula 10(f).

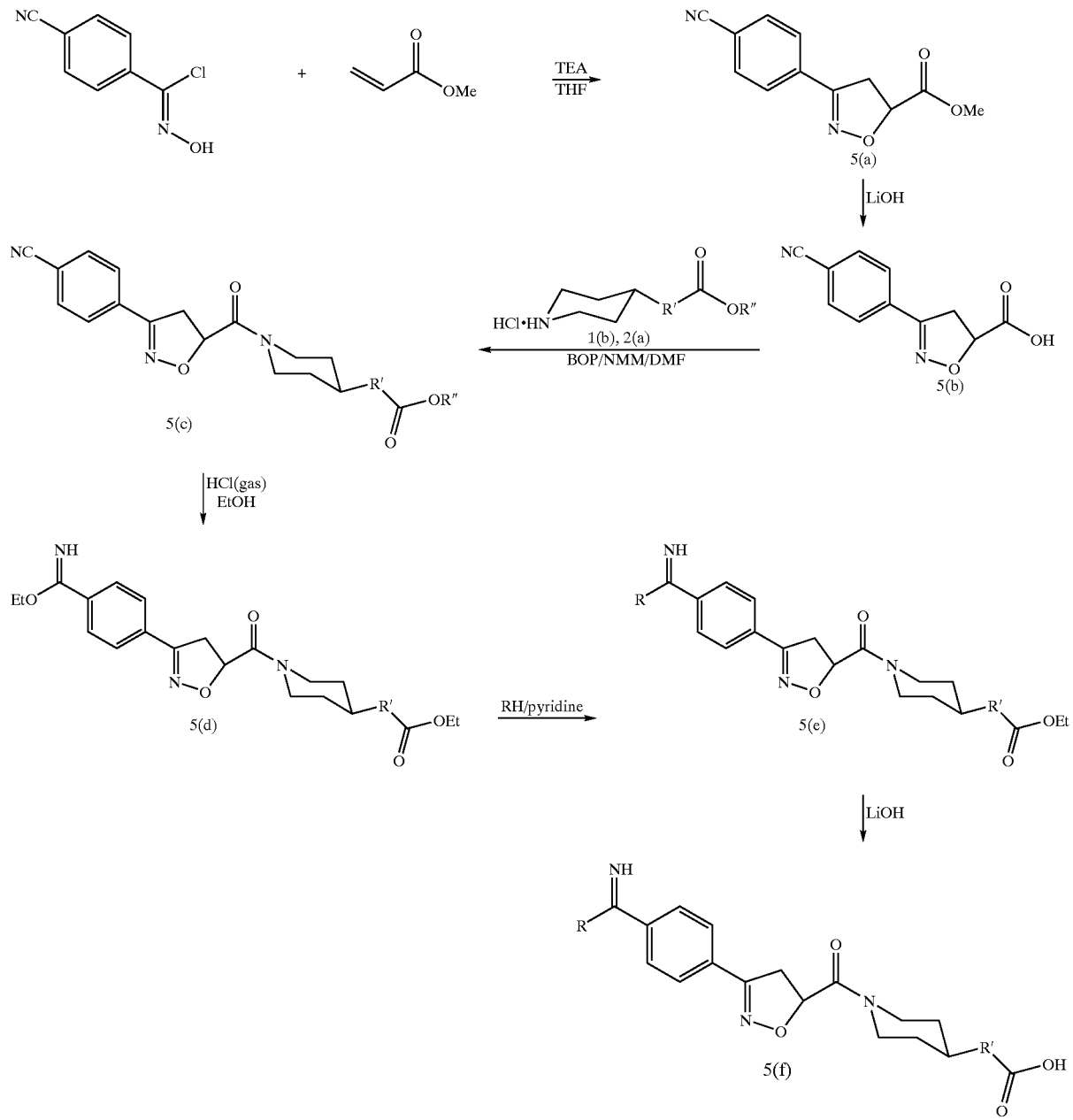

Scheme 5

Examples of:
R' = CH₂, OCH₂
R" = Me, t-Bu

R =
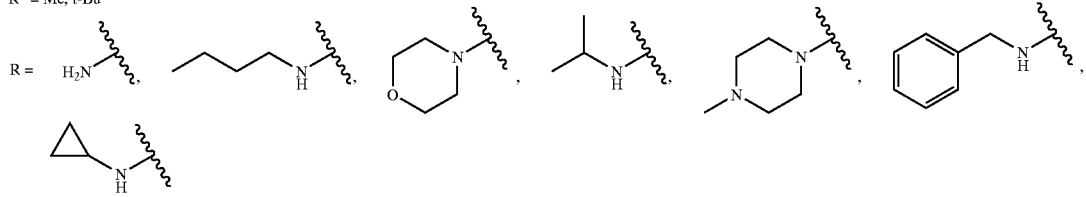

The detailed processes for preparing the compounds of Formula (I) are illustrated by the following examples. It is, however, understood that this invention is not limited to the specific details of these examples. Melting points (mp) are uncorrected. Proton nuclear magnetic resonance spectra (NMR) were measured in chloroform-d (CDCl₃) unless otherwise specified and the peaks are reported in parts per million (ppm) downfield from tetramethylsilane (TMS). the coupling patterns are reported as follows: s, singlet; d, doublet; t, triplet; q, quartet; m, multiplet; bs, broad singlet; bm, broad multiplet. Infrared spectra are reported in reciprocal centimeters (cm⁻¹). All final compounds gave satisfactory nmr and HRMS data an d were anlayzed to be >98% pure by reverse ph ase analytical HPLC.

EXAMPLES

Example 1

[[1-[3-[4-[(4-Morpholinyl)iminomethyl]phenyl] isoxazolin-5-ylmethyl]-4-piperidinyl]oxy]acetic Acid Part A: 4-[5-(Bromomethyl)-4,5-dihydro-3-isoxazolyl]-benzonitrile; 1(a):

To a solution of 4-cyanobenzaldehyde chlorooxime (10 g, 55 mmol) and allyl bromide (5.8 mL, 66 mmol ) in tetrahydrofuran (150 mL) was added triethylamine (9.3 mL, 66 mmol) dropwise over 1 h. After stirring for 10 hours at room temperature, the precipitate was filtered through a sinter glass funnel and the filtrate was evaporated to dryness. The solid residue was purified by column chromatography with silica gel, eluting with 3:7 EtOAc:Hex to give 12.6 g of 1(a) as a white powder (86% yield). $^1$H-NMR (CDCl₃) δ 7.8 (d, 2H), 7.7 (d, 2H), 5.1 (m, 1H), 3.5 (m, 2H), 3.4 (m, 2H).

Part B: 1,1-Dimethylethyl (4-piperidinyloxy)acetate Hydrochloride; 2(a):

To a mixture of 4-piperinol (10.0 g, 98.8 mmol) and triethylamine (13.6 mL, 98.8 mmol) in dichloromethane (100 mL) at 0° C. was added dropwise, via an additional funnel, benzyl chloroformate. After stirring for 18 hours at room temperature, the precipitate was filtered off and the filtrate was concentrated to an oily residue. The oily residue was diluted with water and 1N HCl and extracted three times with ethyl acetate, dried (MgSO₄), filtered and concentrated under vacuo to yield 18.1 g of the protected amine compound (77.9% yield). The pale, clear oil was then dissolved in dichloromethane (150 mL) and treated with diisopropylethylamine (14.9 g, 115 mmol) and tert-butyl bromoacetate (17.9 g, 92.0 mmol). After stirring for 18 hours at room temperature, the mixture was diluted with dichloromethane and washed once with water and once with brine, dried (MgSO₄), filtered and evaporated to dryness. The oily residue was purified by flash column chromatography eluting with 1:5 EtOAc:Hex, followed by 1:3 EtOAc:Hex to give 23.8 g of the coupled product (89.0% yield). MS calcd. for C₁₉H₂₇NO₅ ([M+Na]): 372.4; found: 372.2. A mixture of the coupled product (23.7 g, 67.9 mmol), methanol (150 mL) and 1N HCl (68 mL, 68.0 mmol) was evacuated and flushed with nitrogen. The resulting solution was treated with hydrogen gas for 4 hours before it was filtered through a pad of celite, concentrated and evaporated to dryness to afford 15.3 g of 2(a) as a white solid (89.0% yield). MS calcd. for C₁₁H₂₂NO₃ ([M+H]⁺): 216.3; found: 216.2.

Part C: Methyl 1-[[3-(4-Cyanophenyl)4,5-dihydro-5-isoxazolyl]methyl]-4-piperidineacetate: 2(b):

To a solution of 2(a) (5.31 g, 21.1 mmol) in dimethyl formamide (50 mL) was added triethylamine (5.4 mL, 42.2 mmol). After stirring for 15 min at room temperature, the precipitate was filtered off and the filtrate was added to a solution of 1(a) (5.60 g, 21.1 mmol) in 50 mL of dimethyl formamide. The resulting mixture was allowed to stir at 90° C. for two days. The cooled mixture was diluted with water (100 mL) and extracted 3 times with 50 mL ethyl acetate. The combined organic extracts were washed twice with water and once with brine, dried (MgSO₄), filtered, and concentrated under vacuo. The solid residue was chromatographed over silica gel, eluting with 1:3 acetonitrile:dichloromethane followed by 1:1 acetonitrile:dichlromethane to provide 3.65 g of 2(b) as a pale yellow solid (43.3% yield). $^1$H-NMR (CDCl₃) δ 7.8 (d, 2H), 7.7 (d, 2H), 4.9 (m, 1H), 4.0 (s, 2H), 3.4 (m, 2H), 3.2 (m, 1H), 2.8 (bm, 2H), 2.6 (m, 2H), 2.3 (bm, 2H), 1.9 (bm, 2H), 1.7 (bm, 2H), 1.5 (s, 9H); MS calcd. for C₂₂H₃₀N₃O₄ ([M+H]⁺): 400.5; found: 400.3.

Part D: Ethyl 1-[[3-[4-(Ethoxyiminomethyl)phenyl]-4,5-dihydro-5-isoxazolyl]methyl]-4-piperidineacetate; 2(c):

Hydrogen chloride gas was bubbled to a magnetically stirred solution of compound 2(b) (1.64 g, 4.42 mmol) in 60 mL of ethanol, at 0° C., for 1 hour. The mixture was warmed to room temperature and stirred for an additional 3 hours before excess ethanol was evaporated off to yield 2(c) as a foamy solid. Compound 2(c) was directly used in the next step without any purification. $^1$H-NMR (CDCl₃) δ 12.2 (bs, 1H), 11.6 (bm, 2H), 8.3 (d, 2H), 7.8 (d, 2H), 5.6 (bm, 1H), 4.9 (bm, 2H), 4.2 (q, 2H), 4.1 (s, 2H), 3.7 (bm, 4H), 3.5 (bm, 1H), 3.3 (bm, 4H), 2.4 (bm, 2H), 2.1 (bm, 2H). 1.6 (t, 3H), 1.2 (t, 3H).

Part E: Ethyl 1-[[4,5-Dihydro-3-[4-[(4-morpholinyl)-iminomethyl]phenyl]-5-isoxazolyl]methyl]-4-piperidineacetate; 2(d):

The intermediate 2(c) (0.46 g, 1.1 mmol) in 15 mL of 2:1 pyridine:ethanol was treated with morpholine (0.29 mL, 3.3 mmol) and the mixture was stirred at room temperature for 18 hours. The excess solvents were evaporated off to give an oily residue, which was purified by flash column chromatography (silica gel column/2:8 MeOH:CHCl₃ followed by 3:7:0.2 MeOH:CHCl₃:NH₄OH) to afford 376 mg of 2(d) as a pale yellow foam (74.5% yield). $^1$H-NMR (CDCl₃) δ 7.8 (d, 2H), 7.6 (d, 2H), 4.9 (m, 1H), 4.2 (q, 2H), 4.1 (s, 2H), 3.9 (bm, 2H), 3.8 (bm, 4H), 3.4 (m, 2H), 3.2 (m, 1H), 3.1 (bm, 2H), 2.8 (bm, 2H), 2.6 (m, 2H), 2.3 (bm, 2H), 1.9 (bm, 2H), 1.7 (bm, 2H), 1.3 (t, 3H). MS calcd. for $C_{24}H_{35}N_4O_5$ ([M+H]$^+$): 459.6; found: 459.3.

Part F: [[1-[[4,5-Dihydro-3-[4-[(4-morpholinyl)-iminomehyl]phenyl]-5-isoxazolyl]methyl]-4-piperidinyl]-oxy]acetic acid:

Compound 2(d) (376 mg, 0.820 mmol) in 12.0 mL of 2:1 THF:H$_2$O was treated with lithium hydroxide monohydrate (138 mg, 3.28 mmol) and the mixture was stirred at room temperature for 5 min. The mixture was quenched with 3.30 mL of 1N HCl and the excess solvents were evaporated off. The residue was purified by preparative HPLC (C18, gradient from 100% A to 100% B: A=90/10/0.05 H$_2$O/CH$_3$CN/TFA; B=10/90/0.05 90/10/0.05 H$_2$O/CH$_3$CN/TFA) to provide the title compound (285 mg, 52.8%). $^1$H-NMR (DMSO-D$_6$) δ 9.7 (bs, 1H), 9.4 (bs, 1H), 7.8 (d, 2H), 7.7 (d, 2H), 5.2 (m, 1H), 4.1 (bs, 2H), 3.7 (bm, 9H), 3.3 (bm, 8H), 2.2 (bm, 1H), 1.9 (bm, 2H), 1.7 (bm, 1H). MS calcd. for $C_{22}H_{31}N_4O_5$ ([M+H]$^+$): 431.5; found: 431.3.

The following compounds were prepared in procedures (see Scheme 2) similar to those above starting from compound 1(a).

Example 2

[[1-[3-[4-[(4-Methyl-1-piperazinyl)iminomethyl] phenyl]-isoxazolin-5-ylmethyl]-4-piperidinyl]oxy] acetic Acid $^1$H-NMR (DMSO-D$_6$) δ 10.0 (bs, 1H), 9.7 (bs, 1H), 7.9 (d, 2H), 7.7 (d, 2H), 5.2 (bm, 1H), 4.1 (bs, 2H), 3.7 (m, 2H), 3.5 (bm, 5H), 3.2 (bm, 10H), 2.8 (s, 3H), 2.1 (bm, 1H), 1.9 (bm, 2H), 1.7 (bm, 1H). MS calcd. for $C_{23}H_{33}N_5O_4$ ([M+H]$^+$): 444.6; found: 444.4.

Example 3

[[1-[3-[4-[(Butylamino)iminomethyl]phenyl] isoxazolin-5-ylmethyl]-4-piperidinyl]oxy]acetic Acid $^1$H-NMR (DMSO-D$_6$) δ 9.9 (bt, 1H), 9.5 (bs, 1H), 9.1 (bs, 1H), 7.9 (d, 2H), 7.8 (d, 2H), 5.3 (bm, 1H), 4.1 (bs, 2H), 3.8 (bm, 2H), 3.6 (bm, 2H), 3.3 (bm, 7H), 2.2 (bm, 1H), 2.0 (bm, 2H), 1.7 (m, 3H), 1.4 (m, 2H), 0.9 (t, 3H). MS calcd. for $C_{23}H_{33}N_4O_4$ ([M+H]$^+$): 417.5; found: 417.3.

Similarly prepared from 1(a) and 1(b) were the following (see Scheme 2):

Example 4

1-[3-[4-(Aminoiminomethyl)phenyl]isoxazolin-5-yl-methyl]-4-piperidinylacetic Acid $^1$H-NMR (DMSO-D$_6$) δ 9.7 (bs, 1H), 9.4 (bd, 2H), 7.9 (m, 4H), 5.2 (bm, 1H), 3.7 (m, 1H), 3.5 (bm, 2H), 3.3 (bm, 3H), 3.0 (bm, 2H), 2.2 (d, 2H), 1.9 (bm, 3H), 1.5 (bm, 2H). MS calcd. for $C_{18}H_{24}N_4O_3$ ([M+H]$^+$): 345.4; found: 345.3.

Example 5

1-[3-[4-[(n-Butylamino)iminomethyl]phenyl] isoxazolin-5-ylmethyl]-4-piperidinylacetic Acid $^1$H-NMR (DMSO-D$_6$) δ 9.9 (bt, 2H), 9.5 (bs, 1H), 9.1 (bs, 1H), 7.8 (m, 4H), 5.2 (bm, 1H), 3.7 (m, 1H), 3.5 (bm, 2H), 3.3 (bm, 5H), 3.0 (bm, 2H), 2.2 (d, 2H), 1.9 (bm, 3H), 1.5 (bm, 6H), 0.9 (t, 3H). MS calcd. for $C_{22}H_{32}N_4O_3$ ([M+H]$^+$): 401.5; found: 401.0.

Example 6

1-[3-[4-[(4-Morpholinyl)iminomethyl]phenyl] isoxazolin-5-ylmethyl]-4-piperidinylacetic Acid $^1$H-NMR (DMSO-D$_6$) δ 9.9 (bs, 1H), 9.6 (bs, 1H), 9.4 (bs, 1H), 3.8 (bm, 5H), 3.6 (bm, 2H), 3.5 (bm, 2H), 3.3 (bm, 5H), 3.0 (bm, 2H), 2.2 (d, 2H), 1.9 (bm, 3H), 1.5 (bm, 2H). MS calcd. for $C_{22}H_{30}N_4O_4$ ([M+H]$^+$): 415.5; found: 415.3.

Example 7

1-[3-[4-[(4-Methyl-1-piperazinyl)iminomethyl] phenyl]-isoxazolin-5-ylmethyl]-4-piperidinylacetic Acid $^1$H-NMR (DMSO-D$_6$) δ 10.0 (bs, 1H), 9.9 (bs, 1H), 9.7 (bs, 1H), 7.9 (d, 2H), 7.7 (d, 2H), 5.2 (bm, 1H), 3.7 (m, 1H), 3.5 (bm, 7H), 3.3 (bm, 6H), 3.0 (bm, 2H), (2.8 (s, 3H), 2.2 (d, 2H), 1.9 (bm, 3H), 1.5 (bm, 2H). MS calcd. for $C_{23}H_{33}N_5O_3$ ([M+H]$^+$): 428.5; found: 428.0.

Example 10

1-[3-[4-[(Butylamino)iminomethyl]phenyl] isoxazolin-5-ylcarbonyl]-4-piperidineacetic Acid Part A: Methyl 3-(4-Cyanophenyl)-4-5-dihydro-5-isoxazolecarboxylate; 10(a):

To a solution of 4-cyanobenzaldehyde chlorooxime (7.2 g, 40 mmol) and methyl acrylate (3.4 g, 40 mmol) in tetrahydrofuran (100 mL) was added triethylamine (4.1 g, 41 mmol) dropwise over 1 h. After stirring for 18 hours at room temperature, the solvent was removed and then it was diluted with dichloromethane, washed with water, dried (MgSO$_4$), filtered and concentrated under vacuo to afford 7.4 g of 10(a) as a white powder (80.4% yield). $^1$H-NMR (DSO-D$_6$) δ 8.0 (d, 2H), 7.9 (d, 2H), 5.2 (dd, 1H), 3.8 (m, 2H), 3.7 (s, 3H).

Part B: 3-(4-Cyanophenyl)-4 5-dihydro-5-isoxazolecarboxylic Acid; 10(b):

Compound 10(a) (3.0 g, 13 mmol) in 30 mL of 1:1 THF:H$_2$O was treated with lithium hydroxide monohydrate (1.1 g, 26 mmol) and the mixture was stirred at room temperature for 4 hours. The mixture was acidified and extracted 3 times with 1:3 isopropanol:chloroform, dried (MgSO$_4$), filtered and evaporated to dryness to yield 2.2 g of 10(b) as a white solid (78.3% yield). $^1$H-NMR (DMSO-D$_6$) δ 7.9 (d, 2H), 7.8 (d, 2H), 5.2 (dd, 1H), 3.7 (m, 2H).

Part C: Methyl 4-Piperidylacetate Hydrochloride; 1(b):

To a mixture of 4-pyridylacetic acid (10 g, 58 mmol) in ethanol (60 mL), water (20 mL) and acetic acid (5 mL) was added (5%) Rh/Al catalyst (2 g, 20% by weight). After stirring for 1.5 days under hydrogen gas and a pressure of 50 psi, the solution was filtered through a pad of celite and the solvents were evaporated off. The solid residue was then redissolved in methanol (100 mL) and cooled to 0° C. Thionyl chloride (5.0 mL, 63 mmol) was added dropwise to the cooled solution. The resulting mixture was warmed to room temperature and was further stirred for 3 hours before excess methanol and thionyl chloride were evaporated off to afford 10.4 g of 1(b) (93% yield). $^1$H-NMR (D$_2$O) δ 3.2 (bm, 2H), 2.8 (bm, 2H), 2.2 (d, 2H), 1.8 (bm, 3H), 1.3 (bm, 2H).

Part D: Methyl 1-[[3-[4-Cyanophenyl]-4.5-dihydro-5-isoxazolyl]carbonyl]-4-piperidineacetate; 10(c):

A solution of 10(b) (840 mg, 3.88 mmol), BOP Reagent (2.06 g, 4.66 mmol) and 1(b) (898 mg, 4.66 mmol) in dimethyl formamide was treated with 4-N-Methylmorpholine (1.27 mL, 11.7 mmol). After stirring at room temperature for 24 hours, the mixture was diluted with water and extracted 3 times with ethyl acetate. The combined organic extracts were washed twice with water and once with brine, dried (MgSO$_4$), filtered, and concentrated under vacuo to give an oily residue. Purification by column chromatography was carried out with silica gel and eluting with 100% ethyl acetate to provide 1.14 g of 10(c) as a foamy solid (82.7% yield). $^1$H-NMR (CDCl$_3$) δ 7.8 (d, 2H), 7.7 (d, 2H), 5.4 (m, 1H), 4.6 (bm, 1H), 4.2 (m, 2H), 3.7 (s, 3H), 3.3 (m, 1H), 3.1 (m, 1H), 2.7 (m, 1H), 2.3 (d, 2H), 2.1 (m, 1H), 1.8 (bm, 2H), 1.3 (m, 2H). MS calcd. for C$_{19}$H$_{21}$N$_3$O$_4$ ([M−H]$^+$): 354.4; found: 354.2.

Part E: Ethyl 1-[[3-(4-(Ethoxyiminomethyl)phenyl]-4,5-dihydro-5-isoxazolyl]carbonyl]-4-piperidineacetate; 10(d):

A suspension of 10(c) (1.1 g, 3.2 mmol) in 60 mL of ethanol was treated with hydrogen gas for 1 hour at 0° C. The solid dissolved in ethanol as hydrogen chloride gas was bubbled to the mixture. The mixture was warmed to room temperature and stirred for an additional 3 hours. The excess ethanol was removed under vacuum to provide a foamy, off-white solid. $^1$H-NMR (CDCl$_3$) δ 12.7 (bs, 1H), 12.0 (bs, 1H), 8.4 (d, 2H), 7.8 (d, 2H), 5.4 (m, 1H), 4.9 (q, 2H), 4.6 (bm, 1H), 4.2 (m, 2H), 3.3 (bm, 2H), 2.7 (bm, 1H), 2.3 (m, 2H), 2.1 (m, 1H), 1.8 (bm, 2H), 1.6 (t, 3H), 1.3 (bm, 2H), 1.2 (t, 3H).

Part F: Ethyl 1-[[3-[4-(Butylamino)iminomethyl]-phenyl]-4,5-dihydro-5-isoxazolyl]carbonyl]-4-piperidineacetate; 10(e):

To a solution of 10(d) (349 mg, 0.840 mmol) in 10.0 mL of pyridine was added n-butylamine (167 μL, 1.69 mmol). After stirring for 24 hours at room temperature, the solvent was removed under vacuum and the the oily residue was purified by column chromatography eluting with 1:9 MeOH:CHCl$_3$, followed by 1:4:0.05 MeOH:CHCl$_3$:NH$_4$OH to yield 309 mg of 10(e) as a white foam (83.1% yield). $^1$H-NMR (CDCl$_3$) δ 7.8 (d, 2H), 7.6 (d, 2H), 5.4 (bm, 1H), 4.4 (bm, 1H), 4.1 (m, 3H), 3.7 (bm, 1H), 3.4 (bm, 2H), 3.1 (bm, 1H), 2.6 (bm, 1H), 2.2 (bm, 2H), 2.0 (bm, 1H), 1.8 (bm, 2H), 1.6 (bm, 2H), 1.3 (m, 4H), 1.2 (t, 3H), 0.8 (t, 3H). MS calcd. for C$_{24}$H$_{35}$N$_4$O$_4$ ([M−H]$^+$): 443.6; found: 443.4.

Part G: 1-[[3-[4-(Butylamino)iminomethyl]phenyl]-4,5-dihydro-5-isoxazolyl]carbonyl]-4-piperidineacetic Acid:

Compound 10(e) (295 mg, 0.6670 mmol) in 9.0 mL of 2:1 THF:H$_2$O was treated with lithium hydroxide monohydrate (112 mg, 3.28 mmol) and the mixture was stirred at room temperature for 4 hours. The mixture was quenched with 2.7 mL of 1N HCl and the excess solvents were evaporated off. The residue was purified by preparative HPLC (C18, gradient from 100% A to 100% B: A=90/10/0.05 H$_2$O/CH$_3$CN/ TFA; B=10/90/0.05 90/10/0.05 H$_2$O/CH$_3$CN/TFA) to provide the title compound (119 mg, 43%). $^1$H-NMR (DMSO-D$_6$) δ 9.8 (t, 1H), 9.5 (s, 1H), 9.0 (s, 1H), 7.9 (d, 2H), 7.8 (d, 2H), 5.7 (m, 1H), 4.3 (bm, 1H), 4.0 (bm, 1H), 3.9 (m, 1H), 3.6 (bm, 1H), 3.4 (q, 2H), 3.1 (bm, 1H), 2.2 (d, 2H), 2.0 (bm, 1H), 1.7 (bm, 4H), 1.4 (m, 2H), 1.2 (bm, 2H), 0.9 (t, 3H). MS calcd. for C$_{22}$H$_{31}$N$_4$O$_4$ ([M+H]$^+$): 415.5; found: 415.3. The following compounds were prepared similar to those above starting from compounds 2(a) and 10(b) following procedures of Scheme 5.

Example 11

[[1-[3-[4-Aminoiminomethylphenyl]isoxazolin-5-ylcarbonyl]-4-piperidinyl]oxy]acetic Acid $^1$H-NMR (DMSO-D$_6$) δ 9.32 (br s, 1H), 9.11 (br s, 1H), 7.89 (d, J=8.6 Hz, 2H), 7.85 (d, J=8.6 Hz, 2H), 6.44 (br s, 2H), 5.65 (dd, J=7.3, 11.3 Hz, 1H), 3.83 (dd, J=7.3, 17.3 Hz, 2H), 3.56 (dd, J=11.3, 17.3 Hz, 4H), 3.33 (obscured m, 1H), 1.98–1.78 (m, 2H), 1.60–1.30 (m, 2H); MS (ESI) 375 (M+H).

Example 12

[[1-[3-[4-[(n-Butylamino)iminomethyl]phenyl] isoxazolin-5-ylcarbonyl]-4-piperidinyl]oxy]acetic Acid $^1$H-NMR (DMSO-D$_6$) δ 9.8 (m, 1H), 9.4 (bs, 1H), 9.0 (bs, 1H), 7.9 (d, 2H), 7.8 (d, 2H), 5.7 (m, 1H), 4.1 (s, 2H), 3.9–3.5 (m, 5H), 3.4 (m, 2H), 3.3 (bm, 2H), 1.9 (bm, 2H), 1.7 (m, 2H), 1.6 (bm, 2H), 1.4 (m, 2H), 1.0 (t, 3H). MS calcd. for C$_{22}$H$_{31}$N$_4$O$_5$ ([M+H]$^+$): 431.5; found: 431.3.

Example 13

[[1-[3-[4-[[(1-Methylethyl)amino]iminomethyl] phenyl]-isoxazolin-5-ylcarbonyl]-4-piperidinyl]oxy] acetic Acid $^1$H-NMR (DMSO-D$_6$) δ 9.6 (bd, 1H), 9.4 (bs, 1H), 9.0 (bs, 1H), 7.9 (d, 2H), 7.8 (d, 2H), 5.7 (m, 1H), 4.1 (s, 2H), 4.0 (bm, 1H), 3.9–3.6 (m, 5H), 3.3 (bm, 2H), 1.9 (bm, 2H), 1.6 (bm, 2H), 1.3 (d, 6H). MS calcd. for C$_{21}$H$_{29}$N$_4$O$_5$ ([M+H]$^+$): 417.4; found: 417.2.

Example 14

[[1-[3-[4-[[(Phenylmethyl)amino]iminomethyl] phenyl]-isoxazolin-5-ylcarbonyl]-4-piperidinyl]oxy] acetic Acid $^1$H-NMR (DMSO-D$_6$) δ 10.3 (m, 1H), 9.6 (bs, 1H), 9.3 (bs, 1H), 7.9 (d, 2H), 7.85 (d, 2H), 7.6 (m, 5H), 5.7 (m, 1H), 4.7 (d, 2H), 4.1 (s, 2H), 3.9–3.5 (m, 7H), 3.3 (bm, 2H), 1.9 (bm, 2H), 1.6 (bm, 2H). MS calcd. for C$_{25}$H$_{29}$N$_4$O$_5$ ([M+H]$^+$): 465.5; found: 465.4.

Example 15

[[1-[3-[4-[(4-Morpholinyl)iminomethyl]phenyl] isoxazolin-5-ylcarbonyl]-4-piperidinyl]oxy]acetic Acid $^1$H-NMR (DMSO-D$_6$) δ 9.6 (bs, 1H), 9.3 (bs, 1H), 7.9 (d, 2H), 7.7 (d, 2H), 5.7 (m, 1H), 4.1 (s, 2H), 3.9–3.5 (m, 11H), 3.4 (m, 2H), 3.3 (bm, 2H), 1.9 (bm, 2H), 1.6 (bm, 2H). MS calcd. for C$_{22}$H$_{29}$N$_4$O$_6$ ([M+H]$^+$)445.5; found: 445.3.

Example 16

[[1-[3-[4-[(4-Methyl-1-piperazinyl)iminomethyl] phenyl]-isoxazolin-5-ylcarbonyl]-4-piperidinyl]oxy] acetic Acid $^1$H-NMR (DMSO-D$_6$) δ 9.9 (bs, 1H), 9.6 (bs, 1H), 8.0 (d, 2H), 7.7 (d, 2H), 5.7 (m, 1H), 4.0 (s, 2H), 3.9–3.5 (m, 11H), 3.4 (m, 2H), 3.3 (bm, 2H) 2.8(bs, 3H), 1.9 (bm, 2H), 1.6 (b m, 2H). MS calcd. for C$_{23}$H$_{32}$N$_5$O$_5$ ([M+H]$^+$) 458.5; found: 458.3.

Example 17

[[1-[3-[4-[(Cyclopropylamino)iminomethyl]phenyl] isoxazolin-5-ylcarbonyl]-4-piperidinyl]oxy]acetic Acid $^1$H-NMR (DMSO-D$_6$) δ 10.0 (bs, 1H), 9.7 (bs, 1H), 9.2 (bs, 1H), 7.9 (d, 2H), 7.8 (d, 2H), 5.7 (m, 1H), 4.0 (s, 2H), 3.9–3.5 (m, 5H), 3.3 (bm, 2H), 2.8 (m, 1H), 1.9 (bm, 2H), 1.6 (bm, 2H) 1.0 (m, 2H), 0.8 (m, 2H). MS calcd. for C$_{21}$H$_{27}$N$_4$O$_5$ ([M+H]$^+$): 415.4; found: 415.2.

TABLE 1

[Structure: compound with R²R²ᵇN-phenyl-isoxazoline-CR⁵R⁶-piperidine-X-COOH]

| Ex. # | R²R²ᵇN— | R⁵, R⁶ | X | MS(M + 1) |
|---|---|---|---|---|
| 1 | morpholino | H, H | —OCH$_2$— | 431.3 |
| 2 | N-methylpiperazino | H, H | —OCH$_2$— | 444.4 |
| 3 | (n-butyl)HN— | H, H | —OCH$_2$— | 417.3 |
| 4 | H$_2$N— | H, H | —CH$_2$— | 345.3 |
| 5 | (n-butyl)HN— | H, H | —CH$_2$— | 401.0 |
| 6 | morpholino | H, H | —CH$_2$— | 415.3 |
| 7 | N-methylpiperazino | H, H | —CH$_2$— | 428.0 |
| 11 | H$_2$N— | =O | —OCH$_2$— | 375 |
| 12 | (n-butyl)HN— | =O | —OCH$_2$— | 431.3 |
| 13 | (i-propyl)HN— | =O | —OCH$_2$— | 417.2 |
| 14 | (benzyl)HN— | =O | —OCH$_2$— | 465.4 |
| 15 | morpholino | =O | —OCH$_2$— | 445.3 |
| 16 | N-methylpiperazino | =O | —OCH$_2$— | 458.3 |
| 17 | (cyclopropyl)HN— | =O | —OCH$_2$— | 415.2 |

The following Table 2 contains representative examples of the present invention. At the start of the table is one formula followed by species a through rr demonstrating the intended substitution of —NR²R²ᵇ. Each entry in the table is intended to be paired with each species at the start of the table. For example, Example 100 in Table 2 is intended to be paired with each of formulae a, b, c, d, ... through rr of Table 2, thereby representing Example 100a, 100b, 100c, etc.

TABLE 2

[General structure with R²R²ᵇN-phenyl-isoxazoline-CH$_2$-G-piperidine-N-CH(Wᵃ)-COOH]

a through rr a: H$_2$N—C(=NH)—C$_6$H$_4$—
b: CH$_3$CH$_2$CH$_2$CH$_3$-HN—C(=NH)—C$_6$H$_4$— [CH$_2$CH$_2$CH$_2$CH$_3$]
c: CH$_3$CH$_2$CH$_2$-HN—C(=NH)—C$_6$H$_4$—
d: CH$_3$CH$_2$-HN—C(=NH)—C$_6$H$_4$—
e: (CH$_3$)$_2$N—C(=NH)—C$_6$H$_4$—
f: (n-hexyl)HN—C(=NH)—C$_6$H$_4$—
g: CH$_2$(C$_6$H$_{11}$)HN—C(=NH)—C$_6$H$_4$—
h: CH$_2$(C$_3$H$_5$)HN—C(=NH)—C$_6$H$_4$—
i: CH$_2$(1-naphthyl)HN—C(=NH)—C$_6$H$_4$—
j: CH$_2$CH$_2$(2-pyridyl)HN—C(=NH)—C$_6$H$_4$—
k: CH$_2$CH$_2$(4-pyridyl)HN—C(=NH)—C$_6$H$_4$—
l: CH$_2$CH(CH$_3$)$_2$ HN—C(=NH)—C$_6$H$_4$—
m: CH$_2$CF$_3$ HN—C(=NH)—C$_6$H$_4$—
n: HC≡C— HN—C(=NH)—C$_6$H$_4$—
o: CH(C$_6$H$_5$)$_2$ HN—C(=NH)—C$_6$H$_4$—
p: CH$_2$(C$_6$H$_5$) HN—C(=NH)—C$_6$H$_4$—
q: H$_3$C—N(CH$_2$C$_6$H$_5$)—C(=NH)—C$_6$H$_4$—
r: H$_3$C—N(CH$_2$CH$_2$(C$_6$H$_5$))—C(=NH)—C$_6$H$_4$—
s: H$_3$C—N(CH$_2$CH$_2$CH$_2$CH$_3$)—C(=NH)—C$_6$H$_4$—

TABLE 2-continued
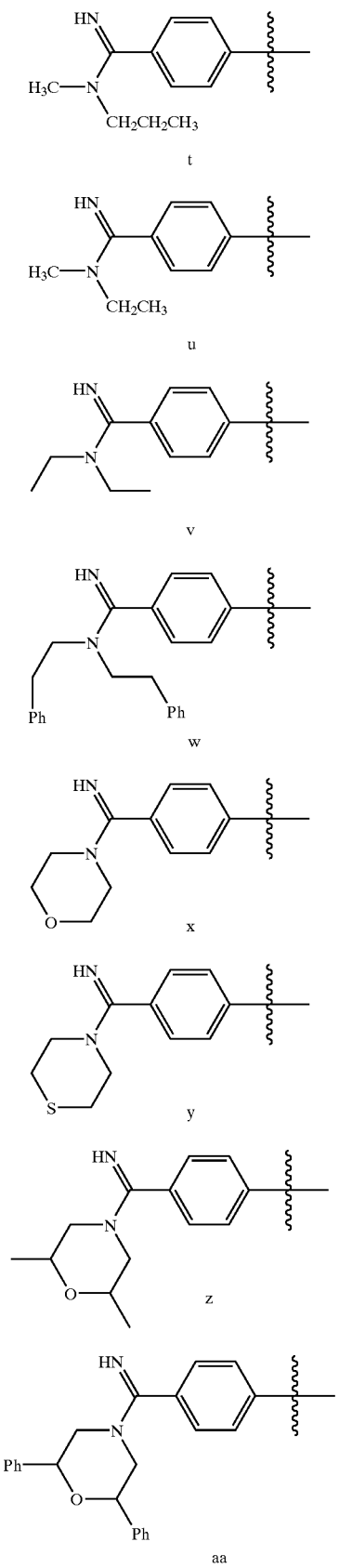
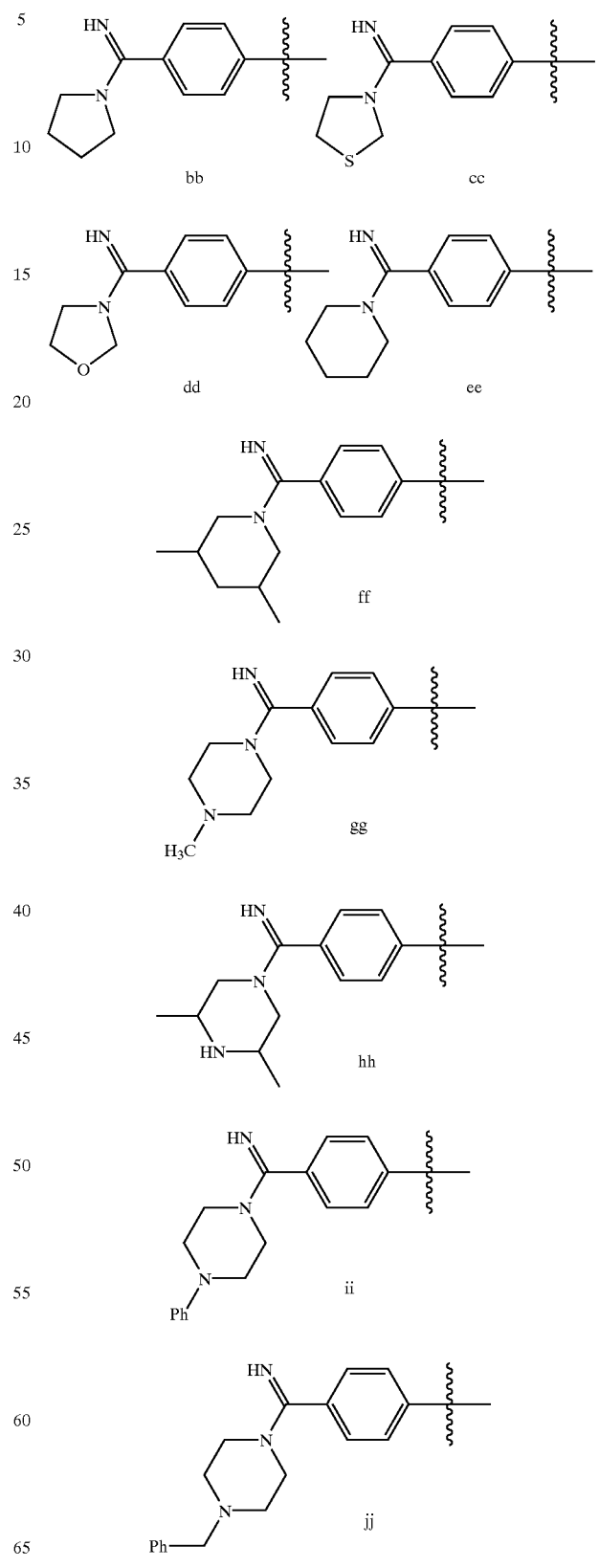

TABLE 2-continued

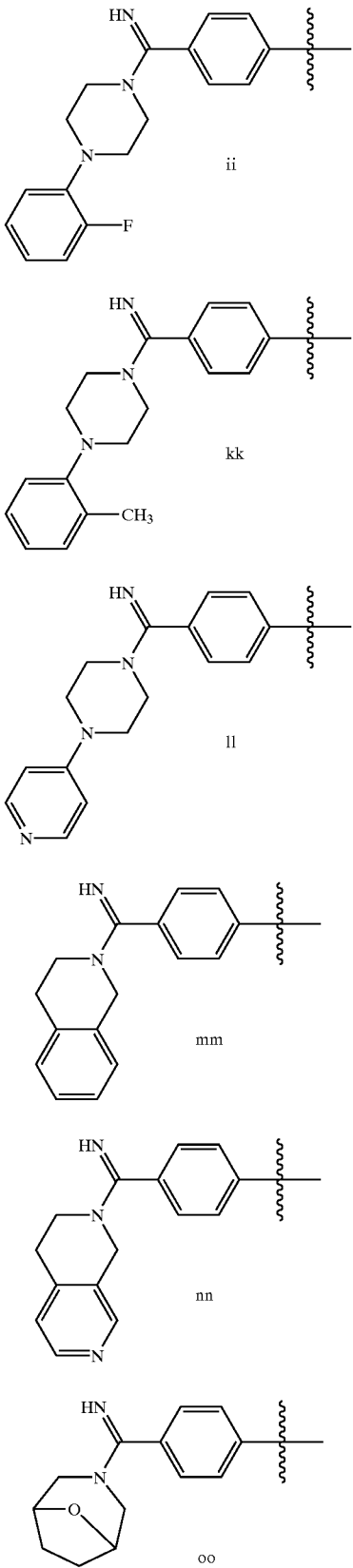

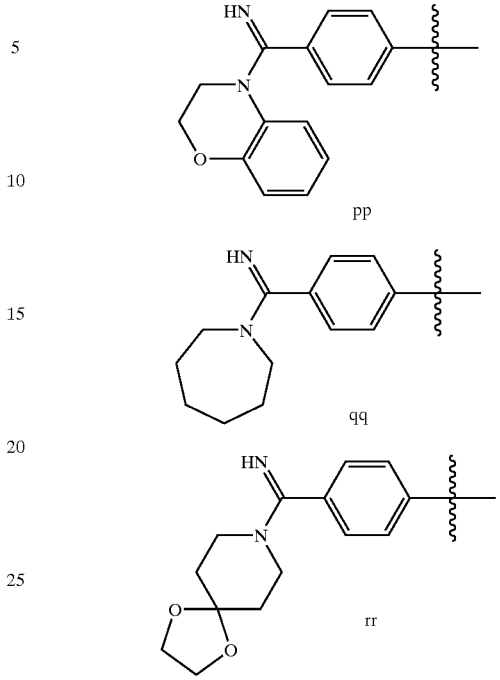

| Ex. # | R²R²ᵇN— | R⁵, R⁶ | X | Wᵃ |
|---|---|---|---|---|
| 200 | a–rr | H, H | —CH(Wᵃ)— | H— |
| 201 | a–rr | H, H | —CH(Wᵃ)— | (ethyl)SO₂NH— |
| 202 | a–rr | H, H | —CH(Wᵃ)— | (n-propyl)SO₂NH— |
| 203 | a–rr | H, H | —CH(Wᵃ)— | (n-butyl)SO₂NH— |
| 204 | a–rr | H, H | —CH(Wᵃ)— | (phenyl)SO₂NH— |
| 205 | a–rr | H, H | —CH(Wᵃ)— | (4-Me-phenyl)SO₂NH— |
| 206 | a–rr | H, H | —CH(Wᵃ)— | (3-Me-phenyl)SO₂NH— |
| 207 | a–rr | H, H | —CH(Wᵃ)— | (2-Me-phenyl)SO₂NH— |
| 208 | a–rr | H, H | —CH(Wᵃ)— | (4-Br-phenyl)SO₂NH— |
| 209 | a–rr | H, H | —CH(Wᵃ)— | (4-Cl-phenyl)SO₂NH— |
| 210 | a–rr | H, H | —CH(Wᵃ)— | (4-F-phenyl)SO₂NH— |
| 211 | a–rr | H, H | —CH(Wᵃ)— | (3-Br-phenyl)SO₂NH— |
| 212 | a–rr | H, H | —CH(Wᵃ)— | (3-Cl-phenyl)SO₂NH— |
| 213 | a–rr | H, H | —CH(Wᵃ)— | (3-F-phenyl)SO₂NH— |
| 214 | a–rr | H, H | —CH(Wᵃ)— | (2-Br-phenyl)SO₂NH— |
| 215 | a–rr | H, H | —CH(Wᵃ)— | (2-Cl-phenyl)SO₂NH— |
| 216 | a–rr | H, H | —CH(Wᵃ)— | (2-F-phenyl)SO₂NH— |
| 217 | a–rr | H, H | —CH(Wᵃ)— | (4-F₃C-phenyl)SO₂NH— |
| 218 | a–rr | H, H | —CH(Wᵃ)— | (3-F₃C-phenyl)SO₂NH— |
| 219 | a–rr | H, H | —CH(Wᵃ)— | (2-F₃C-phenyl)SO₂NH— |
| 220 | a–rr | H, H | —CH(Wᵃ)— | (4-MeO-phenyl)SO₂NH— |
| 221 | a–rr | H, H | —CH(Wᵃ)— | (4-cyano-phenyl)SO₂NH— |
| 222 | a–rr | H, H | —CH(Wᵃ)— | (4-propyl-phenyl)SO₂NH— |
| 223 | a–rr | H, H | —CH(Wᵃ)— | (4-i-propyl-phenyl)SO₂NH— |
| 224 | a–rr | H, H | —CH(Wᵃ)— | (4-butyloxy-phenyl)SO₂NH— |
| 225 | a–rr | H, H | —CH(Wᵃ)— | (benzyl)SO₂NH— |
| 226 | a–rr | H, H | —CH(Wᵃ)— | (phenylethyl)SO₂NH— |
| 227 | a–rr | H, H | —CH(Wᵃ)— | (phenylpropyl)SO₂NH— |
| 228 | a–rr | H, H | —CH(Wᵃ)— | (2-pyridyl)SO₂NH— |
| 229 | a–rr | H, H | —CH(Wᵃ)— | (3-pyridyl)SO₂NH— |
| 230 | a–rr | H, H | —CH(Wᵃ)— | (4-pyridyl)SO₂NH— |
| 231 | a–rr | H, H | —CH(Wᵃ)— | (2-thienyl)SO₂NH— |
| 232 | a–rr | H, H | —CH(Wᵃ)— | (2,4,6-Me₃-phenyl)SO₂NH— |
| 233 | a–rr | H, H | —CH(Wᵃ)— | (3,5-Me₂-isoxazolyl)SO₂NH— |
| 234 | a–rr | H, H | —CH(Wᵃ)— | (ethyl)OCONH— |
| 235 | a–rr | H, H | —CH(Wᵃ)— | (n-propyl)OCONH— |
| 236 | a–rr | H, H | —CH(Wᵃ)— | (i-propyl)OCONH— |
| 237 | a–rr | H, H | —CH(Wᵃ)— | (n-butyl)OCONH— |
| 238 | a–rr | H, H | —CH(Wᵃ)— | (i-butyl)OCONH— |
| 239 | a–rr | H, H | —CH(Wᵃ)— | (t-butyl)OCONH— |

TABLE 2-continued

| | | | | |
|---|---|---|---|---|
| 240 | a–rr | H, H | —CH(Wª)— | (benzyl)OCONH— |
| 241 | a–rr | H, H | —CH(Wª)— | (4-Me-benzyl)OCONH— |
| 242 | a–rr | H, H | —CH(Wª)— | (4-MeO-benzyl)OCONH— |
| 243 | a–rr | H, H | —CH(Wª)— | (4-Br-benzyl)OCONH— |
| 244 | a–rr | H, H | —CH(Wª)— | (4-F-benzyl)OCONH— |
| 245 | a–rr | H, H | —CH(Wª)— | (4-Cl-benzyl)OCONH— |
| 246 | a–rr | H, H | —CH(Wª)— | (4-phenoxy-benzyl)OCONH— |
| 247 | a–rr | H, H | —CH(Wª)— | (2-pyridyl-methyl)OCONH— |
| 248 | a–rr | H, H | —CH(Wª)— | (3-pyridyl-methyl)OCONH— |
| 249 | a–rr | H, H | —CH(Wª)— | (4-pyridyl-methyl)OCONH— |
| 250 | a–rr | H, H | —CH(Wª)— | (cyclopropyl-ethyl)OCONH— |
| 251 | a–rr | H, H | —CH(Wª)— | (cyclopropyl-methyl)OCONH— |
| 252 | a–rr | H, H | —CH(Wª)— | (ethyl)CONH— |
| 253 | a–rr | H, H | —CH(Wª)— | (n-propyl)CONH— |
| 254 | a–rr | H, H | —CH(Wª)— | (i-propyl)CONH— |
| 255 | a–rr | H, H | —CH(Wª)— | (n-butyl)CONH— |
| 256 | a–rr | H, H | —CH(Wª)— | (i-butyl)CONH— |
| 257 | a–rr | H, H | —CH(Wª)— | (t-butyl)CONH— |
| 258 | a–rr | H, H | —CH(Wª)— | (benzyl)CONH— |
| 259 | a–rr | H, H | —CH(Wª)— | (4-Me-benzyl)CONH— |
| 260 | a–rr | H, H | —CH(Wª)— | (4-MeO-benzyl)CONH— |
| 261 | a–rr | H, H | —CH(Wª)— | (4-Br-benzyl)CONH— |
| 262 | a–rr | H, H | —CH(Wª)— | (4-F-benzyl)CONH— |
| 263 | a–rr | H, H | —CH(Wª)— | (4-Cl-benzyl)CONH— |
| 264 | a–rr | H, H | —CH(Wª)— | (4-phenoxy-benzyl)CONH— |
| 265 | a–rr | H, H | —CH(Wª)— | (2-pyridylmethyl)CONH— |
| 266 | a–rr | H, H | —CH(Wª)— | (3-pyridylmethyl)CONH— |
| 267 | a–rr | H, H | —CH(Wª)— | (4-pyridylmethyl)CONH— |
| 268 | a–rr | H, H | —CH(Wª)— | (cyclopropylethyl)CONH— |
| 269 | a–rr | H, H | —CH(Wª)— | (cyclopropyl-methyl)CONH— |
| 270 | a–rr | H, H | —CH(Wª)— | (ethyl)NHCONH— |
| 271 | a–rr | H, H | —CH(Wª)— | (n-propyl)NHCONH— |
| 272 | a–rr | H, H | —CH(Wª)— | (i-propyl)NHCONH— |
| 273 | a–rr | H, H | —CH(Wª)— | (n-butyl)NHCONH— |
| 274 | a–rr | H, H | —CH(Wª)— | (i-butyl)NHCONH— |
| 275 | a–rr | H, H | —CH(Wª)— | (t-butyl)NHCONH— |
| 276 | a–rr | H, H | —CH(Wª)— | (benzyl)NHCONH— |
| 277 | a–rr | H, H | —CH(Wª)— | (4-Me-benzyl)NHCONH— |
| 278 | a–rr | H, H | —CH(Wª)— | (4-MeO-benzyl)NHCONH— |
| 279 | a–rr | H, H | —CH(Wª)— | (4-Br-benzyl)NHCONH— |
| 280 | a–rr | H, H | —CH(Wª)— | (4-F-benzyl)NHCONH— |
| 281 | a–rr | H, H | —CH(Wª)— | (4-Cl-benzyl)NHCONH— |
| 282 | a–rr | H, H | —CH(Wª)— | (4-phenoxy-benzyl)NHCONH— |
| 283 | a–rr | H, H | —CH(Wª)— | (2-pyridyl-methyl)NHCONH— |
| 284 | a–rr | H, H | —CH(Wª)— | (3-pyridylmethyl)NHCONH— |
| 285 | a–rr | H, H | —CH(Wª)— | (4-pyridylmethyl)NHCONH— |
| 286 | a–rr | H, H | —CH(Wª)— | (cyclopropyl-ethyl)NHCONH— |
| 287 | a–rr | H, H | —CH(Wª)— | (cyclopropyl-methyl)NHCONH |
| 288 | a–rr | H, H | —OCH(Wª)— | —H |
| 289 | a–rr | H, H | —OCH(Wª)— | —CH$_3$ |
| 290 | a–rr | H, H | —OCH(Wª)— | —CH$_2$(phenyl) |
| 291 | a–rr | H, H | —OCH(Wª)— | —CH$_2$(4-MeO-phenyl) |
| 292 | a–rr | H, H | —OCH(Wª)— | —CH$_2$(4-HO-phenyl) |
| 293 | a–rr | H, H | —OCH(Wª)— | —CH$_2$CH(CH$_3$)$_2$ |
| 294 | a–rr | H, H | —OCH(Wª)— | —CH$_2$CONH(CH$_3$) |
| 295 | a–rr | H, H | —OCH(Wª)— | —CH$_2$CONH(phenyl) |
| 296 | a–rr | H, H | —OCH(Wª)— | —CH$_2$CONH(benzyl) |
| 297 | a–rr | H, H | —OCH(Wª)— | —CH$_2$NHSO$_2$(phenyl) |
| 298 | a–rr | H, H | —OCH(Wª)— | —CH$_2$NHSO$_2$(n-butyl) |
| 299 | a–rr | H, H | —OCH(Wª)— | —CH$_2$NHSO$_2$(benzyl) |
| 300 | a–rr | H, H | —OCH(Wª)— | —CH$_2$NHCO$_2$(benzyl) |
| 301 | a–rr | H, H | —OCH(Wª)— | —CH$_2$NHCO$_2$(n-butyl) |
| 302 | a–rr | H, H | —OCH(Wª)— | —CH$_2$NHCO$_2$(t-butyl) |
| 303 | a–rr | H, H | —OCH(Wª)— | —CH$_2$NHCO$_2$(i-butyl) |
| 304 | a–rr | H, H | —OCH(Wª)— | —CH$_2$O(benzyl) |
| 305 | a–rr | H, H | —OCH(Wª)— | —CH$_2$(3-indolyl) |
| 306 | a–rr | =O | —OCH(Wª)— | —H |
| 307 | a–rr | =O | —OCH(Wª)— | —CH$_3$ |
| 308 | a–rr | =O | —OCH(Wª)— | —CH$_2$(phenyl) |
| 309 | a–rr | =O | —OCH(Wª)— | —CH$_2$(4-MeO-phenyl) |
| 310 | a–rr | =O | —OCH(Wª)— | —CH$_2$(4-HO-phenyl) |
| 311 | a–rr | =O | —OCH(Wª)— | —CH$_2$CH(CH$_3$)$_2$ |
| 312 | a–rr | =O | —OCH(Wª)— | —CH$_2$CONH(CH$_3$) |
| 313 | a–rr | =O | —OCH(Wª)— | —CH$_2$CONH(phenyl) |
| 314 | a–rr | =O | —OCH(Wª)— | —CH$_2$CONH(benzyl) |
| 315 | a–rr | =O | —OCH(Wª)— | —CH$_2$NHSO$_2$(phenyl) |
| 316 | a–rr | =O | —OCH(Wª)— | —CH$_2$NHSO$_2$(n-butyl) |
| 317 | a–rr | =O | —OCH(Wª)— | —CH$_2$NHSO$_2$(benzyl) |
| 318 | a–rr | =O | —OCH(Wª)— | —CH$_2$NHCO$_2$(benzyl) |
| 319 | a–rr | =O | —OCH(Wª)— | —CH$_2$NHCO$_2$(n-butyl) |
| 320 | a–rr | =O | —OCH(Wª)— | —CH$_2$NHCO$_2$(t-butyl) |
| 321 | a–rr | =O | —OCH(Wª)— | —CH$_2$NHCO$_2$(i-butyl) |
| 322 | a–rr | =O | —OCH(Wª)— | —CH$_2$O(benzyl) |
| 323 | a–rr | =O | —OCH(Wª)— | —CH$_2$(3-indolyl) |

Utility

The compounds of this invention possess antiplatelet efficacy, as evidenced by their activity in standard platelet aggregation assays or platelet fibrinogen binding assays, as described below. A compound is considered to be active in these assays if it has an IC$_{50}$ value of less than about 50 μM. Representative compounds of the invention have been shown to have IC$_{50}$ values of less than about 50 μM. Platelet aggregation and fibrinogen binding assays which may be used to demonstrate the antiplatelet activity of the compounds of the invention are described below.

Platelet Aggregation Assay: Venous blood was obtained from the arm of a healthy human donor who was drug-free and aspirin-free for at least two weeks prior to blood collection. Blood was collected into 10 mL citrated Vacutainer tubes. The blood was centrifuged for 15 minutes at 150×g at room temperature, and platelet-rich plasma (PRP) was removed. The remaining blood was centrifuged for 15 minutes at 1500×g at room temperature, and platelet-poor plasma (PPP) was removed. Samples were assayed on a aggregometer (PAP-4 Platelet Aggregation Profiler), using PPP as the blank (100% transmittance). 200 μL of PRP was added to each micro test tube, and transmittance was set to 0%. 20 μL of various agonists (ADP, collagen, arachidonate, epinephrine, thrombin) were added to each tube, and the aggregation profiles were plotted (% transmittance versus time). The results are expressed as % inhibition of agonist-induced platelet aggregation. For the IC$_{50}$ evaluation, the test compounds were added at various concentrations prior to the activation of the platelets. Ester prodrugs were preincubated (10$^{-3}$ M F.C.) with 100 IU/mL Porcine liver esterase (Sigma Chemical Co., St. Louis, Mo., #E-3128) for 2 hours at 37° C. Aliquots are then diluted in 0.1 M Tris, pH 7.4, to the desired concentrations. Aliquots of 20 μl of the esterase pretreated prodrugs are added to 200 μl of human platelet rich plasma. Samples were placed in platelet profiler (aggregometer) for 8 minutes at 37° C., followed by the addition of 100 μM Adenosine Diphosphate, (Sigma Chemical Co., St. Louis, Mo., #A-6521), to induce platelet aggregation. Platelet aggregation was allowed to proceed for 5 minutes. Percent inhibition is calculated using percent aggregation in the presence of the test compound divided by percent aggregation of control, times 100. This value is subtracted from 100, yielding percent inhibition. Calculation of IC$_{50}$ is performed on a Texas Instruments TI59 with an IC$_{50}$ program.

Purified GPIIb/IIIa-Fibrinogen Binding ELISA

The following reagents are used in the GPIIb/IIIa-fibrinogen binding ELISA:
- purified GPIIb/IIIa (148.8 µg/mL);
- biotinylated fibrinogen (~1 mg/mL or 3000 nM);
- anti-biotin alkaline phosphatase conjugate (Sigma no. A7418);
- flat-bottom, high binding, 96-well plates (Costar Cat. no. 3590);
- phosphatase substrate (Sigma 104) (40 mg capsules);
- bovine serum albumin (BSA) (Sigma no. A3294);
- Alkaline Phosphatase buffer −0.1 M glycine-HCl, 1 mM $MgCl_2.6H_2O$, 1 mM $ZnCl_2$, pH 10.4;
- Binding buffer −20 mM Tris-HCl, 150 mM NaCl, 1 mM $CaCl_2.2H_2O$, 0.02% $NaN_3$, pH 7.0;
- Buffer A −50 mM Tris-HCl, 100 mM NaCl, 2 mM $CaCl_2.2H_2O$, 0.02% $NaN_3$, pH 7.4;
- Buffer A +3.5% BSA (Blocking buffer);
- Buffer A +0.1% BSA (Dilution buffer);
- 2N NaOH.

The following method steps are used in the GPIIb/IIIa-fibrinogen binding ELISA:

Coat plates with GPIIb/IIIa in Binding buffer (125 ng/100 µL/well) overnight at 4° C. (Leave first column uncoated for non-specific binding). Cover and freeze plates at −70° C. until used. Thaw plate 1 hour at room temperature or overnight at 4° C. Discard coating solution and wash once with 200 µL Binding buffer per well. Block plate 2 hours at room temperature on shaker with 200 µL Buffer A+3.5% BSA (Blocking buffer) per well. Discard Blocking buffer and wash once with 200 µL Buffer A+0.1% BSA (Dilution buffer) per well. Pipet 11 µL of test compound (10× the concentration to be tested in Dilution buffer) into duplicate wells. Pipet 11 µL Dilution buffer into non-specific and total binding wells. Add 100 µL Biotinylated fibrinogen (1/133 in Dilution buffer, final concentration=20 nM) to each well. Incubate plates for 3 hours at room temperature on a plate shaker. Discard assay solution and wash twice with 300 µL Binding buffer per well. Add 100 µL Anti-biotin alkaline phosphatase conjugate (1/1500 in Dilution buffer) to each well. Incubate plates for 1 hour at room temperature on plate shaker. Discard conjugate and wash twice with 300 51 Binding buffer per well. Add 100 µL Phosphatase substrate (1.5 mg/mL in Alkaline phosphatase buffer) to each well. Incubate plate at room temperature on shaker until color develops. Stop color development by adding 25 µL 2N NaOH per well. Read plate at 405 nm. Blank against non-specific binding (NSB) well. % Inhibition is calculated as follows:

% Inhibition=100−((Test Compound Abs/Total Abs)× 100).

Platelet-Fibrinogen Binding Assay: Binding of $^{125}$I-fibrinogen to platelets was performed as described by Bennett et al. (1983) Proc. Natl. Acad. Sci. USA 80: 2417–2422, with some modifications as described below. Human PRP (h-PRP) was applied to a Sepharose column for the purification of platelet fractions. Aliquots of platelets ($5×10^8$ cells) along with 1 mM calcium chloride were added to removable 96 well plates prior to the activation of the human gel purified platelets (h-GPP). Activation of the human gel purified platelets was achieved using ADP, collagen, arachidonate, epinephrine, and/or thrombin in the presence of the ligand, $^{125}$I-fibrinogen. The $^{125}$I-fibrinogen bound to the activated platelets was separated from the free form by centrifugation and then counted on a gamma counter. For an $IC_{50}$ evaluation, the test compounds were added at various concentrations prior to the activation of the platelets.

The compounds of Formula (I) of the present invention may also possess thrombolytic efficacy, that is, they are capable of lysing (breaking up) already formed platelet-rich fibrin blood clots, and thus are useful in treating a thrombus formation, as evidenced by their activity in the tests described below. Preferred compounds of the present invention for use in thrombolysis include those compounds having an $IC_{50}$ value (that is, the molar concentration of the compound capable of achieving 50% clot lysis) of less than about 1 µM, more preferably an $IC_{50}$ value of less than about 0.1 µM.

Thrombolytic Assay: Venous blood was obtained from the arm of a healthy human donor who was drug-free and aspirin free for at least two weeks prior to blood collection, and placed into 10 ml citrated Vacutainer tubes. The blood was centrifuged for 15 minutes at 1500×g at room temperature, and platelet rich plasma (PRP) was removed. To the PRP was then added $1×10^{-3}$ M of the agonist ADP, epinephrine, collagen, arachidonate, serotonin or thrombin, or a mixture thereof, and the PRP incubated for 30 minutes. The PRP was centrifuged for 12 minutes at 2500×g at room temperature. The supernatant was then poured off, and the platelets remaining in the test tube were resuspended in platelet poor plasma (PPP), which served as a plasminogen source. The suspension was then assayed on a Coulter Counter (Coulter Electronics, Inc., Hialeah, Fla.), to determine the platelet count at the zero time point. After obtaining the zero time point, test compounds were added at various concentrations. Test samples were taken at various time points and the platelets were counted using the Coulter Counter. To determine the percent of lysis, the platelet count at a time point subsequent to the addition of the test compound was subtracted from the platelet count at the zero time point, and the resulting number divided by the platelet count at the zero time point. Multiplying this result by 100 yielded the percentage of clot lysis achieved by the test compound. For the $IC_{50}$ evaluation, the test compounds were added at various concentrations, and the percentage of lysis caused by the test compounds was calculated.

The compounds of Formula (I) of the present invention are also useful for administration in combination with anti-coagulant agents such as warfarin or heparin, or anti-platelet agents such as aspirin, piroxicam or ticlopidine, or thrombin inhibitors such as boropeptides, hirudin or argatroban, or thrombolytic agents such as tissue plasminogen activator, anistreplase, urokinase, streptokinase, or reteplase or combinations thereof.

The compounds of Formula (I) of the present invention may also be useful as antagonists of other integrins such as for example, the $\alpha_v/\beta_3$ or vitronectin receptor, $\alpha_4/\beta_1$ or $\alpha_5/\beta_1$ and as such may also have utility in the treatment and diagnosis of osteoporosis, cancer metastasis, diabetic retinopathy, rheumatoid arthritis, inflammation, and autoimmune disorders. The compounds of Formula (I) of the present invention may be useful for the treatment or prevention of other diseases which involve cell adhesion processes, including, but not limited to, infammation, bone degradation, rheumatoid arthritis, asthma, allergies, adult respiratory distress syndrome, graft versus host disease, organ transplantation, septic shock, psoriasis, eczema, contact dermatitis, osteoporosis, osteoarthritis, atherosclerosis, metastasis, wound healing, diabetic retinopathy, inflammatory bowel disease and other autoimmune diseases.

The compounds of the present invention may be useful for the treatment or prevention of other diseases which involve cell adhesion processes, including, but not limited to, inflammation, bone degradation, thrombosis, rheumatoid arthritis, asthma, allergies, adult respiratory distress syndrome, graft versus host disease, organ transplantation, septic shock, psoriasis, eczema, contact dermatitis, osteoarthritis, atherosclerosis, metastasis, wound healing, diabetic retinopathy, inflammatory bowel disease and other angiogenic disorders.

The integrin antagonist activity of the compounds of the present invention is demonstrated using assays which measure the binding of a specific integrin to a native ligand, for example, using the ELISA assay described below for the binding of vitronectin to the $\alpha_v/\beta_3$ receptor. The compounds provided by this invention are also useful as standards and reagents in determining the ability of a potential pharmaceutical to inhibit integrin-ligand binding. These would be provided in commercial kits comprising a compound of this invention.

Integrin Cell-Based Adhesion Assays

In the adhesion assays, a 96 well plate was coated with the ligand (i.e., fibrinogen) and incubated overnight at 4° C. The following day, the cells were harvested, washed and loaded with a fluorescent dye. Compounds and cells were added together and then were immediately added to the coated plate. After incubation, loose cells are removed from the plate, and the plate (with adherent cells) is counted on a fluorometer. The ability of test compounds to inhibit cell adhesion by 50% is given by the $IC_{50}$ value and represents a measure of potency of inhibition of integrin mediated binding. Compounds were tested for their ability to block cell adhesion using assays specific for $\alpha_v/\beta_3$, $\alpha_v/\beta_5$ and $\alpha_5/\beta_1$ integrin interactions.

Dosage and Formulation

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an anti-aggregation agent. Finally, the compounds of the invention may also be administered intranasally.

The compounds of this invention can be administered by any means that produces contact of the active agent with the agent's site of action, glycoprotein IIb/IIIa (GPIIb/IIIa), in the body of a mammal. They can be administered by any conventional means available for use in conjunction with pharmaceuticals, either as individual therapeutic agents or in a combination of therapeutic agents, such as a second antiplatelet agent such as aspirin or ticlopidine which are agonist-specific. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

The active ingredient can be administered intranasally to a mammal at a dosage range of about 0.01 to 0.5 mg/kg while the preferred dosage range is about 0.01–0.1 mg/kg.

Compositions of the active ingredients can be administered intranasally by preparing a suitable formulation of the active ingredient by procedures well known to those skilled in the art. Preferably the formulations are prepared with suitable nontoxic pharmaceutically acceptable ingredients. These ingredients are known to those skilled in the preparation of nasal dosage forms and some of these can be found in REMINGTON'S PHARMACEUTICAL SCIENCES. 17th edition, 1985 a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, jelling agents, or buffering and other stabilizing and solubilizing agents may also be present. Preferably, the nasal dosage form should be isotonic with nasal secretions.

The nasal formulation can be administered as drops, sprays, aerosols or by any other intranasal dosage form. Optionally, the delivery system can be a unit dose delivery system. The volume of solution or suspension delivered per dose can be anywhere from 5 to 400 $\mu$L, and preferably between 50 and 150 $\mu$L. Delivery systems for these various dosage forms can be dropper bottles, plastic squeeze units, atomizers, nebulizers or pharmaceutical aerosols in either unit dose or multiple dose packages.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered iontophoretic delivery systems, also refered to as electrotransport systems, by one skilled in the art of iontophoretic delivery. Controlled, continuous delivery of drugs at constant rates is a highly useful method of delivering medications. This kind of delivery ensures relatively constant plasma concentrations and, more importantly, proper control of pharmacologic and toxic drug effect. Transdermal delivery can be an especially useful means of controlled, continuous delivery of drugs that exhibit no/low oral bioavailability while avoiding the inconvenience and discomfort of administration by injection.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules are prepared by filling standard two-piece hard gelatin capsules each with 1–20 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 1–20 milligrams of the active ingredient. The capsules are washed and dried.

Tablets

A large number of tablets are prepared by conventional procedures so that the dosage unit was 1–20 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 1–20 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent selected from: an anti-coagulant agent such as warfarin, heparin, or low molecular weight heparin; an anti-platelet agent such as aspirin, piroxicam or ticlopidine; a thrombin inhibitor such as a boropeptide thrombin inhibitor, hirudin, or Factor Xa inhibitor; or a thrombolytic agent such as plasminogen activators, such as tissue plasminogen activator, anistreplase, urokinase, streptokinase, or reteplase. The compound of Formula (I) and such second therapeutic agent can be administered separately or as a physical combination in a single dosage unit, in any dosage form and by various routes of administration, as described above.

The compound of Formula (I) may be formulated together with the second therapeutic agent in a single dosage unit (that is, combined together in one capsule, tablet, powder, or liquid, etc.). When the compound of Formula (I) and the second therapeutic agent are not formulated together in a single dosage unit, the compound of Formula (I) and the second therapeutic agent (anti-coagulant agent, anti-platelet agent, thrombin inhibitor, and/or thrombolytic agent) may be administered essentially at the same time, or in any order; for example the compound of Formula (I) may be administered first, followed by administration of the second agent (anti-coagulant agent, anti-platelet agent, thrombin inhibitor, and/or thrombolytic agent). When not administered at the same time, preferably the administration of the compound of Formula (I) and the second therapeutic agent occurs less than about one hour apart.

A preferable route of administration of the compound of Formula (I) is oral. Although it is preferable that the compound of Formula (I) and the second therapeutic agent (anti-coagulant agent, anti-platelet agent, thrombin inhibitor, and/or thrombolytic agent) are both administered by the same route (that is, for example, both orally), if desired, they may each be administered by different routes and in different dosage forms (that is, for example, one component of the combination product may be administered orally, and another component may be administered intravenously).

The dosage of the compound of Formula (I) when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Although the proper dosage of the compound of Formula (I) when administered in combination with the second therapeutic agent will be readily ascertainable by a medical practitioner skilled in the art, once armed with the present disclosure, by way of general guidance, where the compounds of this invention are combined with anti-coagulant agents, for example, a daily dosage may be about 0.1 to 100 milligrams of the compound of Formula (I) and about 1 to 7.5 milligrams of the anticoagulant, per kilogram of patient body weight. For a tablet dosage form, the novel compounds of this invention generally may be present in an amount of about 1 to 10 milligrams per dosage unit, and the anti-coagulant in an amount of about 1 to 5 milligrams per dosage unit.

Where the compounds of Formula (I) are administered in combination with a second anti-platelet agent, by way of general guidance, typically a daily dosage may be about 0.01 to 25 milligrams of the compound of Formula (I) and about 50 to 150 milligrams of the additional anti-platelet agent, preferably about 0.1 to 1 milligrams of the compound of Formula (I) and about 1 to 3 milligrams of antiplatelet agents, per kilogram of patient body weight.

Further, by way of general guidance, where the compounds of Formula (I) are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula (I) and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the inhibition of platelet aggregation, the treatment of blood clots, and/or the treatment of thromboembolic disorders, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

What is claimed is:
1. A compound of Formula (I):

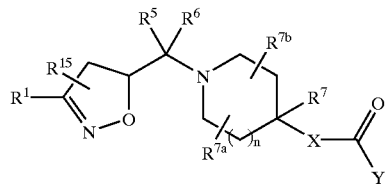

or a pharmaceutically acceptable salt form thereof wherein:
R$^1$ is selected from
$R^{2a}(R^3)N-V-$,
$R^{2a}(R^3)N(CH_2)_q-$,
$R^2(R^{2b})N(R^3N=)C-V-$,
$R^2(R^{2b})N(R^3N=)C(CH_2)_q-$,
$R^2(R^{2b})N(R^3N=)CNH-V-$,
$R^2(R^{11}O)N(R^3N=)C-V-$,
$R^2(R^{2b})N(R^{11}ON=)C-V-$,

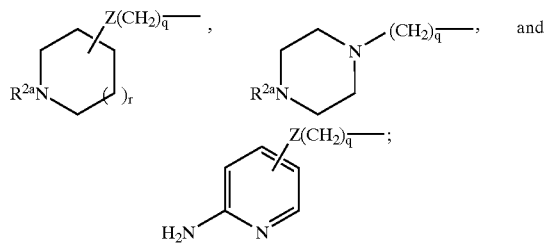

V is selected from:
—($C_1$–$C_4$ alkyl)-,
—($C_2$–$C_4$ alkenyl)-,
—($C_2$–$C_4$ alkynyl)-,
—(phenyl)-, said phenyl substituted with 0–2 groups independently selected from R$^9$,
—(pyridyl)-, said pyridyl substituted with 0–2 groups independently selected from R$^9$, and
—(pyridazinyl)-, said pyridazinyl substituted with 0–2 groups independently selected from R$^9$;
Z is selected from: a bond, O, S, S(=O), and S(=O)$_2$;
R$^{2a}$ is R$^2$ or $R^2(R^{2b})N(R^3N=)C-$;
R$^2$, R$^{2b}$, and R$^3$ are independently selected from:
H,
$C_1$–$C_{10}$ alkyl,
$C_3$–$C_6$ alkenyl,
$C_3$–$C_6$ alkynyl,
$C_3$–$C_{10}$ cycloalkyl,
$C_3$–$C_{10}$ cycloalkyl($C_1$–$C_4$ alkyl)-,
$C_2$–$C_7$ alkylcarbonyl,
$C_1$–$C_4$ haloalkyl,
aryl,
arylcarbonyl,
aryl($C_1$–$C_4$ alkyl)-,
benzhydryl,
benzhydryl($C_1$–$C_4$ alkyl)-,
heteroaryl,
heteroaryl($C_1$–$C_5$ alkyl)-,
$C_1$–$C_6$ alkoxycarbonyl,
$C_3$–$C_{11}$ cycloalkoxycarbonyl,
$C_7$–$C_{11}$ bicycloalkoxycarbonyl,
aryloxycarbonyl,
aryl($C_1$–$C_{10}$ alkoxy)carbonyl,
($C_1$–$C_6$ alkyl)carbonyloxy($C_1$–$C_4$ alkoxy)carbonyl,
arylcarbonyloxy($C_1$–$C_4$ alkoxy)carbonyl, and
($C_3$–$C_{11}$ cycloalkyl)carbonyloxy($C_1$–$C_4$ alkoxy)carbonyl;
wherein at least one of R$^2$, R$^{2b}$, and R$^3$ is H,
$C_1$–$C_6$ alkoxycarbonyl,
$C_3$–$C_{11}$ cycloalkoxycarbonyl,
$C_7$–$C_{11}$ bicycloalkoxycarbonyl,
aryloxycarbonyl,
aryl($C_1$–$C_{10}$ alkoxy)carbonyl,
($C_1$–$C_6$ alkyl)carbonyloxy($C_1$–$C_4$ alkoxy)carbonyl,
arylcarbonyloxy($C_1$–$C_4$ alkoxy)carbonyl, or
($C_3$–$C_{11}$ cycloalkyl)carbonyloxy($C_1$–$C_4$ alkoxy)carbonyl;
wherein said aryl groups of R$^2$, R$^{2b}$, and R$^3$ may be substituted with 0–3 groups selected from hydroxy, halogen, $C_1$–$C_6$ alkoxy, $C_1$–$C_6$ alkyl, CF$_3$, —CN, —SO$_2$($C_1$–$C_4$ alkyl), —S($C_1$–$C_4$ alkyl), —NR$^{21}$R$^{22}$, $C_1$–$C_4$ haloalkyl, methylenedioxydiyl, and ethylenedioxydiyl; and
said heteroaryl groups of R$^2$, R$^{2b}$, and R$^3$ may be substituted with 0–2 groups selected from hydroxy, halogen, $C_1$–$C_6$ alkoxy, $C_1$–$C_6$ alkyl, CF$_3$, SO$_2$CH$_3$, and —NR$^{21}$R$^{22}$;
alternatively, R$^2$ and R$^{2b}$ can be taken together with the nitrogen atom to which they are attached to form a 5–10 membered heterocyclic ring optionally containing one additional heteroatom selected from: N, O, or S; said heterocyclic ring being monocyclic or bicyclic; said heterocyclic ring being substituted with 0–2 R$^4$;
R$^4$, when a substituent on carbon, is independently selected from:
H, $C_1$–$C_4$ alkyl, aryl, and aryl($C_1$–$C_6$ alkyl)-, wherein said aryl groups may be optionally substituted with 0–3 groups selected from hydroxy, halogen, $C_1$–$C_6$ alkoxy, $C_1$–$C_6$ alkyl, CF$_3$, SCH$_3$, S(O)CH$_3$, SO$_2$CH$_3$, —NR$^{21}$R$^{22}$, $C_1$–$C_4$ haloalkyl, methylenedioxydiyl, and ethylenedioxydiyl;
alternatively, when two R$^4$ groups are attached to adjacent carbon atoms, they may be taken together with the atoms to which they are attached to form a fused 5–7 membered saturated, unsaturated or aromatic carbocyclic ring;
alternatively, when R$^4$ is attached to a saturated carbon atom, it may also be =O or =S;
R$^4$, when a substituent on nitrogen, is independently selected from:
H,
$C_1$–$C_6$ alkyl,
$C_3$–$C_6$ alkenyl,
$C_1$–$C_{10}$ alkoxycarbonyl,
$C_1$–$C_{10}$ alkylcarbonyl,
$C_1$–$C_{10}$ alkylsulfonyl,
$C_3$–$C_{10}$ cycloalkyl,
$C_3$–$C_{10}$ cycloalkyl($C_1$–$C_4$ alkyl)-,
$C_3$–$C_{11}$ cycloalkoxycarbonyl,
$C_7$–$C_{11}$ bicycloalkoxycarbonyl,
aryl,
aryl($C_1$–$C_{10}$ alkyl)-,
benzhydryl,
benzhydryl($C_1$–$C_4$ alkyl)-,
arylcarbonyl,
aryloxycarbonyl,
arylsulfonyl,
aryl($C_1$–$C_{10}$ alkyl)sulfonyl,
aryl($C_2$–$C_{10}$ alkenyl)sulfonyl,
aryl($C_1$–$C_{10}$ alkoxy)carbonyl, heteroaryl,
heteroarylsulfonyl,
heteroarylcarbonyl,
heteroaryl($C_1$–$C_{10}$ alkyl)-, and
heteroaryl($C_1$–$C_{10}$ alkyl)carbonyl,
wherein said aryl or heteroaryl groups may be additionally substitututed with 0–2 groups selected from hydroxy, halogen, $C_1$–$C_6$ alkoxy, $C_1$–$C_6$ alkyl, $CF_3$, $SCH_3$, $SOCH_3$, $SO_2CH_3$, and —$NR^{21}R^{22}$;

$R^4$, when a substituent on sulfur, may be =O;

X is —$CH_2CH(W^a)$—, —$CH(W^a)CH_2$—, —$CH(W^a)$—, —$OCH(W^b)$—, —$SCH(W^b)$—, —$NHCH(W^b)$—, —$OCH(W^b)CH_2$—, —$SCH(W^b)CH_2$—, —$NHCH(W^b)CH_2$—, —$OCH_2CH(W^a)$—, —$SCH_2CH(W^a)$—, or —$NHCH_2CH(W^a)$—;

Y is selected from hydroxy,
$C_1$–$C_{10}$ alkyloxy,
$C_3$–$C_{11}$ cycloalkyloxy,
$C_6$–$C_{10}$ aryloxy,
$C_7$–$C_{11}$ arylalkyloxy,
$C_2$–$C_{10}$ alkylcarbonyloxyalkyloxy,
$C_2$–$C_{10}$ alkoxycarbonyloxyalkyloxy,
$C_2$–$C_{10}$ alkoxycarbonylalkyloxy,
$C_4$–$C_{10}$ cycloalkylcarbonyloxyalkyloxy,
$C_4$–$C_{10}$ cycloalkoxycarbonyloxyalkyloxy,
$C_4$–$C_{10}$ cycloalkoxycarbonylalkyloxy,
$C_7$–$C_{11}$ aryloxycarbonylalkyloxy,
$C_7$–$C_{12}$ aryloxycarbonyloxyalkyloxy,
$C_7$–$C_{12}$ arylcarbonyloxyalkyloxy,
$C_4$–$C_{10}$ alkoxyalkylcarbonyloxyalkyloxy,
(5-($C_1$–$C_4$ alkyl)-1,3-dioxa-cyclopenten-2-one-yl)methyloxy,
(5-aryl-1,3-dioxa-cyclopenten-2-one-yl)methyloxy, and
$(R^{28})(R^{29})N$-($C_1$–$C_{10}$ alkoxy)-;

$W^a$ is selected from:
H,
hydroxy,
—$NR^{16}R^{20}$,
—$NR^{25}R^{26}$,
$C_1$–$C_{10}$ alkoxy,
$C_1$–$C_{10}$ alkyl substituted with 0–3 $R^8$, and
aryl substituted with 0–3 $R^8$;

$W^b$ is selected from:
H,
$CH_2OH$,
$CH_2OR^{12}$,
$CH_2CO_2R^{12}$,
$CH_2C(=O)NHR^{18}$,
$CH_2NR^{16}R^{20}$,
$CH_2NR^{25}R^{26}$,
$C_1$–$C_8$ alkyl substituted with 0–2 $R^8$,
$C_3$–$C_6$ alkenyl,
$C_3$–$C_{10}$ cycloalkyl,
$C_4$–$C_{11}$ cycloalkylmethyl,
heteroaryl,
heteroaryl($C_1$–$C_6$ alkyl),
aryl substituted with 0–3 $R^8$, and
aryl($C_1$–$C_6$ alkyl), said aryl substituted with 0–3 $R^8$;

$R^5$ is selected from:
H,
fluoro,
$C_1$–$C_8$ alkyl substituted with 0–2 $R^8$,
$C_3$–$C_6$ alkenyl,
$C_4$–$C_{11}$ cycloalkylmethyl, and
aryl($C_1$–$C_6$ alkyl)-;

$R^6$ is H, methyl, or fluoro;

$R^7$ is selected from:
H,
hydroxy,
$C_1$–$C_4$ alkoxy,
—$C(=O)NHR^{18}$, and
—$NR^{16}R^{20}$;

$R^{7a}$ and $R^{7b}$ are independently selected from H, hydroxy, cyano, fluoro, methyl, and ethyl;

alternatively, when $R^7$ and $R^{7a}$ occur on adjacent carbons $R^7$ and $R^{7a}$ may be taken together to form a carbon-carbon double bond;

alternatively, when $R^{7a}$ and $R^{7b}$ occur on adjacent carbons $R^{7a}$ and $R^{7b}$ may be taken together to form a six carbon aromatic ring;

$R^8$ is selected from:
H,
hydroxy,
cyano,
—$CO_2R^{12}$,
—$C(=O)R^{13}$,
—$OC(=O)R^{13}$,
—$OC(=O)R^{14}$,
—$OR^{12}$,
—$OCH_2CO_2R^{12}$,
—$CO_2CH_2CO_2R^{12}$,
—$OC(=O)NR^{23}R^{24}$,
—$C(=O)NR^{23}R^{24}$,
—$NR^{25}R^{26}$,
—$NR^{27}C(=O)R^{13}$,
—$NR^{27}C(=O)$ $OR^{14}$,
—$NR^{27}SO_2R^{14}$,
—$SR^{14}$,
—$SOR^{14}$,
—$SO_2R^{14}$,
—$SO_2NR^{23}R^{24}$,
$C_1$–$C_{10}$ alkoxy,
$C_1$–$C_{10}$ alkylcarbonyl,
$C_2$–$C_6$ alkenyl,
$C_3$–$C_{10}$ cycloalkyl,
$C_4$–$C_{11}$ cycloalkylmethyl,
aryl, wherein said aryl is substituted with 0–3 groups selected from halogen, $C_1$–$C_6$ alkoxy, $C_1$–$C_6$ alkyl, $CF_3$, $CO_2R^{12}$, $SO_2Me$, $SOMe$, $SMe$ and —$NMe_2$,
aryl($C_1$–$C_4$ alkyl)-, wherein said aryl is substituted with 0–3 groups selected from halogen, $C_1$–$C_6$ alkoxy, $C_1$–$C_6$ alkyl, $CF_3$, $CO_2R^{12}$, $SO_2Me$, $SOMe$, $SMe$, and —$NMe_2$, and
a 5–10 membered heterocyclic ring containing 1–3 N, O, or S heteroatoms, wherein said heterocyclic ring may be saturated, partially saturated, or fully unsaturated, said heterocyclic ring being substituted with 0–2 groups selected from halogen, $C_1$–$C_6$ alkoxy, $C_1$–$C_6$ alkyl, $CF_3$, $CO_2R^{12}$, $SO_2Me$, $SOMe$, $SMe$ and —$NMe_2$;

$R^9$ is selected from H, halogen, $CF_3$, CN, $C_1$–$C_4$ alkyl, and $C_1$–$C_4$ alkoxy;

$R^{10}$ is selected from:
H,
hydroxy,
CN,
carboxy,
—$NR^{25}R^{26}$;
$C_1$–$C_6$ alkyl,
$C_2$–$C_6$ alkenyl,
$C_2$–$C_6$ alkynyl,
$C_3$–$C_7$ cycloalkyl, $C_7-C_{14}$ bicycloalkyl,
$C_1-C_6$ alkoxy,
$C_1-C_6$ alkylthio,
$C_1-C_6$ alkylsulfinyl,
$C_1-C_6$ alkylsulfonyl,
$C_1-C_6$ alkylcarbonyl,
$C_1-C_6$ alkoxycarbonyl,
aryl,
piperidinyl,
morpholinyl, and
pyridinyl;

$R^{11}$ is selected from:
H,
$C_1-C_8$ alkyl,
$C_3-C_6$ alkenyl,
$C_3-C_{11}$ cycloalkyl,
$C_4-C_{11}$ cycloalkylmethyl,
aryl,
aryl($C_1-C_4$ alkyl)-, and
$C_1-C_{10}$ alkyl substituted with 1–2 $R^{10}$;

$R^{12}$ is selected from:
H,
$C_1-C_8$ alkyl,
$C_3-C_6$ alkenyl,
$C_3-C_{11}$ cycloalkyl,
$C_4-C_{11}$ cycloalkylmethyl,
aryl,
aryl($C_1-C_4$ alkyl)-, and
$C_1-C_{10}$ alkyl substituted with 1–2 $R^{10}$;

$R^{13}$ is selected from:
hydrogen,
$C_1-C_8$ alkyl,
$C_3-C_6$ alkenyl,
$C_3-C_{11}$ cycloalkyl,
$C_4-C_{11}$ cycloalkylmethyl,
aryl,
aryl($C_1-C_4$ alkyl)-,
heteroaryl,
heteroaryl($C_1-C_4$ alkyl)-, and
$C_1-C_{10}$ alkyl substituted with 1–2 $R^{10}$;

$R^{14}$ is selected from:
$C_1-C_8$ alkyl,
$C_2-C_6$ alkenyl,
$C_3-C_{11}$ cycloalkyl,
$C_4-C_{11}$ cycloalkylmethyl,
aryl,
aryl($C_1-C_4$ alkyl)-, and
$C_1-C_{10}$ alkyl substituted with 1–2 $R^{10}$;

$R^{15}$ is selected from:
H,
OH,
—$OR^{12}$,
—$CO_2R^{12}$,
—$C(=O)NR^{23}R^{24}$,
—$OC(=O) NR^{23}R^{24}$,
$C_1-C_{10}$ alkoxycarbonyl substituted with 0–2 $R^8$;
$C_1-C_{10}$ alkyl substituted with 0–3 $R^8$;
$C_2-C_{10}$ alkenyl substituted with 0–3 $R^8$; and
$C_1-C_{10}$ alkoxy substituted with 0–3 $R^8$;

$R^{16}$ is selected from:
—$C(=O)OR^{17}$,
—$C(=O)R^{18}$,
—$C(=O)NR^{17}R^{18}$,
—$C(=O)NHSO_2R^{17}$,
—$C(=O)NHC(=O)R^{17}$,
—$C(=O)NHC(=O)OR^{17}$,
—$C(=O)NHSO_2NHR^{17}$,
—$SO_2R^{17}$,
—$SO_2NR^{17}R^{18}$, and
—$SO_2NHC(=O) OR^{17}$;

$R^{17}$ is selected from:
$C_1-C_8$ alkyl substituted with 0–2 $R^{19}$,
$C_3-C_8$ alkenyl substituted with 0–2 $R^{19}$,
$C_3-C_8$ alkynyl substituted with 0–2 $R^{19}$,
$C_3-C_8$ cycloalkyl substituted with 0–2 $R^{19}$,
aryl substituted with 0–4 $R^{19}$,
aryl($C_1-C_6$ alkyl)-substituted with 0–4 $R^{19}$,
a 5–10 membered heterocyclic ring system having 1–3 heteroatoms selected independently from O, S, and N, said heterocyclic ring being substituted with 0–4 $R^{19}$, and
$C_1-C_6$ alkyl substituted with a 5–10 membered heterocyclic ring system having 1–3 heteroatoms selected independently from O, S, and N, said heterocyclic ring being substituted with 0–4 $R^{19}$;

$R^{18}$ is selected from H and $R^{17}$;

$R^{19}$ is selected from:
H,
halogen,
$CF_3$,
CN,
$NO_2$,
$NR^{25}R^{26}$,
$C_1-C_8$ alkyl,
$C_2-C_6$ alkenyl,
$C_2-C_6$ alkynyl,
$C_3-C_{11}$ cycloalkyl,
$C_3-C_{11}$ cycloalkyl($C_1-C_4$ alkyl)-,
aryl,
aryl($C_1-C_6$ alkyl)-,
$C_1-C_6$ alkoxy, and
$C_1-C_4$ alkoxycarbonyl;

$R^{20}$ is selected from:
H,
$C_1-C_{10}$ alkyl,
$C_2-C_6$ alkenyl,
$C_3-C_{11}$ cycloalkyl,
$C_3-C_{11}$ cycloalkyl($C_1-C_4$ alkyl)-,
aryl, and
aryl($C_1-C_{10}$ alkyl)-;

$R^{21}$ and $R^{22}$ are each independently H, methyl, ethyl, propyl, or butyl;

$R^{23}$ is selected from:
hydrogen,
$C_1-C_8$ alkyl,
$C_3-C_6$ alkenyl,
$C_3-C_{11}$ cycloalkyl,
$C_4-C_{11}$ cycloalkylmethyl,
hydroxy,
$C_1-C_6$ alkoxy,
benzyloxy,
aryl,
aryl($C_1-C_4$ alkyl)-,
heteroaryl,
heteroaryl($C_1-C_4$ alkyl)-,
adamantylmethyl, and
$C_1-C_{10}$ alkyl substituted with 1–2 $R^{10}$;

$R^{24}$ is selected from:
$C_1-C_8$ alkyl,
$C_2-C_6$ alkenyl,
$C_3-C_{11}$ cycloalkyl,
$C_4-C_{11}$ cycloalkylmethyl, aryl,
aryl($C_1$–$C_4$ alkyl)-, and
$C_1$–$C_{10}$ alkyl substituted with 1–2 $R^{10}$;

$R^{25}$ and $R^{26}$ are, independently, selected from:
H,
$C_1$–$C_{10}$ alkyl,
$C_1$–$C_{10}$ alkoxycarbonyl,
$C_1$–$C_{10}$ alkylcarbonyl,
$C_1$–$C_{10}$ alkylsulfonyl,
aryl,
aryl($C_1$–$C_4$ alkyl)-,
arylcarbonyl,
aryloxycarbonyl,
arylsulfonyl,
aryl($C_1$–$C_{10}$ alkoxy)carbonyl,
aryl($C_1$–$C_{10}$ alkyl)sulfonyl,
aryl($C_2$–$C_{10}$ alkenyl)sulfonyl,
$C_2$–$C_6$ alkenyl,
$C_3$–$C_{10}$ cycloalkyl,
$C_3$–$C_{10}$ cycloalkyl($C_1$–$C_4$ alkyl)-,
$C_3$–$C_{10}$ cycloalkoxycarbonyl,
$C_7$–$C_{11}$ bicycloalkoxycarbonyl,
heteroaryl,
heteroarylcarbonyl,
heteroarylsulfonyl, and
heteroaryl($C_1$–$C_4$ alkyl)carbonyl,
  wherein said aryl groups are optionally substituted with 1–3 substituents selected from the group consisting of: $C_1$–$C_4$ alkyl, $C_1$–$C_4$ alkoxy, halo, $CF_3$, and $NO_2$;

$R^{27}$ is selected from H, methyl, ethyl, propyl, butyl, benzyl, phenethyl, cyclopropyl, and cyclopropylmethyl;

$R^{28}$ and $R^{29}$ are independently selected from:
H, $C_1$–$C_8$ alkyl, $C_3$–$C_6$ alkenyl, $C_3$–$C_{10}$ cycloalkyl ($C_0$–$C_4$ alkyl), aryl($C_0$–$C_4$ alkyl), and heteroaryl ($C_0$–$C_4$ alkyl), wherein said aryl or heteroaryl groups are substituted with 0–2 substituents independently selected from $C_1$–$C_4$ alkyl, $C_1$–$C_4$ alkoxy, F, Cl, Br, $CF_3$, and $NO_2$;

n is 0 or 1;
q is 1, 2, 3, or 4;
r is 0, 1, or 2; and
s is 1, 2, 3, or 4.

2. A compound according to claim 1 wherein:
$R^1$ is selected from
$R^{2a}(R^3)N$—V—, $R^2(R^{2b})N(R^3N=)C$—V—, $R^2(R^{2b})N(R^3N=)CNH$—V—,
$R^2(R^{11}O)N(R^3N=)C$—V—, $R^2(R^{2b})N(R^{11}ON=)C$—V—,

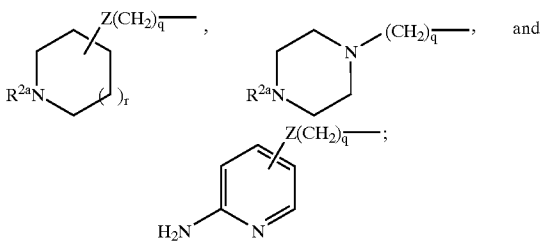

V is selected from:
—($C_1$–$C_4$ alkyl)-,
—(phenyl)-, said phenyl substituted with 0–2 groups independently selected from $R^9$,
—(pyridyl)-, said pyridyl substituted with 0–2 groups independently selected from $R^9$, and
—(pyridazinyl)-, said pyridazinyl substituted with 0–2 groups independently selected from $R^9$;

Z is selected from: a bond, O, and $S(=O)_2$;

X is —$CH_2CH(W^a)$—, —$CH(W^a)CH_2$—, —$CH(W^a)$—, —$OCH(W^b)$—, —$SCH(W^b)$—, —$NHCH(W^b)$—, or —$OCH(W^b)CH_2$—;

$W^a$ is selected from:
H, hydroxy, —$NHR^{16}$, —$NR^{25}R^{26}$, $C_1$–$C_{10}$ alkoxy, $C_1$–$C_{10}$ alkyl substituted with 0–3 $R^8$, and aryl substituted with 0–3 $R^8$;

$R^6$ is H;

$R^7$ is selected from:
H, hydroxy, methoxy, ethoxy, propoxy, butoxy, —C(=O)$NHR^{18}$, and —$NR^{16}R^{20}$;

$R^{12}$ is selected from H, aryl($C_1$–$C_4$ alkyl)-, and $C_1$–$C_{10}$ alkyl substituted with 1–2 $R^{10}$;

$R^{15}$ is selected from H, OH, —$OR^{12}$, —$CO_2R^{12}$, —C(=O)$NR^{23}R^{24}$, and —OC(=O)$NR^{23}R^{24}$;

$R^{16}$ is selected from —C(=O)$OR^{17}$, —C(=O)$R^{18}$, —$SO_2R^{17}$, and —$SO_2NR^{17}R^{18}$;

$R^{17}$ is selected from:
$C_1$–$C_8$ alkyl substituted with 0–2 $R^{19}$,
$C_3$–$C_8$ alkenyl substituted with 0–2 $R^{19}$,
$C_3$–$C_8$ alkynyl substituted with 0–2 $R^{19}$,
$C_3$–$C_8$ cycloalkyl substituted with 0–2 $R^{19}$,
aryl substituted with 0–4 $R^{19}$,
aryl($C_1$–$C_6$ alkyl)- substituted with 0–4 $R^{19}$,
a 5–10 membered heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzyimdazolyl, piperidinyl, tetrahydrofuranyl, pyranyl, pyrimidinyl, 3H-indolyl, pyrrolidinyl, morpholinyl, and piperazinyl, said heterocyclic ring being substituted with 0–4 $R^{19}$, said heterocyclic ring being substituted with 0–4 $R^{19}$, and
$C_1$–$C_6$ alkyl substituted with a 5–10 membered heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzyimdazolyl, piperidinyl, tetrahydrofuranyl, pyranyl, pyrimidinyl, 3H-indolyl, pyrrolidinyl, morpholinyl, and piperazinyl, said heterocyclic ring being substituted with 0–4 $R^{19}$;

$R^{18}$ is selected from H and $C_1$–$C_5$ alkyl;

n is 0 or 1;
q is 1, 2, 3, or 4;
r is 0, 1, or 2; and
s is 1, 2, 3, or 4.

3. A compound according to claim 2 of Formula (Ia):

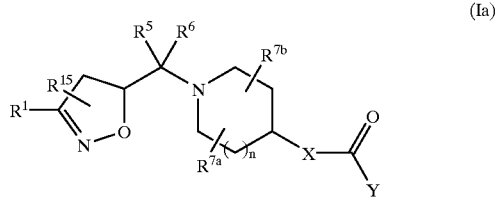

(Ia)

wherein:
$R^1$ is selected from $R^2(R^{2b})N(R^3N=)C$—V—, $R^2(R^{2b})N(R^3N=)CNH$—V—,

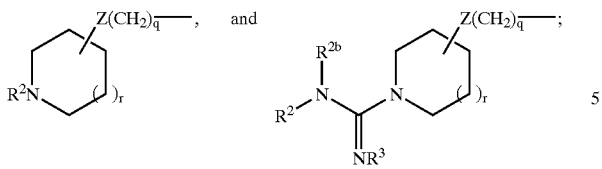

V is selected from:
—(C$_1$–C$_4$ alkyl)-,
—(pyridyl)-, and
—(phenyl)-, said phenyl substituted with 0–2 groups independently selected from F, Br, methyl, and methoxy;

Z is a bond or O;

R$^2$, R$^{2b}$, and R$^3$ are independently selected from:
H, C$_1$–C$_8$ alkyl, C$_3$–C$_6$ alkenyl, C$_3$–C$_6$ alkynyl, C$_3$–C$_8$ cycloalkyl, C$_3$–C$_8$ cycloalkyl(C$_1$–C$_4$ alkyl)-, C$_2$–C$_7$ alkylcarbonyl, C$_1$–C$_4$ haloalkyl, aryl, arylcarbonyl, aryl(C$_1$–C$_4$ alkyl)-, benzhydryl, benzhydryl(C$_1$–C$_4$ alkyl)-, heteroaryl, heteroaryl(C$_1$–C$_4$ alkyl)-,
C$_1$–C$_6$ alkoxycarbonyl,
C$_3$–C$_8$ cycloalkoxycarbonyl,
C$_7$–C$_{11}$ bicycloalkoxycarbonyl,
aryloxycarbonyl,
aryl(C$_1$–C$_8$ alkoxy)carbonyl,
(C$_1$–C$_6$ alkyl)carbonyloxy(C$_1$–C$_4$ alkoxy)carbonyl,
arylcarbonyloxy(C$_1$–C$_4$ alkoxy)carbonyl, and
(C$_3$–C$_8$ cycloalkyl)carbonyloxy(C$_1$–C$_4$ alkoxy)carbonyl;

wherein at least one of R$^2$, R$^{2b}$, and R$^3$ is H,
C$_1$–C$_6$ alkoxycarbonyl,
C$_3$–C$_8$ cycloalkoxycarbonyl,
C$_7$–C$_{11}$ bicycloalkoxycarbonyl,
aryloxycarbonyl,
aryl(C$_1$–C$_8$ alkoxy)carbonyl,
(C$_1$–C$_6$ alkyl)carbonyloxy(C$_1$–C$_4$ alkoxy)carbonyl,
arylcarbonyloxy(C$_1$–C$_4$ alkoxy)carbonyl, or
(C$_3$–C$_8$ cycloalkyl)carbonyloxy(C$_1$–C$_4$ alkoxy)carbonyl;

wherein said aryl groups of R$^2$, R$^{2b}$, and R$^3$ may be substituted with 0–3 groups selected from hydroxy, halogen, C$_1$–C$_6$ alkoxy, C$_1$–C$_6$ alkyl, CF$_3$, —CN, —SO$_2$(C$_1$–C$_4$ alkyl), —S(C$_1$–C$_4$ alkyl), —NR$^{21}$R$^{22}$, C$_1$–C$_4$ haloalkyl, methylenedioxydiyl, and ethylenedioxydiyl; and said heteroaryl groups of R$^2$, R$^{2b}$, and R$^3$ may be substituted with 0–2 groups selected from hydroxy, halogen, C$_1$–C$_6$ alkoxy, C$_1$–C$_6$ alkyl, CF$_3$, SO$_2$CH$_3$, and —NR$^{21}$R$^{22}$;

alternatively, R$^2$ and R$^{2b}$ can be taken together with the nitrogen atom to which they are attached to form a 5–10 membered heterocyclic ring system selected from morpholine, piperidine, piperazine, pyrrolidine, tetrahydroisoquinoline, thiazolidine, thiomorpholine, 1,4-benzoxazine, 8-oxo-3-azabicyclo[3.2.1]octane, 1,4-dioxa-8-azaspiro[4.5]decane, and azepine, said heterocyclic ring being substituted with 0–2 R$^4$;

X is —CH$_2$CH(W$^a$)—, —CH(W$^a$)CH$_2$—, —CH(W$^a$)—, or —OCH(W$^b$)-;

Y is selected from hydroxy,
C$_1$–C$_6$ alkoxy;
methylcarbonyloxymethoxy-;
ethylcarbonyloxymethoxy-;
t-butylcarbonyloxymethoxy-;
cyclohexylcarbonyloxymethoxy-;
1-(methylcarbonyloxy)ethoxy-;
1-(ethylcarbonyloxy)ethoxy-;
1-(t-butylcarbonyloxy)ethoxy-;
1-(cyclohexylcarbonyloxy)ethoxy-;
i-propyloxycarbonyloxymethoxy-;
t-butyloxycarbonyloxymethoxy-;
1-(i-propyloxycarbonyloxy)ethoxy-;
1-(cyclohexyloxycarbonyloxy)ethoxy-;
1-(t-butyloxycarbonyloxy)ethoxy-;
dimethylaminoethoxy-;
diethylaminoethoxy-;
(5-methyl-1,3-dioxacyclopenten-2-on-4-yl)methoxy-;
(5-(t-butyl)-1,3-dioxacyclopenten-2-on-4-yl)methoxy-;
(1,3-dioxa-5-phenyl-cyclopenten-2-on-4-yl)methoxy-; and
1-(2-(2-methoxypropyl)carbonyloxy)ethoxy-;

W$^a$ is H or —NHR$^{16}$;

W$^b$ is H, methyl, ethyl, benzyl, phenethyl, pyridyl, pyridylmethyl, pyridylethyl, (indol-3-yl)ethyl, CH$_2$C(=O)NHR$^{18}$, or CH$_2$NHR$^{16}$;

R$^8$ is selected from:
H, hydroxy, cyano, —CO$_2$R$^{12}$, —C(=O)R$^{13}$, —C(=O)NR$^{23}$R$^{24}$, —NR$^{25}$R$^{26}$, —SR$^{14}$, —SOR$^{14}$, —SO$_2$R$^{14}$, C$_1$–C$_{10}$ alkoxy, C$_1$–C$_{10}$ alkylcarbonyl,
aryl, wherein said aryl is substituted with 0–3 groups selected from halogen, C$_1$–C$_6$ alkoxy, C$_1$–C$_6$ alkyl, CF$_3$, CO$_2$R$^{12}$, SO$_2$Me, SOMe, SMe and —NMe$_2$, and
a 5–10 membered heterocyclic ring system selected from pyridinyl, furanyl, thiazolyl, thienyl, pyrrolyl, pyrazolyl, triazolyl, imidazolyl, benzofuranyl, indolyl, inolinyl, quinolinyl, isoquinolinyl, benzimidazolyl, piperidinyl, tetrahydrofuranyl, pyranyl, 3H-indolyl, pyrrolidinyl, piperidinyl, isoxazolinyl, isoxazolyl and morpholinyl;

R$^{15}$ is selected from H, OH, —OR$^{12}$, and —OC(=O)NR$^{23}$R$^{24}$;

R$^{16}$ is —C(=O)OR$^{17}$ or —SO$_2$R$^{17}$;

R$^{17}$ is selected from:
C$_1$–C$_8$ alkyl,
C$_2$–C$_8$ alkenyl,
aryl substituted with 0–4 R$^{19}$,
aryl(C$_1$–C$_6$ alkyl)-substituted with 0–4 R$^{19}$,
a 5–10 membered heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzyimdazolyl, piperidinyl, tetrahydrofuranyl, pyranyl, pyrimidinyl, 3H-indolyl, pyrrolidinyl, morpholinyl, and piperazinyl, said heterocyclic ring being substituted with 0–4 R$^{19}$, said heterocyclic ring being substituted with 0–4 R$^{19}$, and
C$_1$–C$_6$ alkyl substituted with a 5–10 membered heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzyimdazolyl, piperidinyl, tetrahydrofuranyl, pyranyl, pyrimidinyl, 3H-indolyl, pyrrolidinyl, morpholinyl, and piperazinyl, said heterocyclic ring being substituted with 0–4 R$^{19}$;

$R^{19}$ is selected from H, halogen, $CF_3$, CN, $NO_2$, $NR^{25}R^{26}$, $C_1$–$C_8$ alkyl, $C_2$–$C_6$ alkenyl, $C_2$–$C_6$ alkynyl, $C_3$–$C_{11}$ cycloalkyl, $C_3$–$C_{11}$ cycloalkyl ($C_1$–$C_4$ alkyl)-, aryl, aryl($C_1$–$C_6$ alkyl)-, $C_1$–$C_6$ alkoxy, and $C_1$–$C_4$ alkoxycarbonyl;

n is 0 or 1;
q is 1, 2, 3, or 4;
r is 0, 1, or 2; and
s is 1, 2, 3, or 4.

4. A compound according to claim 3 wherein:
$R^1$ is $R^2(R^{2b})N(R^3N=)C$—V— or $R^2(R^{2b})N(R^3N=)CNH$—V—;
  V is -(pyridyl)- or -(phenyl)-, said phenyl substituted with 0–2 groups independently selected from F, Br, methyl, and methoxy;
  Z is a bond or O;
  $R^2$, $R^{2b}$, and $R^3$ are independently selected from:
    H, $C_1$–$C_6$ alkyl, $C_3$–$C_6$ alkenyl, $C_3$–$C_6$ alkynyl, $C_3$–$C_8$ cycloalkyl, $C_3$–$C_8$ cycloalkyl($C_1$–$C_4$ alkyl)-, $C_2$–$C_7$ alkylcarbonyl, $C_1$–$C_4$ haloalkyl, arylcarbonyl, aryl($C_1$–$C_4$ alkyl)-, benzhydryl, heteroaryl, heteroaryl($C_1$–$C_4$ alkyl)-,
    $C_1$–$C_4$ alkoxycarbonyl,
    $C_3$–$C_6$ cycloalkoxycarbonyl,
    $C_7$–$C_{11}$ bicycloalkoxycarbonyl,
    aryl($C_1$–$C_8$ alkoxy)carbonyl,
    ($C_1$–$C_6$ alkyl)carbonyloxy($C_1$–$C_4$ alkoxy)carbonyl,
    arylcarbonyloxy($C_1$–$C_4$ alkoxy)carbonyl, and
    ($C_3$–$C_8$ cycloalkyl)carbonyloxy($C_1$–$C_4$ alkoxy)carbonyl;
  wherein at least one of $R^2$, $R^{2b}$, and $R^3$ is H,
    $C_1$–$C_4$ alkoxycarbonyl,
    $C_3$–$C_6$ cycloalkoxycarbonyl,
    $C_7$–$C_{11}$ bicycloalkoxycarbonyl,
    aryl($C_1$–$C_8$ alkoxy)carbonyl,
    ($C_1$–$C_6$ alkyl)carbonyloxy($C_1$–$C_4$ alkoxy)carbonyl,
    arylcarbonyloxy($C_1$–$C_4$ alkoxy)carbonyl, or
    ($C_3$–$C_8$ cycloalkyl)carbonyloxy($C_1$–$C_4$ alkoxy) carbonyl;
  wherein said aryl groups of $R^2$, $R^{2b}$, and $R^3$ may be substituted with 0–3 groups selected from hydroxy, halogen, methoxy, ethoxy, propoxy, butoxy, methyl, ethyl, propyl, butyl, $CF_3$, —CN, —$SO_2(CH_3)$, —$SO_2(C_2H_5)$, —$SO_2(C_3H_7)$, —$SO_2(C_4H_9)$, —$NR^{21}R^{22}$, $C_1$–$C_4$ haloalkyl, methylenedioxydiyl, and ethylenedioxydiyl; and
    said heteroaryl groups of $R^2$, $R^{2b}$, and $R^3$ may be substituted with 0–2 groups selected from hydroxy, halogen, methoxy, ethoxy, propoxy, butoxy, methyl, ethyl, propyl, butyl, $CF_3$, $SO_2CH_3$, and —$NR^{21}R^{22}$;
  alternatively, $R^2$ and $R^{2b}$ can be taken together with the nitrogen atom to which they are attached to form a 5–10 membered heterocyclic ring system selected from morpholine, piperidine, piperazine, pyrrolidine, tetrahydroisoquinoline, thiazolidine, thiomorpholine, 1,4-benzoxazine, 8-oxo-3-azabicyclo[3.2.1]octane, 1,4-dioxa-8-azaspiro[4.5]decane, and azepine, said heterocyclic ring being substituted with 0–2 $R^4$;
  $R^4$, when a substituent on carbon, is independently selected from H, methyl, ethyl, propyl, butyl, and phenyl; wherein said phenyl groups may be optionally substituted with 0–3 groups selected from hydroxy, halogen, methoxy, methyl, ethyl, $CF_3$, $SCH_3$, —$NH_2$, —NH($CH_3$), —N($CH_3$)$_2$, methylenedioxydiyl, and ethylenedioxydiyl;
  alternatively, when two $R^4$ groups are attached to adjacent carbon atoms, they may be taken together with the atoms to which they are attached to form a fused 5–7 membered saturated, unsaturated or aromatic carbocyclic ring;
  alternatively, when $R^4$ is attached to a saturated carbon atom, it may also be =O or =S;
  $R^4$, when a substituent on nitrogen, is independently selected from H, methyl, ethyl, propyl, butyl, cyclopropyl, cyclopropylmethyl, phenyl, phenylmethyl, phenylethyl, pyridyl, and pyridylmethyl;
    wherein said phenyl or pyridyl groups may be additionally substitututed with 0–2 groups selected from hydroxy, halogen, methoxy, methyl, ethyl, $CF_3$, $SCH_3$, —$NH_2$, —NH($CH_3$), and —N($CH_3$)$_2$;
  $R^4$, when a substituent on sulfur, may be =O;
  X is —$CH_2CH(W^a)$—, —$CH(W^a)$—, or —$OCH(W^b)$-;
  Y is selected from hydroxy; methoxy; ethoxy; isopropoxy; n-butyloxy; isobutyloxy; t-butoxy; benzyloxy; methylcarbonyloxymethoxy-;
    ethylcarbonyloxymethoxy-;
    t-butylcarbonyloxymethoxy-;
    cyclohexylcarbonyloxymethoxy-;
    1-(methylcarbonyloxy)ethoxy-;
    1-(ethylcarbonyloxy)ethoxy-;
    1-(t-butylcarbonyloxy)ethoxy-;
    1-(cyclohexylcarbonyloxy)ethoxy-;
    i-propyloxycarbonyloxymethoxy-;
    t-butyloxycarbonyloxymethoxy-;
    1-(i-propyloxycarbonyloxy)ethoxy-;
    1-(cyclohexyloxycarbonyloxy)ethoxy-;
    1-(t-butyloxycarbonyloxy)ethoxy-;
    dimethylaminoethoxy-;
    diethylaminoethoxy-;
    (5-methyl-1,3-dioxacyclopenten-2-on-4-yl)methoxy-;
    (5-(t-butyl)-1,3-dioxacyclopenten-2-on-4-yl)methoxy-;
    (1,3-dioxa-5-phenyl-cyclopenten-2-on-4-yl)methoxy-; and
    1-(2-(2-methoxypropyl)carbonyloxy)ethoxy-;
  $W^a$ is H or —$NHR^{16}$;
  $W^b$ is H, methyl, ethyl, benzyl, phenethyl, pyridyl, pyridylmethyl, pyridylethyl, (indol-3-yl)ethyl, $CH_2C(=O)NHR^{18}$, or $CH_2NHR^{16}$;
  $R^8$ is selected from:
    H, hydroxy, cyano, —$CO_2R^{12}$, —$C(=O)R^{13}$, —$C(=O)NR^{23}R^{24}$, —$NR^{25}R^{26}$, —$SR^{14}$, —$SOR^{14}$, —$SO_2R^{14}$, $C_1$–$C_4$ alkoxy, $C_1$–$C_4$ alkylcarbonyl,
    aryl, wherein said aryl is substituted with 0–3 groups selected from halogen, methoxy, ethoxy, propoxy, butoxy, methyl, ethyl, propyl, butyl, $CF_3$, $CO_2R^{12}$, $SO_2Me$, SOMe, SMe and —$NMe_2$, and
    a 5–10 membered heterocyclic ring system selected from pyridinyl, furanyl, thiazolyl, thienyl, pyrrolyl, pyrazolyl, triazolyl, imidazolyl, benzofuranyl, indolyl, inolinyl, quinolinyl, isoquinolinyl, benzimidazolyl, piperidinyl, tetrahydrofuranyl, pyranyl, 3H-indolyl, pyrrolidinyl, piperidinyl, isoxazolinyl, isoxazolyl and morpholinyl;
  $R^{15}$ is H;
  $R^{16}$ is —$SO_2R^{17}$, —$C(=O)OCH_2CH_2CH_2CH_3$, —$C(=O)OCH_2CH(CH_3)_2$ or —$C(=O)OCH_2(C_6H_5)$;

$R^{17}$ is selected from:
  $C_1$–$C_8$ alkyl,
  aryl substituted with 0–2 $R^{19}$,
  aryl($C_1$–$C_6$ alkyl)-substituted with 0–2 $R^{19}$,
  a 5–10 membered heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzyimdazolyl, piperidinyl, tetrahydrofuranyl, pyranyl, pyrimidinyl, 3H-indolyl, pyrrolidinyl, morpholinyl, and piperazinyl, said heterocyclic ring being substituted with 0–2 $R^{19}$, said heterocyclic ring being substituted with 0–2 $R^{19}$, and
  $C_1$–$C_6$ alkyl substituted with a 5–10 membered heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzyimdazolyl, piperidinyl, tetrahydrofuranyl, pyranyl, pyrimidinyl, 3H-indolyl, pyrrolidinyl, morpholinyl, and piperazinyl, said heterocyclic ring being substituted with 0–2 $R^{19}$;

$R^{19}$ is selected from:
  H, halogen, $CF_3$, CN, $NO_2$, $NR^{25}R^{26}$, $C_1$–$C_4$ alkyl, $C_2$–$C_4$ alkenyl, $C_2$–$C_4$ alkynyl, $C_3$–$C_6$ cycloalkyl, $C_3$–$C_6$ cycloalkyl($C_1$–$C_4$ alkyl)-, aryl, aryl($C_1$–$C_4$ alkyl)-, $C_1$–$C_4$ alkoxy, and $C_1$–$C_4$ alkoxycarbonyl;

n is 1; and
s is 1 or 2.

5. A compound of claim 1 selected from the group:
[[1-[3-[4-(aminoiminomethyl)phenyl]isoxazolin-5-ylmethyl]-4-piperidinyl]oxy]acetic acid;
[[1-[3-[4-[(n-butylamino)iminomethyl]phenyl]isoxazolin-5-ylmethyl]-4-piperidinyl]oxy]acetic acid;
[[1-[3-[4-[(2-phenylethylamino)iminomethyl]phenyl]isoxazolin-5-ylmethyl]-4-piperidinyl]oxy]acetic acid;
[[1-[3-[4-[(phenylmethylamino)iminomethyl]phenyl]isoxazolin-5-ylmethyl]-4-piperidinyl]oxy]acetic acid;
[[1-[3-[4-[(n-propylamino)iminomethyl]phenyl]isoxazolin-5-ylmethyl]-4-piperidinyl]oxy]acetic acid;
[[1-[3-[4-[(ethylamino)iminomethyl]phenyl]isoxazolin-5-ylmethyl]-4-piperidinyl]oxy]acetic acid;
[[1-[3-[4-[(morpholino)iminomethyl]phenyl]isoxazolin-5-ylmethyl]-4-piperidinyl]oxy]acetic acid;
[[1-[3-[4-[(piperidino)iminomethyl]phenyl]isoxazolin-5-ylmethyl]-4-piperidinyl]oxy]acetic acid;
[[1-[3-[4-[(thiazolidino)iminomethyl]phenyl]isoxazolin-5-ylmethyl]-4-piperidinyl]oxy]acetic acid;
[[1-[3-[4-[(2,6-dimethylmorpholino)iminomethyl]phenyl]isoxazolin-5-ylmethyl]-4-piperidinyl]oxy]acetic acid;
[[1-[3-[4-[(4-methylpiperazino)iminomethyl]phenyl]isoxazolin-5-ylmethyl]-4-piperidinyl]oxy]acetic acid;
[[1-[3-[4-[(4-phenylpiperazino)iminomethyl]phenyl]isoxazolin-5-ylmethyl]-4-piperidinyl]oxy]acetic acid;
[[1-[3-[4-[(pyrrolidino)iminomethyl]phenyl]isoxazolin-5-ylmethyl]-4-piperidinyl]oxy]acetic acid;
[[1-[3-[4-[(2,6-dimethylpiperazino)iminomethyl]phenyl]isoxazolin-5-ylmethyl]-4-piperidinyl]oxy]acetic acid;
[[1-[3-[4-[(2-fluorophenyl)piperazino)iminomethyl]phenyl]isoxazolin-5-ylmethyl]-4-piperidinyl]oxy]acetic acid;
[[1-[3-[4-[(2-methylphenyl)piperazino)iminomethyl]phenyl]isoxazolin-5-ylmethyl]-4-piperidinyl]oxy]acetic acid;
[[1-[3-[4-[(thiomorpholino)iminomethyl]phenyl]isoxazolin-5-ylmethyl]-4-piperidinyl]oxy]acetic acid;
[[1-[3-[4-[(4-pyridylethylamino)iminomethyl]phenyl]isoxazolin-5-ylmethyl]-4-piperidinyl]oxy]acetic acid;
[[1-[3-[4-[(4-propylpiperazino)iminomethyl]phenyl]isoxazolin-5-ylmethyl]-4-piperidinyl]oxy]acetic acid;
[[1-[3-[4-[(1,2,3,4-tetrahydroisoquinolino)iminomethyl]phenyl]isoxazolin-5-ylmethyl]-4-piperidinyl]oxy]acetic acid;
[[1-[3-[4-[(1,2,3,4-tetrahydro-2,7-naphthyridino)iminomethyl]phenyl]isoxazolin-5-ylmethyl]-4-piperidinyl]oxy]acetic acid;
[1-[3-[4-(aminoiminomethyl)phenyl]isoxazolin-5-ylmethyl]-4-piperidinyl]acetic acid;
[1-[3-[4-[(n-butylamino)iminomethyl]phenyl]isoxazolin-5-ylmethyl]-4-piperidinyl]acetic acid;
[1-[3-[4-[(2-phenylethylamino)iminomethyl]phenyl]isoxazolin-5-ylmethyl]-4-piperidinyl]acetic acid;
[1-[3-[4-[(phenylmethylamino)iminomethyl]phenyl]isoxazolin-5-ylmethyl]-4-piperidinyl]acetic acid;
[1-[3-[4-[(n-propylamino)iminomethyl]phenyl]isoxazolin-5-ylmethyl]-4-piperidinyl]acetic acid;
[1-[3-[4-[(ethylamino)iminomethyl]phenyl]isoxazolin-5-ylmethyl]-4-piperidinyl]acetic acid;
[1-[3-[4-[(morpholino)iminomethyl]phenyl]isoxazolin-5-ylmethyl]-4-piperidinyl]acetic acid;
[1-[3-[4-[(piperidino)iminomethyl]phenyl]isoxazolin-5-ylmethyl]-4-piperidinyl]acetic acid;
[1-[3-[4-[(thiazolidino)iminomethyl]phenyl]isoxazolin-5-ylmethyl]-4-piperidinyl]acetic acid;
[1-[3-[4-[(2,6-dimethylmorpholino)iminomethyl]phenyl]isoxazolin-5-ylmethyl]-4-piperidinyl]acetic acid;
[1-[3-[4-[(4-methylpiperazino)iminomethyl]phenyl]isoxazolin-5-ylmethyl]-4-piperidinyl]acetic acid;
[1-[3-[4-[(4-phenylpiperazino)iminomethyl]phenyl]isoxazolin-5-ylmethyl]-4-piperidinyl]acetic acid;
[1-[3-[4-[(pyrrolidino)iminomethyl]phenyl]isoxazolin-5-ylmethyl]-4-piperidinyl]acetic acid;
[1-[3-[4-[(2,6-dimethylpiperazino)iminomethyl]phenyl]isoxazolin-5-ylmethyl]-4-piperidinyl]acetic acid;
[1-[3-[4-[(2-fluorophenyl)piperazino)iminomethyl]phenyl]isoxazolin-5-ylmethyl]-4-piperidinyl]acetic acid;
[1-[3-[4-[(2-methylphenyl)piperazino)iminomethyl]phenyl]isoxazolin-5-ylmethyl]-4-piperidinyl]acetic acid;
[1-[3-[4-[(thiomorpholino)iminomethyl]phenyl]isoxazolin-5-ylmethyl]-4-piperidinyl]acetic acid;
[1-[3-[4-[(4-pyridylethylamino)iminomethyl]phenyl]isoxazolin-5-ylmethyl]-4-piperidinyl]acetic acid;
[1-[3-[4-[(4-propylpiperazino)iminomethyl]phenyl]isoxazolin-5-ylmethyl]-4-piperidinyl]acetic acid;
[1-[3-[4-[(1,2,3,4-tetrahydroisoquinolino)iminomethyl]phenyl]isoxazolin-5-ylmethyl]-4-piperidinyl]acetic acid; and
[1-[3-[4-[(1,2,3,4-tetrahydro-2,7-naphthyridino)iminomethyl]phenyl]isoxazolin-5-ylmethyl]-4-piperidinyl]acetic acid.

6. A compound according to claim 5 wherein the stereochemistry of the isoxazolin-5-ylmethyl moiety is isoxazolin-5(S)-ylmethyl.

7. A compound according to claim 5 wherein the stereochemistry of the isoxazolin-5-ylmethyl moiety is isoxazolin-5(R)-ylmethyl.

8. A pharmaceutical composition comprising a pharmaceutically acceptable carrier and a therapeutically effective amount of a compound of claim 1 or a pharmaceutically acceptable salt form thereof.

9. A method of inhibiting the aggregation of blood platelets which comprises administering to a host in need of such inhibition a therapeutically effective amount of a compound of claim 1.

10. A method of treating thrombosis, inflammation, bone degradation, tumor, metastasis, or a cell aggregation-related condition which comprises administering to a host in need of such treatment a therapeutically effective amount of a compound of claim 1.

11. A method of treating rheumatoid arthritis, asthma, allergy, adult respiratory distress syndrome, graft versus host disease, organ transplantation, septic shock, psoriasis, eczema, contact dermatitis, osteoporosis, osteoarthritis, atherosclerosis, metastasis, wound healing, diabetic retinopathy, inflammatory bowel disease or other autoimmune disease which comprises administering to a host in need of such treatment a therapeutically effective amount of a compound of claim 1.

12. A method of treating thromboembolic disorders selected from thrombus or embolus formation, harmful platelet aggregation, reocclusion following thrombolysis, reperfusion injury, restenosis, atherosclerosis, stroke myocardial infarction, and unstable angina, which comprises administering to a host in need of such treatment a therapeutically effective amount of a compound of claim 1.

* * * * *